United States Patent [19]

Holzrichter et al.

[11] Patent Number: 5,729,694
[45] Date of Patent: Mar. 17, 1998

[54] SPEECH CODING, RECONSTRUCTION AND RECOGNITION USING ACOUSTICS AND ELECTROMAGNETIC WAVES

[75] Inventors: John F. Holzrichter, Berkeley; Lawrence C. Ng, Danville, both of Calif.

[73] Assignee: The Regents of the University of California, Oakland, Calif.

[21] Appl. No.: 597,589

[22] Filed: Feb. 6, 1996

[51] Int. Cl.$^6$ .............................. G10L 3/02; G10L 9/00
[52] U.S. Cl. ................ 395/2.17; 395/2.79; 395/2.23
[58] Field of Search ........................... 395/2.1, 2.17, 395/2.79, 2.42, 2.34, 2.14–2.16, 2.23

[56] References Cited

U.S. PATENT DOCUMENTS

| | | | |
|---|---|---|---|
| 4,897,630 | 1/1990 | Nykerk | 340/426 |
| 5,285,521 | 2/1994 | Holt et al. | 395/2.79 |
| 5,524,148 | 6/1996 | Allen et al. | 379/391 |

OTHER PUBLICATIONS

Flanagan, J. L. "Technologies for Multimedia Communications", Proceedings of IEEE 82(4), 590–603 (1994).
Rothenberg, M. "A new inverse-filtering technique for deriving the glottal air flow waveform during voicing", J. Acoustic Soc. Am., 53(6), 1632–1645 (1973).
Sondhi, M. M. and Resnick, J. R. "The inverse problem for the vocal tract: Numerical methods, acoustical experiments, and speech synthesis", J. Acoustic Soc. Am. 73(3), 985–1002 (1983).
Flanagan, J. L. "Speech Analysis Synthesis and Perception", Academic Press, NY, 40–41 (1965).
Oppenheim, A. V. and Schafer, R. W. "Digital Signal Processing", Prentice–Hall, 195–207.
Coker, C.H. "A Model of Articulatory Dynamics and Control", Proc. IEEE, 64(4), 452–459 (1976).
Sondhi, M. M. and Schroeter,J. "A Hybrid Time–Frequency Domain Articulatory Speech Synthesizer", IEEE Trans. on Acoustics, Speech, and Signal Processing, ASSP–35 (7), 955–967 (1987).
Klatt, D. H. "Review of text–to–speech conversion for English", J. Acoustic Soc. Am. 82(3), 737–793.
Koo et al, "An experimental field trial of large vocabulary speaker independent recognition system"; IEEE Workshop on interactive voice technology for telecommunications applications, pp. 33–36. Sep. 1994.
Boothroyd et al, "Video game for speech perception testing and training young hearing–impaired children"; Proceedings of the Johns Hopkins Nationa Search for computing applications to assist persons with disabilities, pp. 25–28. Feb. 1992.

*Primary Examiner*—Tariq R. Hafiz
*Attorney, Agent, or Firm*—Henry P. Sartorio

[57] ABSTRACT

The use of EM radiation in conjunction with simultaneously recorded acoustic speech information enables a complete mathematical coding of acoustic speech. The methods include the forming of a feature vector for each pitch period of voiced speech and the forming of feature vectors for each time frame of unvoiced, as well as for combined voiced and unvoiced speech. The methods include how to deconvolve the speech excitation function from the acoustic speech output to describe the transfer function each time frame. The formation of feature vectors defining all acoustic speech units over well defined time frames can be used for purposes of speech coding, speech compression, speaker identification, language-of-speech identification, speech recognition, speech synthesis, speech translation, speech telephony, and speech teaching.

43 Claims, 21 Drawing Sheets

(1, 14, 10, 0, 0, 0, 300, 120, 20, 0.0167, -15, 5×10-5, -25, ....., -n db, .... POLE VALUES,)

- RATIO OF 2nd HARMONIC TO FUNDAMENTAL
- BANDWIDTH OF FUNDAMENTAL IN HZ
- FUNDAMENTAL FREQUENCY OF EXCITATION IN HZ
- EXCITATION FUNCTION ENVELOPE WIDTH, MSEC
- DEGREES PHASE CHANGE RELATIVE TO FIRST HARMONIC
- TYPE OF CONNECTION TO FOLLOWING SOUND
- TYPE OF CONNECTION TO PRECEEDING SOUND
- ISOLATED SOUND =0, ISOLATED WORD =1 SENTENCE OR PHRASE =2 ETC.
- NUMBER OF ZEROS
- NUMBER OF POLES
- DESIGNATOR OF TRANSFER FUNCTION TO BE USED
- RATIO OF 3rd HARMONIC TO FUNDAMENTAL
- DEGREE PHASE CHANGE OF 3rd RELATIVE TO FIRST HARMONIC
- REDUCTION IN HARMONICS >10th, IN db PER OCTAVE, PHASE PER OCTAVE
- SEE TABLE 11 FOR VALUES
- ZERO VALUES, Ea, ah
- ACOUSTIC ENERGY IN FRAME
- THE SPEECH UNIT SYMBOL
- SEE TABLE 11 FOR VALUES

FIG. 12A

| Z-Plane Zeros | Z-plane Poles |
|---|---|
| 0.4576 + 1.4440i | -0.9289 |
| 0.4576 - 1.4440i | -0.6860 + 0.6104i |
| 1.0815 + 0.8980i | -0.6860 - 0.6104i |
| 1.0815 - 0.8980i | -0.4111 + 0.8540i |
| -0.3252 + 1.2521i | -0.4111 - 0.8540i |
| -0.3252 - 1.2521i | 0.0367 + 0.9656i |
| -0.8458 + 0.7755i | 0.0367 - 0.9656i |
| -0.8458 - 0.7755i | 0.8825 |
| 1.1037 | 0.8754 + 0.3664i |
| -0.9574 | 0.8754 - 0.3664i |
| | 0.7405 + 0.6016i |
| | 0.7405 - 0.6016i |
| | 0.2343 + 0.7068i |
| | 0.2343 - 0.7068i |

FIG. 12B

| coeff. vector a | coeff. vector b |
|---|---|
| 1.0000 | 0.0055 |
| -2.0451 | -0.0350 |
| 1.9064 | 0.0419 |
| -0.9941 | -0.0166 |
| 0.8417 | 0.0285 |
| -0.4840 | -0.0142 |
| -0.4557 | -0.0331 |
| 0.8479 | -0.0341 |
| -0.1022 | -0.0208 |
| -0.3799 | |
| 0.1873 | |

FIG. 12C

SPEECH CODING, RECONSTRUCTION AND RECOGNITION USING ACOUSTICS AND ELECTROMAGNETIC WAVES

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to the characterization of human speech using combined EM wave information and acoustic information, for purposes of speech coding, speech recognition, speech synthesis, speaker identification, and related speech technologies.

Speech Characterization and Coding:

The history of speech characterization, coding, and generation has spanned the last one and one half centuries. Early mechanical speech generators relied upon using arrays of vibrating reeds and tubes of varying diameters and lengths to make human-voice-like sounds. The combinations of excitation sources (e.g., reeds) and acoustic tracts (e.g., tubes) were played like organs at theaters to mimic human voices. In the 20th century, the physical and mathematical descriptions of the acoustics of speech began to be studied intensively and these were used to enhance many commercial products such as those associated with telephony and wireless communications. As a result, the coding of human speech into electrical signals for the purposes of transmission was extensively developed, especially in the United States at the Bell Telephone Laboratories. A complete description of this early work is given by J. L. Flanagan, in "Speech Analysis, Synthesis, and Perception", Academic Press, New York, 1965. He describes the physics of speech and the mathematics of describing acoustic speech units (i.e., coding). He gives examples of how human vocal excitation sources and the human vocal tracts behave and interact with each other to produce human speech.

The commercial intent of the early telephone work was to understand how to use the minimum bandwidth possible for transmitting acceptable vocal quality on the then-limited number of telephone wires and on the limited frequency spectrum available for radio (i.e. wireless) communication. Secondly, workers learned that analog voice transmission uses typically 100 times more bandwidth than the transmission of the same word if simple numerical codes representing the speech units such as phonemes or words are transmitted. This technology is called "Analysis-Synthesis Telephony" or "Vocoding". For example, sampling at 8 kHz and using 16 bits per analog signal value requires 128 kbps, but the Analysis Synthesis approach can lower the coding requirements to below 1.0 kbps. In spite of the bandwidth advantages, vocoding has not been used widely because it requires accurate automated phoneme coding and resynthesis; otherwise the resulting speech tends to have a "machine accent" and be of limited intelligibility. One major aspect of the difficulty of speech coding is adequacy of the excitation information, including the pitch measurement, the voiced-unvoiced discrimination, and the spectrum of the glottal excitation pulse.

Progress in speech acoustical understanding and mathematical modeling of the vocal tract has continued and become quite sophisticated, mostly in the laboratory. It is now reasonably straightforward to simulate human speech by using differential equations which describe the increasingly complex concatenations of sound excitation sources, vocal tract tubes, and their constrictions and side branches (e.g., vocal resonators). Transform methods (e.g. electrical analogies solved by Fourier, Laplace, Z-transforms, etc.) are used for simpler cases and sophisticated computational modeling on supercomputers for increasingly complex and accurate simulations. See Flanagan (ibid.) for early descriptions of modeling, and Schroeter and Sondhi, "A hybrid time-frequency domain articulator speech synthesizer", IEEE Trans. on Acoustic Speech, ASSP 35(7) 1987 and "Techniques for Estimating Vocal-Tract Shapes from the Speech Signal", ASSP 2(1), 1343, 1994. These papers reemphasize that it is not possible to work backwards from the acoustic output to obtain a unique mathematical description of the combined vocal fold-vocal tract system, which is called the "inverse problem" herein. It is not possible to obtain information that separately describes both the "zeros" in speech air flow caused by glottal (i.e., vocal fold) closure and those caused by closed, or resonant structures in the vocal tract. As a result, it is not possible to use the well developed mathematics of modern signal acquisition, processing, coding, and reconstructing to the extent needed.

In addition, given a mathematical vocal system model, it remains especially difficult to associate it with a unique individual because it is very difficult to obtain the detailed physiological vocal tract features of a given individual such as tract lengths, diameters, cross sectional shapes, wall compliance, sinus size, glottal size and compliance, lung air pressure, and other necessary parameters. In some cases, deconvolving the excitation source from the acoustic output can be done for certain sounds where the "zeros" are known to be absent, so the major resonant structures such as tract lengths can be determined. For example, simple acoustic resonator techniques (see the 1976 U.S. Pat. No. 4,087,632 by Hafer) are used to derive the tongue body position by measuring the acoustic formant frequencies (i.e., the vocal tube resonance frequencies) and to constrain the tongue locations and tube lengths against an early, well known vocal tract model by Coker, "A Model of Articulatory Dynamics and Control", Proc. of IEEE, Vol. 64(4), 452–460, 1976. The problem with this approach is that only gross dimensions of the tract are obtained, but detailed vocal tract features are needed to unambiguously define the physiology of the human doing the speaking. For more physiological details, x-ray imaging of the vocal tract has been used to obtain tube lengths, diameters, and resonator areas and structures. Also the optical laryngoscope, inserted into the throat, to view the vocal fold open and close cycles, is used in order to observe their sizes and time behavior.

The limit to further performance improvements in acoustic speech recognition, in speech synthesis, in speaker identification, and other related technologies is directly related to our inability to accurately solve the inverse problem. Present workers are unable to use acoustic speech output to work backwards to accurately and easily determine the vocal tract transfer function, as well as the excitation amplitude versus time. The "missing" information about the separation of the excitation function from the vocal tract transfer function leads to many difficulties in automating the coding of the speech for each speech time frame and in forming speech sound-unit libraries for speech-related technologies. A major reason for the problem is that workers have been unable to measure the excitation function in real time. This has made it difficult to automatically identify the start and stop of each voiced speech segments over which a speech sound unit is constant. This has made it difficult to join (or to unjoin) the transitions between sequential vocalized speech units (e.g., syllables, phonemes or multiplets of phonemes) as an individual human speaker articulates sounds at rates of approximately 10 phonemes per second or two words per second.

The lack of precision in speech segment identification adds to the difficulty in obtaining accurate model coefficients for both the excitation function and the vocal tract. Further, this leads to inefficiencies in the algorithms and the computational procedures required by the technological application such as speech recognition. In addition, the difficulties described above prevent the accurate coding of the unique acoustic properties of a given individual for personalized, human speech synthesis or for pleasing vocoding. In addition, the "missing" information prevents complete separation of the excitation from the transfer function, and limits accurate speaker-independent speech-unit coding (speaker normalization). The incomplete normalization limits the ability to conduct accurate and rapid speech recognition and/or speaker identification using statistical codebook lookup techniques, because the variability of each speaker's articulation adds uncertainty in the matching process and requires additional statistical processing. The missing information and the timing difficulties also inhibit the accurate handling of co-articulation, incomplete articulation, and similar events where words are run together in the sequences of acoustic units comprising a speech segment.

In the 1970s, workers in the field of speech recognition showed that short "frames" (e.g., 10 ms intervals) of the time waveform of a speech signal could be well approximated by an all poles (but no zeros) analytic representation, using numerical "linear predictive coding" (LPC) coefficients found by solving covariance equations. Specific procedures are described in B. S. Atal and S. L. Hanauer, "Speech analysis and synthesis by linear prediction of the speech wave", J. Acoust. Soc. Am. 50(2), pp. 63, 1971. The LPC coefficients are a form of speech coding and have the advantage of characterizing acoustic speech with a relatively small number of variables-typically 20 to 30 per frame as implemented in today's systems. They make possible statistical table look up of large numbers of word representations using Hidden Markov techniques for speech recognition.

In speech synthesizers, code books of acoustic coefficients (e.g., using well known LPC, PARCOR, or similar coefficients) for each of the phonemes and for a sufficient number of diphonemes (i.e. phoneme pairs) are constructed. Upon demand from text-to-speech generators, they are retrieved and concatenated to generate synthetic speech. However, as an accurate coding technique, they only approximate the speech frames they represent. Their formation and use is not based upon using knowledge of the excitation function, and as a result they do not accurately describe the condition of the articulators. They are also inadequate for reproducing the characteristics of the given human speaker. They do not permit natural concatenation into high quality natural speech. They can not be easily related to an articulatory speech model to obtain speaker-specific physiological parameters. Their lack of association with the articulatory configuration makes it difficult to do speaker normalization, as well as to deal with the coarticulation and incomplete articulation problem of natural speech.

Present Example of Speech Coding:

Rabiner, in "Applications of Voice Processing to Telecommunications" Proc. of the IEEE 82, 199 February 1994 points out that several modern text-to-speech synthesis systems in use today by AT&T use 2000 to 4000 diphonemes, which are needed to simulate the phoneme-tophoneme transitions in the concatenation process for natural speech sounds. FIG. 1 shows a prior art open loop acoustic speech coding system in which acoustic signals from a microphone are processed, e.g. by LPC, and feature vectors are produced and stored in a library. Rabiner also points out (page 213) that in current synthesis models, the vocal source excitation and the vocal tract interaction "is grossly inadequate", and also that "when natural duration and pitch are copied onto a text-to-speech utterance, . . . the quality of the . . . synthetic speech improves dramatically." Presently, it is not possible to economically capture the natural pitch duration and voiced air-pulse amplitude vs. time, as well as individual vocal tract qualities, of a given individual's voice in any of the presently used models, except by very expensive and invasive laboratory measurements and computations.

J. L. Flanagan, "Technologies for Multimedia Communications", Proc. IEEE 82, 590, April 1994, describes low bandwidth speech coding: "At fewer than 1 bit per Nyquist sample, source coding is needed to additionally take into account the properties of the signal generator (such as voiced/unvoiced distinctions in speech, and pitch, intensity, and formant characteristics)." There is no presently, commercially useful method to account for the speech excitation source in order to minimize the coding complexity and subsequent bandwidth.

EM Sensors and Acoustic Information:

The use of EM sensors for measuring speech organ conditions for the purposes of speech recognition and related technologies are described in copending U.S. patent application Ser. No. 08/597,596 by Holzrichter. Although it has been recognized for many decades in the field of speech recognition that speech organ position and motion information could be useful, and EM sensors (e.g. rf and microwave radars) were available to do the measurement, no one had suggested a system using such sensors to detect the motions and locations of speech organs. Nor had anyone described how to use this information to code each speech unit and to use the code in an algorithm to identify the speech unit, or for other speech technology applications such as synthesis. Holzrichter showed how to use EM sensor information with simultaneously obtained acoustic data to obtain the positions of vocal organs, how to define feature vectors from this organ information to use as a coding technique, and how to use this information to do high-accuracy speech recognition. He also pointed out that this information provided a natural method of defining changes in each phoneme by measuring changes in the vocal organ conditions, and he described a method to automatically define each speech time frame. He also showed that "photographic quality" EM wave images, obtained by tomographic or similar techniques, were not necessary for the implementation of the procedures he described, nor for the procedures described herein.

SUMMARY OF THE INVENTION

Accordingly it is an object of the invention to provide method and apparatus for speech coding using nonacoustic information in combination with acoustic information.

It is also an object of the invention to provide method and apparatus for speech coding using Electromagnetic (EM) wave generation and detection modules in combination with acoustic information.

It is also an object of the invention to provide method and apparatus for speech coding using radar in combination with acoustic information.

It is another object of the invention to use micropower impulse radar in conjunction with acoustic information for speech coding.

It is another object of the invention to use the methods and apparatus provided for speech coding for the purposes of speech recognition, mathematical approximation, information storage, speech compression, speech synthesis, vocoding, speaker identification, prosthesis, language teaching, speech correction, language identification, and other speech related applications.

The invention is a method and apparatus for joining nonacoustic and acoustic data. Nonacoustic information describing speech organs is obtained using Electromagnetic (EM) waves such as RF waves, microwaves, millimeter waves, infrared or optical waves at wavelengths that reach the speech organs for measurement. Their information is combined with conventional acoustic information measured with a microphone. They are combined, using a deconvolving algorithm, to produce more accurate speech coding than obtainable using only acoustic information. The coded information, representing the speech, is then available for speech technology applications such as speech compression, speech recognition, speaker recognition, speech synthesis, and speech telephony (i.e., vocoding).

Simultaneously obtained EM sensor and acoustic information are used to define a time frame and to obtain the details of a human speaker's excitation function and vocal tract function for each speech time frame. The methods make available the formation of numerical feature vectors for characterizing the acoustic speech unit spoken each speech time frame. This makes possible a new method of speech characterization (i.e., coding) using a more complete and accurate set of information than has been available to previous workers. Such coding can be used for purposes of more accurate and more economical speech recognition, speech compression, speech synthesis, vocoding, speaker identification, teaching, prosthesis, and other applications.

The present invention enables the user to obtain the transfer function of the human speech system for each speech time frame defined using the methods herein. In addition, the present invention includes several algorithmic methods of coding (i.e., numerically describing) these functions for valuable applications in speech recognition, speech synthesis, speaker identification, speech transmission, and many other applications. The coding system, described herein, can make use of much of the apparatus and data collection techniques described in the copending patent application Ser. No. 08/547,596, including EM wave generation, transmission, and detection, as well as data averaging, and data storage algorithms. The procedures defined in the copending patent application are called NASR or Non Acoustic Speech Recognition. Procedures based upon acoustic prior art are called CASR for Conventional Acoustic Speech Recognition, and these procedures are also used herein to provide processed acoustic information.

The following terms are used herein. An acoustic speech unit is the single or multiple sound utterance that is being described, recognized, or synthesized using the methods herein. Examples include syllables, demi-syllables, phonemes, phone-like speech units (i.e., PLUs), diphones, triphones, and more complex sound sequences such as words. Phoneme acoustic-speech-units are used for most of the speech unit examples herein. A speech frame is a time during which speech organ conditions (including repetitive motions of the vocal folds) and the acoustic output remain constant within pre-defined values that define the constancy. Multiple time frames are a sequence of time frames joined together in order to describe changes in acoustic or speech organ conditions as time progresses. A speech period, or pitch period is the time the glottis is open and the time it is closed until the next glottal cycle begins, which include transitions to unvoiced speech or to silence. A speech segment is a period of time of sounded speech that is being processed using the methods herein. Glottal tissue includes vocal fold tissue and surrounding tissue, and glottal open/close cycles are the same as vocal fold open/close cycles. The word functional, as used herein, means a mathematical function with both variables and symbolic parametercoefficients, whereas the word function means a functional with defined numerical parameter-coefficients.

The present methods and apparatus work for all human speech sounds and languages, as well as for animal sounds generated by vocal organ motions detectable by EM sensors and processed as described. The examples are based on, but not limited to American English speech.

1) EM Sensor Generator:

All configurations of EM wave generation and detection modules that meet the requirements for frequency, timing, pulse format, tissue transmission, and power (and safety) can be used. EM wave generators may be used which, when related to the distance from the antenna(s), operate in the EM near-field mode (mostly non-radiating), in the intermediate-EM-field mode where the EM wave is both non-radiating and radiating, and in the radiating far-field mode (i.e. most radars). EM waves in several wavelength-bands between $<10^8$ to $>10^{14}$ Hz can penetrate tissue and be used as described herein. A particular example is a wide-band microwave EM generator impulse radar, radiating 2.5 GHz signals and repeating its measurement at a 2 MHz pulse repetition rate, which penetrates over 10 cm into the head or neck. Such units have been used with appropriate algorithms to validate the methods. These units have been shown to be economical and safe for routine human use. The speech coding experiments have been conducted using EM wave transmit/receive units (i.e., impulse radars) in two different configurations. In one configuration, glottal open-close information, together with simultaneous acoustic speech information, was obtained using one microphone and one radar unit. In a second set of experiments, three EM sensor units and one acoustic unit were used. In addition, a particular method is described for improving the accuracy of transmitting and receiving an electromagnetic wave into the head and neck, for very high accuracy excitation function descriptions.

2) EM Sensor Detector:

Many different EM wave detector modes have been demonstrated for the purpose of obtaining nonacoustic speech organ information. A multiple pulse, fixed-range-gate reception system (i.e., field disturbance mode) has been used for vocal fold motion and nearby tissue motion detection. Other techniques have been used to determine the positions of other vocal organs to obtain added information on the condition of the vocal tract. Many other systems are described in the radar literature on EM wave detection, and can be employed.

3) Configuration structures and Control System:

Many different control techniques for portable and fixed EM sensor/acoustic systems can be used for the purposes of speech coding. However, the processing procedures described herein may require additional and different configurations and control systems. For example, in applications such as high fidelity, "personalized" speech synthesis, extra emphasis must be placed on the quality of the instrumentation, the data collection, and the sound unit parsing. The recording environments, the instrumentation linearity, the dynamic range, the relative timing of the sensors (e.g. acoustic propagation time from the glottis to the microphone), the A/D converter accuracy, the processing algorithms' speed and accuracy, and the qualities of play back instrumentation are all very important.

4) Processing Units and Algorithms:

For each set of received EM signals and acoustic signals there is a need to process and extract the information on organ positions (or motions) and to use the coded speech sounds for the purposes of deconvolving the excitation from the acoustic output, and for tract configuration identification. For example, information on the positions of the vocal folds (and therefore the open area for air flow) vs. time is obtained by measuring the reflected EM waves as a function of time. Similarly, information on the conditions of the lips, jaw, teeth, tongue, and vellum positions can be obtained by transmitting EM waves from other directions and using other pulse formats. The reflected and received signals from the speech organs are stored in a memory and processed every speech time frame, as defined below. The reflected EM signals can be digitized, averaged, and normalized, as a function of time, and feature vectors can be formed.

The present invention uses EM sensor data to automatically define a speech time frame using the number of times that the glottis opens and closes for vocalized speech, while the conditions of other speech organs and the acoustics remain substantially constant. The actual speech time frame interval used for the processing (for either coding or reconstructing) can be adapted to optimize the data processing. The interval can be described by one or several constant single pitch periods, by a single pitch period value and a multiplier describing the number of substantially identical periods over which little sound change occurs, or it can use the pitch periods to describe a time interval of essentially constant speech but with "slowly changing" organ or acoustic conditions. The basic glottal-period timing-unit serves as a master timing clock. The use of glottal periods for master timing makes possible an automated speech and vocal organ information processing system for coding spoken speech, for speech compression, for speaker identification, for obtaining training data, for codebook or library generation, for synchronization with other instruments, and for other applications. This method of speech frame definition is especially useful for defining diphones and higher order multiple sound acoustic speech units, for time compression and alignment, for speaker speech rate normalization, and for prosody parameter definition and implementation. Timing can also be defined for unvoiced speech, similarly to the procedures used for vocalized speech.

Once a speech time frame is defined, the user deconvolves the acoustic excitation function from the acoustic output function. Both are simultaneously measured over the defined time frame. Because the mathematical problems of "invertability" are overcome, much more accurate and efficient coding occurs compared to previous methods. By measuring the human excitation source function in real time, including the time during which the vocal folds are closed and the airflow stops (i.e., the glottal "zeros"), accurate approximations of these very important functional shapes can be employed to model each speech unit. As a result of this new capability to measure the excitation function, the user can employ very accurate, efficient digital signal processing techniques to deconvolve the excitation function from the acoustic speech output function. For the first time, the user is able to accurately and completely describe the human vocal tract transfer function for each speech unit.

There are three speech functions that describe human speech: $E(t)$=excitation function, $H(t)$=transfer function, and $I(t)$=output acoustics function. The user can determine any one of these three speech functions by knowing the two other functions. The human vocal system operates by generating an excitation function, $E(t)$, which produces rapidly pulsating air flow (or air pressure pulses) vs. time. These (acoustic) pulses are convolved with (or filtered by) the vocal tract transfer function, $H(t)$, to obtain a sound output, $I(t)$. Being able to measure, conveniently in real time, the input excitation E and the output I, makes it possible to use linear mathematical processing techniques to deconvolve E from I. This procedure allows the user to obtain an accurate numerical description of the speaker's transfer function H. This method conveniently leads to a numerical Fourier transform of the function H, which is represented as a complex amplitude vs. frequency. A time domain function is also obtainable. These numerical functions for H can be associated with model functions, or can be stored in tabular form, in several ways. The function H is especially useful because it describes, in detail, each speaker's vocal tract acoustical system and it plays a dominant role in defining the individualized speech sounds being spoken.

Secondly, a synthesized output acoustic function, $I(t)$, can be produced by convolving the voiced excitation function, $E(t)$, with the transfer function, $H(t)$, for each desired acoustic speech unit. Thirdly, the excitation function, E, can be determined by deconvolving a previously obtained transfer function, H, from a measured acoustic output function, I. This third method is useful to obtain the modified-white-noise excitation-source spectra to define an excitation function for each type of unvoiced excitation. In addition, these methods can make use of partial knowledge of the functional forms E, H, or I for purposes of increasing the accuracy or speed of operation of the processing steps. For example, the transfer function H is known to contain a term R which describes the lips-to-listener free space acoustic radiation transfer function. This function R can be removed from H leaving a simpler function, H*, which is easier to normalize. Similar knowledge, based on known acoustic physics, and known physiological and mechanical properties of the vocal organs, can be used to constrain or assist in the coding and in specific applications.

The Bases of the Methods:

1) The vocalized excitation function of a speaker and the acoustic output from the speaker are accurately and simultaneously measured using an EM sensor and a microphone. As one important consequence, the natural opening and closing of a speaker's glottis can serve as a master timing clock for the definition of speech time frames.

2) The data from 1) is used to deconvolve the excitation function from the acoustic output and to obtain the speaker's vocal tract transfer function each speech time frame.

3) Once the excitation function, the transfer function, and the acoustic function parameters are determined, the user forms feature vectors that characterize the speech in each time frame of interest to the degree desired.

4) The formation procedures for the feature vectors are valuable and make possible new procedures for more accurate, efficient, and economical speech coding, speech compression, speech recognition, speech synthesis, telephony, speaker identification, and other related applications.

Models and Coding of Human Speech:

It is common practice in acoustic speech technology as well as in many linear system applications to use mathematical models of the system. Such models are used because it is inefficient to retain all of the information measured in a time-evolving (e.g., acoustic) signal, and because they provide a defining constraint (e.g., a pattern or functional form) for simplifying or imposing physical knowledge on the measured data. Users want to employ methods to retain just enough information to meet the needs of their application and to be compatible with the limitations of their processing electronics and software. Models fall into two general categories—linear and non-linear. The methods herein describe a large number of linear models to process both the EM sensor and the acoustic information for purposes of speech coding that have not been available to previous practitioners of speech technology. The methods also include coding using nonlinear models of speech that are quantifiable by table lookup or by curve fitting, by perturbation methods, or using more sophisticated techniques relating an output to an input signal, that also have not been available to users.

The simultaneously obtained acoustic information can also be processed using well known standard acoustic processing techniques. Procedures for forming feature vectors using the processed acoustic information are well known. The resulting feature vector coefficients can be joined with feature vectors coefficients generated by the EM sensor/ acoustic methods described herein.

Vocal system models are generally described by an excitation source which drives an acoustic resonator tract, from whence the sound pressure wave radiates to a listener or to a microphone. There are two major types of speech: 1) voiced where the vocal folds open and close rapidly, at approximately 70 to 200 Hz, providing periodic bursts of air into the vocal tract, and 2) "unvoiced" excitations where constrictions in the vocal tract cause air turbulence and associated modified-white acoustic-noise. (A few sounds are made by both processes at the same time).

The human vocal tract is a complex acoustic-mechanical filter that transforms the excitation (i.e., noise source or air pressure pulses) into recognizable sounds, through mostly linear processes. Physically the human acoustic tract is a series of tubes of different lengths, different area shapes, with side branch resonator structures, nasal passage connections, and both mid and end point constrictions. As the excitation pressure wave proceeds from the excitation source to the mouth (and/or nose), it is constantly being transmitted and reflected by changes in the tract structure, and the output wave that reaches the lips (and nose) is strongly modified by the filtering processes. In addition, the pressure pulses cause the surrounding tissue to vibrate at low levels which affects the sound as well. It is also known that a backward propagating wave (i.e. reflecting wave off of vocal tract transitions) does travel backward toward the vocal folds and the lungs. It is not heard acoustically, but it can influence the glottal system and it does cause vocal tract tissue to vibrate. Such vibrations can be measured by an EM sensor used in a microphone mode.

Researchers at Bell Laboratories (Flanagan, Olive, Sondhi and Schroeter ibid.) and elsewhere have shown that accurate knowledge of the excitation source characteristics and the associated vocal tract configurations can uniquely characterize a given acoustic speech unit such as a syllable, phoneme, or more complex unit. This knowledge can be conveyed by a relatively small set of numbers, which serve as the coefficients of feature vectors that describe the speech unit over each speech time frame. They can be generated to meet the degree of accuracy demanded by the applications. It is also known that if a change in a speech sound occurs, the speaker has moved one or more speech organs to produce the changed sound. The methods described herein can be used to detect such changes, to define a new speech time frame, and to form a new feature vector to describe the new speech conditions.

The methods for obtaining accurate vocal tract transfer function information can be used to define coefficients that can be used in the feature vector that describes the totality of speech tract information for each time frame.

One type of linear model often used to describe the vocal tract transfer function is an acoustic-tube model (see Sondhi and Schroeter, ibid). A user divides up the human vocal tract into a large number of tract segments (e.g., 20) and then, using advanced numerical techniques, the user propagates (numerically) sound waves from an excitation source to the last tract segment (i.e., the output) and obtains an output sound. The computer keeps track of all the reflections, re-reflections, transmissions, resonances, and other propagation features. Experts find the sound to be acceptable, once all of the parameters defining all the segments plus all the excitation parameters are obtained.

While this acoustic tube model has been known for many years, the parameters describing it have been difficult to measure, and essentially impossible to obtain in real time from a given speaker. The methods herein, describing the measuring of the excitation function, the acoustic output, and the deconvolving procedures yields a sufficient number of the parameters needed that the constrictions and conditions of the physical vocal tract structure model can be described each time. One-dimensional numerical procedures, based upon time-series techniques, have been experimentally demonstrated on systems with up to 20 tract segments to produce accurate models for coding and synthesis.

A second type of linear acoustic model for the vocal tract is based upon electrical circuit analogies where excitation sources and transfer functions (with poles and zeros) are commonly used. The corresponding circuit values can be obtained using measured excitation function, output function, and derived transfer-function values. Such circuit analog models range from single mesh circuit analogies, to 20 (or more) mesh circuit models. By defining the model with current representing volume-air-flow (and voltage representing air pressure), then using capacitors to represent acoustic tract-section chamber-volumes, inductors to represent acoustic tract-section air-masses, and resistors to represent acoustic tract-section air-friction and heat loss values, the user is able to model a vocal tract using electrical system techniques. Circuit structures (such as T's and/or Pi's) correspond to the separate structures of the acoustic system, such as tube lengths, tongue positions, and side resonators of a particular individual. In principle, the user chooses the circuit constants and structures to meet the complexity requirements and forms a functional, with unknown parameter values. In practice it has been easy to define circuit analogs, but very difficult to obtain the values describing a given individual and even more difficult to measure them in real time. Using a one mesh model, an electrical analog method has been experimentally validated for obtaining the information needed to determine the feature vector coefficients of a human in real time.

A third important model is based upon time series procedures (a type of digital signal processing) using autoregressive, moving average (ARMA) techniques. This approach is especially valuable because it characterizes the behavior of a wave as it traverses a series of transitions in the propagating media. The degree of the ARMA functional reflects the number of transitions (i.e., constrictions and other changes) in acoustic tracts used in the model of the individual. Such a model is also very valuable because it allows the incorporation of several types of excitation sources, the reaction of the propagating waves on the vocal tract tissue media itself, and the feedback by backward propagating wave to the excitation functions. The use of ARMA models has been validated using 14 zeros and 10 poles to form the feature vector for the vocal tract transfer function of a speaker saying the phoneme /ah/ as well as other sounds.

A fourth method is to use generalized curve fitting procedures to fit data in tables of the measured excitation-function and acoustic-output processed values. The process of curve fitting (e.g., using polynomials, LPC procedures, or other numerical approximations) is to use functional forms that are computationally well known and that use a limited number of parameters to produce an acceptable fit to the processed numerical data. Sometimes the functional forms include partial physical knowledge. These procedures can be used to measure and quantify arbitrary linear as well as non-linear properties relating the output to the input.

5) Speech Coding System and Post Processing Units:

The following devices can be used as part of a speech coding system or all together for a variety of user chosen speech related applications. All of the following devices, except generic peripherals, are specifically designed to make use of the present methods and will not operate at full capability without these methods.

a) Telephone receiver/transmitter unit with EM sensors: A unit, chosen for the application, contains the needed EM sensors, microphone, speaker, and controls for the application at hand. The internal components of such a telephone-like unit can include one or more EM sensors, a processing unit, a control unit, a synthesis unit, and a wireless transmission unit. This unit can be connected to a more complex system using wireless or transmission line techniques.

b) Control Unit: A specific device that carries out the control intentions of the user by directing the specific processors to work in a defined way, it directs the information to the specified processors, it stores the processed data as directed in short or long term memory, it can transmit the data to another specified device for special processing, to display units, or to a communications devices as directed.

c) Speech Coding Unit: A specific type of a coding processor joins information from an acoustic sensor to vocal organ information from the EM sensor system (e.g., from vocal fold motions) to generate a series of coefficients that are formed into a feature vector for each speech time frame. The algorithms to accomplish these actions are contained therein.

d) Speech Recognizer: Post processing units are used to identify the feature vectors formed by the speech coding unit for speech recognition applications. The speech recognition unit matches the feature vector from c) with those in a pre-constructed library. The other post-processing units associated with recognition (e.g., spell checkers, grammar checkers, and syntax checkers) are commonly needed for the speech coding applications.

e) Speech Synthesizer and Speaker: Coded speech can be synthesized into audio acoustic output. Information, thus coded, can be retrieved from the user's recent speech, from symbolic information (e.g., ASCII symbol codes) that is converted into acoustic output, from information transmitted from other systems, and from system communications with users. Furthermore, the coded speech can be altered and synthesized into many voices or languages.

f) Speaker Identification: As part of the post processing, the idiosyncratic speech and organ motion characteristics of each speaker can be analyzed and compared in real time. The comparison is to known records of the speaker's physical speech organ motions, shapes, and language usage properties for a sequence of words. The EM sensor information adds a new dimension of sophistication in the identification process that is not possible using acoustic speech alone.

g) Encryption Units: Speech coded by the procedures herein can be further coded (i.e., encrypted) in various ways to make them difficult to use by other than an authorized user. The methods described herein allow the user to code speech, with such a low bandwidth requirement, that encryption information can be added to the transmitted speech signal without requiring additional bandwidth beyond what is normally used.

h) Display Units: Computer rendered speech information must be made available to the user for a variety of applications. A video terminal is used to show the written word rendition of the spoken words, graphical renditions of the information, (e.g., the articulators in a vocal tract), a speaker is used to play previously recorded and coded speech to the user. The information can be displayed by printed using printers or fax machines.

i) Hand Control Units: Hand control units can assist in the instruction of the system being spoken to. The advantage of a hand control unit (similar to a "mouse") is that it can assist in communicating or correcting the type of speech being inputted. Examples are to distinguish control instructions from data inputting, to assist in editing by directing a combined speech-hand-directed cursor to increase the speed of identifying displayed text segments, to increase the certainty of control by the user, to elicit play-back of desired synthesized phrases, to request vocal tract pictures of the speakers articulator positions for language correction, etc.

j) Language Recognizer and Translator Unit: As the speaker begins to talk into a microphone, this device codes the speech and characterizes the measured series of phonemes as to the language to which they belong. The system can request the user to pronounce known words which are identified, or the system can use statistics of frequent word sound patterns to conduct a statistical search through the codebooks for each language.

It is also convenient to use this same unit, and the procedures described herein, to accept speech recognized words from one language and to translate the symbols for the same words into the speech synthesis codes for the second language. The user may implement control commands requesting the speaker to identify the languages to be used. Alternatively, the automatic language identification unit, can use the statistics of the language, to identify the languages from which and to which the translations are to take place. The translator then performs the translation to the second desired language, by using the speech unit codes, and associated speech unit symbols, that the system generates while the first language is spoken. The speech codes, generated by the translator, are then converted into symbols or into synthesized speech in the desired second language.

k) Peripheral Units: Many peripheral units can be attached to the system as needed by the user making possible new capabilities. As an example, an auxiliary instrument interface unit allows the connection of instruments, such as a video camera, that require synchronization with the acoustic speech and speech coding. A communications link is very useful because it provides wireless or transmission line interfacing and communication with other systems. A keyboard is used to interface with the system in a conventional way, but also to direct speech technology procedures. Storage units such as disks, tape drives, semiconductor memories are used to hold processed results or, during processing, for temporary storage of information needed.

BRIEF DESCRIPTION OF THE DRAWINGS

FIG. 12A shows a feature vector for the phoneme /ah/.

FIG. 12B shows the ARMA poles and zeros for FIG. 9A.

FIG. 12C shows the corresponding ARMA "a"'s and "b"'s for the sound /ah/ represented in FIG. 11A.

DETAILED DESCRIPTION OF THE PREFERRED EMBODIMENT

General Principles

Figure 1:
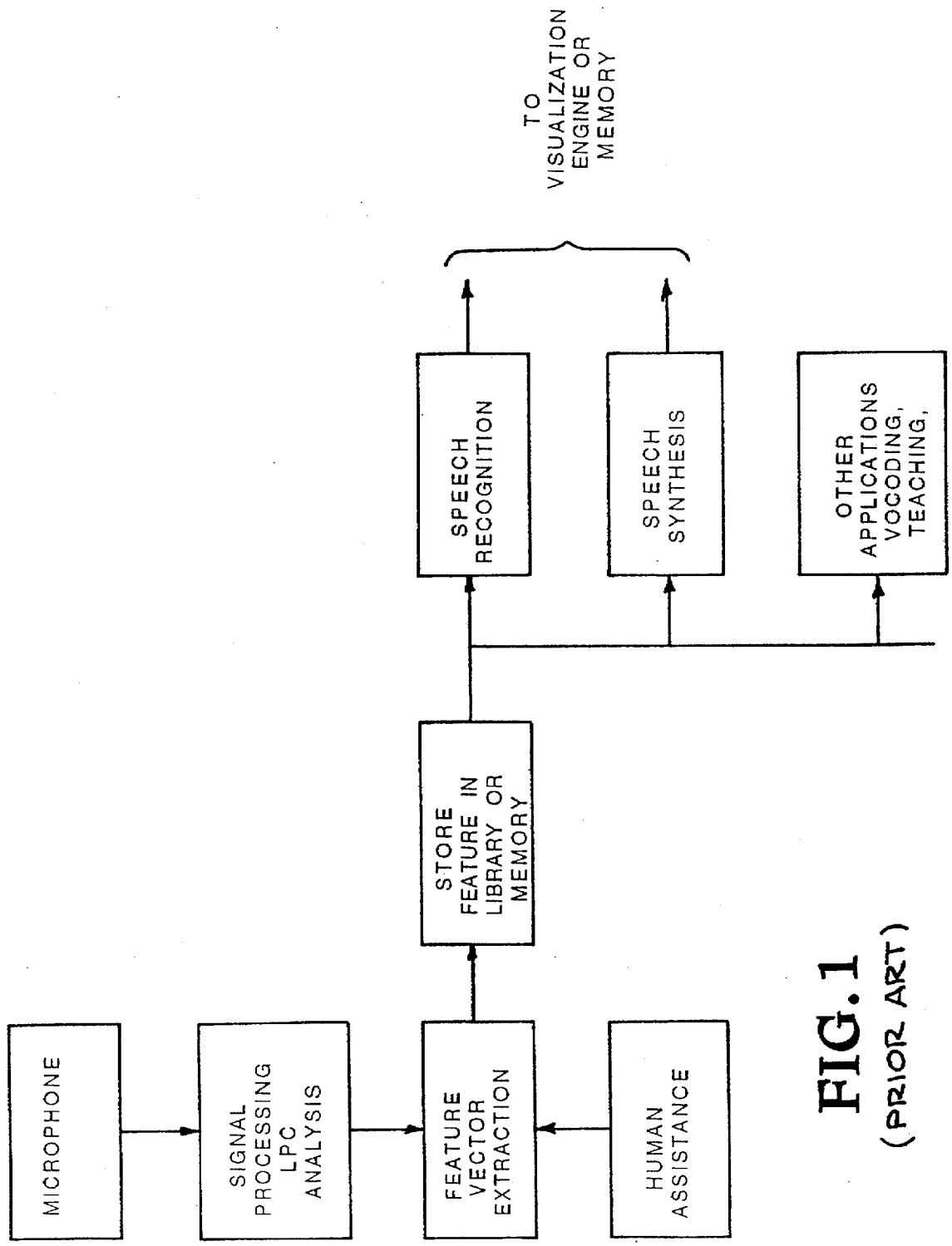
FIG. 1 is a schematic diagram of a prior art open loop acoustic speech coding system.
Figure 2:
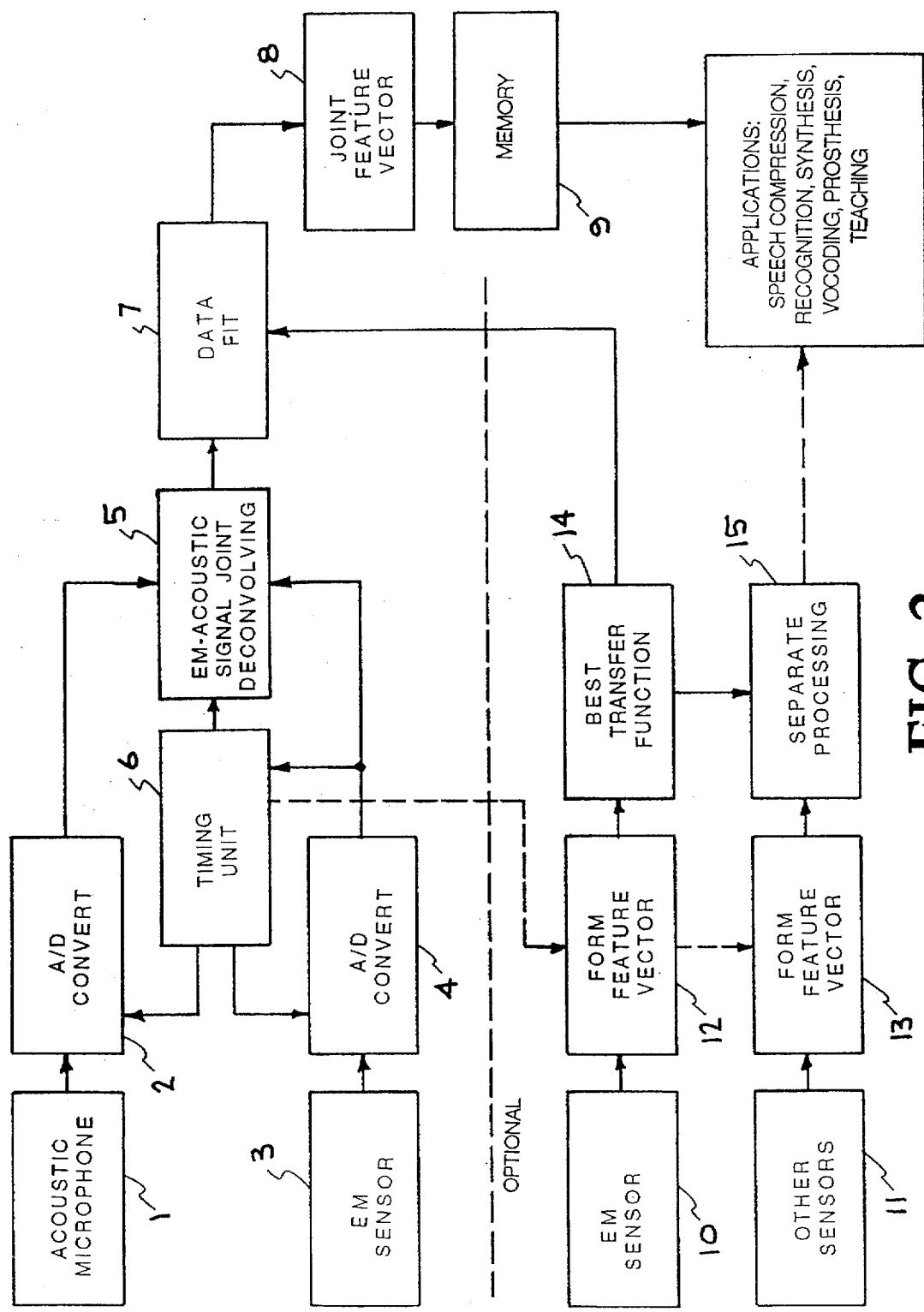
FIG. 2 is a schematic diagram of a combined nonacoustic/ acoustic speech coding system using an EM sensor and a microphone, including optional auxiliary instruments.

FIG. 2 shows a speech processing model based on an EM sensor that is used to measure the motions of vocal fold interfaces and glottal tissue. These motions can be related to the volume air flow or glottal pressure, and can be measured simultaneously with the accompanying speech. Knowledge of the voiced excitation input and the acoustic output of a human vocal tract provides sufficient information to accurately deconvolve the excitation from the output. The information from the sensors and from the deconvolving process makes possible new methods to code human speech in real time, and in an economical, safe, convenient, and accurate manner.

In FIG. 2, signals from an acoustic microphone 1 are processed in block 2 where the acoustic signals are digitized and feature vectors are formed for selected time frames. Electromagnetic signals from EM vocal fold sensor 3 are input into processing block 4 where the signals are digitized and time units are defined and feature vectors are formed. The acoustic and EM feature vectors from processing blocks 2 and 4 are input into processing block 5 where the EM signal is deconvolved from the acoustic signal. Processing unit 4 also controls timing unit 6, which sets the master timing and speech time frames, and which is connected back to processing units 2 and 4. The deconvolved output from unit 5 is input into unit 7 where the data is fit to a transfer function, which is used to form a joint feature vector in unit 8, which is then stored in a memory or code book in block 9. Optionally, additional EM sensors 10 can be used to measure vocal tract conditions and other sensors 11 can also be utilized. Feature vectors from sensors 10, 11 are formed in blocks 12, 13 and the best transfer function for deconvollution is selected in block 14, which is then input into unit 7. In addition, feature vectors from block 2 can be sent directly to a CASR (conventional acoustic recognition system), and feature vectors from blocks 12,13 can be sent via block 15 for separate processing and subsequent use in the applications described herein.

Figure 3A:
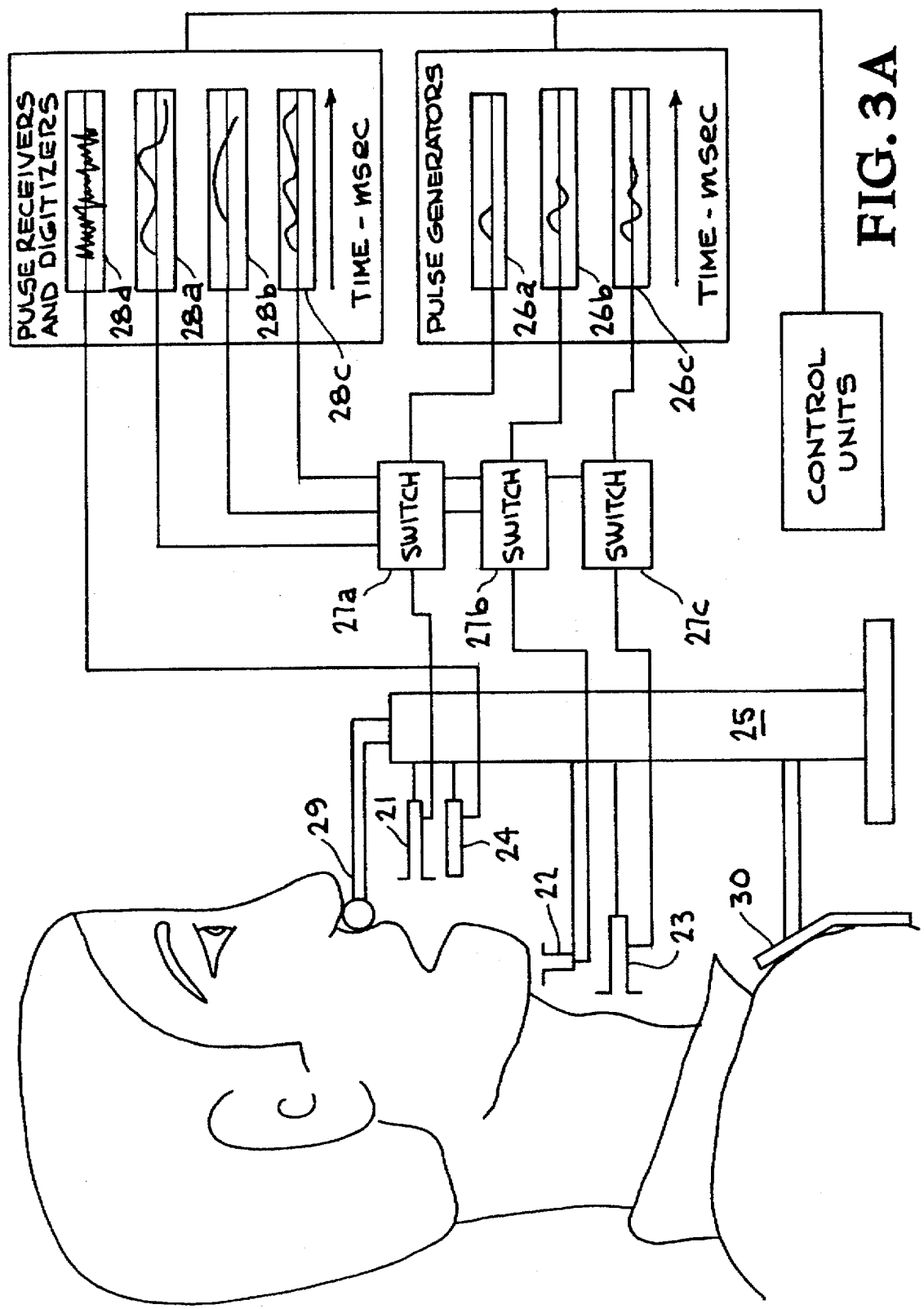
FIG. 3A shows a schematic diagram of a highly accurate and flexible vocal tract laboratory measuring system for speech coding.
Figure 3B:
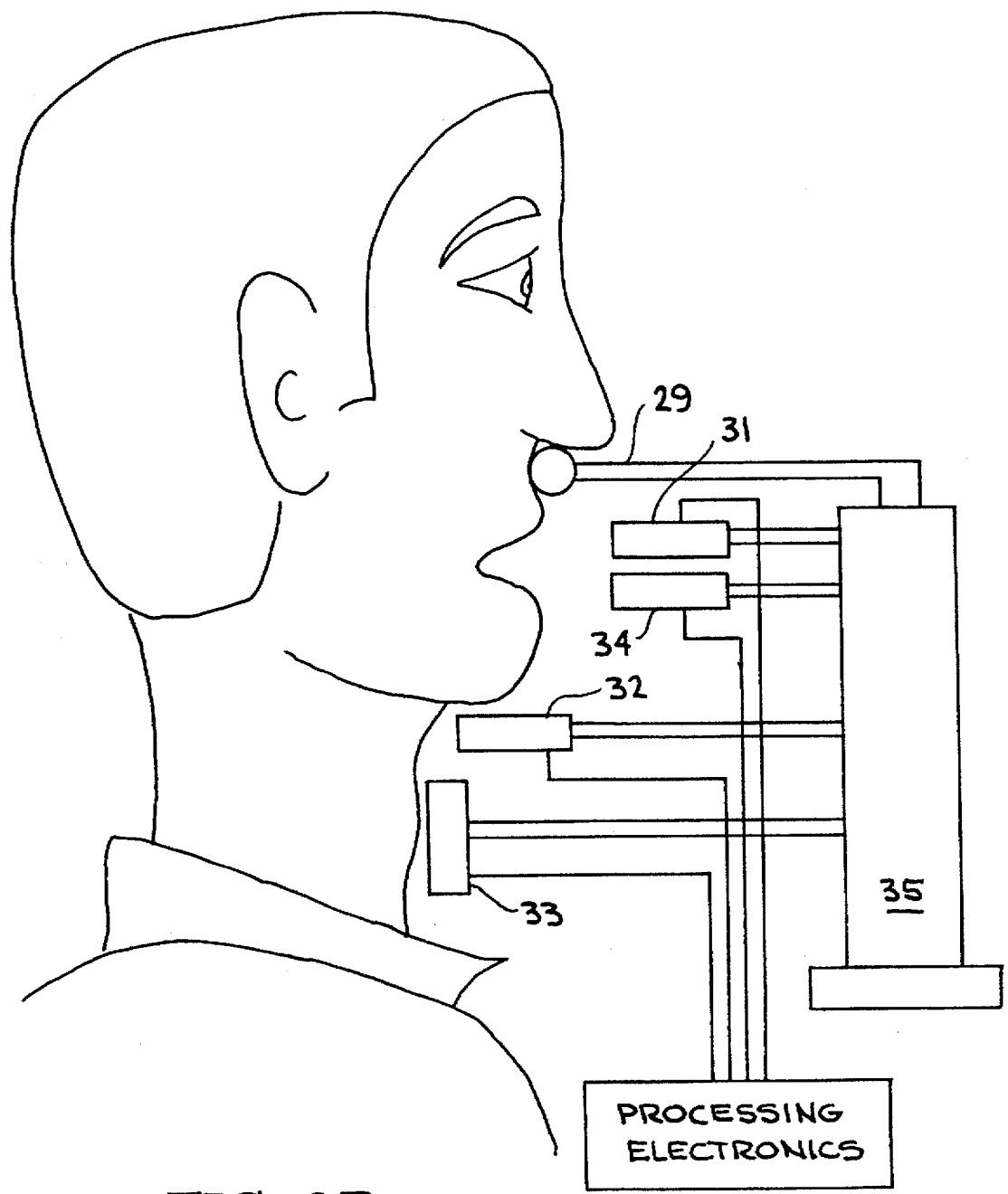
FIG. 3B shows a system for speech coding using three micropower radars and an acoustic microphone.

FIGS. 3A and FIG. 3B show two types of laboratory apparatus for measuring the simultaneous properties of several speech organs using EM sensors and for obtaining simultaneous acoustic information. FIG. 3A, in particular, shows highly accurate laboratory instrumentation assembled to obtain very high fidelity, linear, and very large dynamic range information on the vocal system during each speech time frame. FIG. 3A shows a view of a head with three antennas 21, 22, 23 and an acoustic microphone 24 mounted on a support stand 25. Antennas 21, 22, 23 are connected to pulse generators 26a, b, c through transmit/receiver switches 27a, b, c respectively. Pulse generators 26a, b, c apply pulses to antennas 21, 22, 23, which are directed to various parts of the vocal system. Antennas 21, 22, 23 pick up reflected pulses, which are then transmitted back through switches 27a, b, c to pulse receivers and digitizers (e.g., sample and hold units) 28a, b, c. Acoustic information from microphone 24 is also input into pulse receiver and digitizer 28d. Support stand 25 positions the antennas 21, 22, 23 to detect signals from various parts of the vocal tract, e.g., by using face positioning structure 29 and chest positioning structure 30. As shown, antenna 21 is positioned to detect the tongue, lip, velum, etc. Antenna 22 is positioned to detect tongue and jaw motion and antenna 23 is position to detect vocal fold motion.

FIG. 3B shows how presently available micro-impulse radars have been used to obtain valuable speech organ information in a controlled setting. The EM sensor signals from these EM sensors, measuring vocal fold or other tissue motion, are related to the true voiced excitation signal (i.e. volume air flow vs. time or pressure versus time) using the methods herein. FIG. 3B shows a view of a head with three EM sensor transmit/receive modules 31, 32, 33 and an acoustic microphone 34 mounted on a support stand 35. The configuration is similar to that in FIG. 3A except that entire EM motion sensors 31, 32, 33 are mounted on the stand 35 instead of just antennas with the remaining associated electronics being mounted in a remote rack. Many experiments referenced in this patent application were conducting using apparatus similar to that shown in FIG. 3B.

Figure 4:
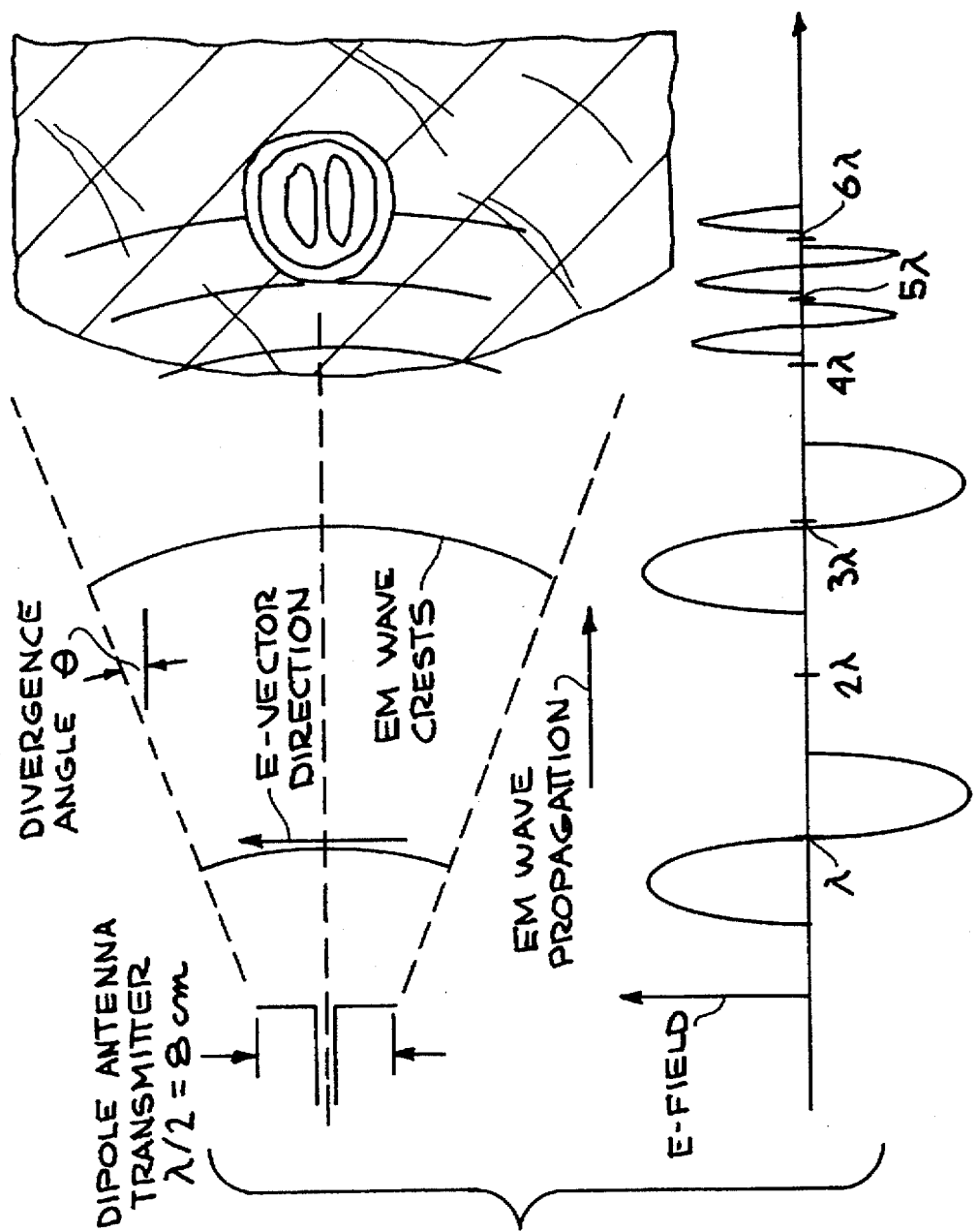
FIG. 4 shows an EM sensor directing EM radiation into the neck of a speaker with vocal folds shown in an open condition.

FIG. 4 shows how an EM wave from an electromagnetic wave generator is used to measure the conditions of the vocal folds in a human speaker's neck. The wave is shown as radiated from the antenna; however other measuring arrangements can use an EM wave in the near field or in the intermediate field, in addition to the far field radiated EM wave as used in most radars. The EM wave is generated to measure the conditions of the vocal folds and the glottal tissue surrounding the vocal fold structure as often and as accurately as needed for the accuracy of the application.

Figure 5:
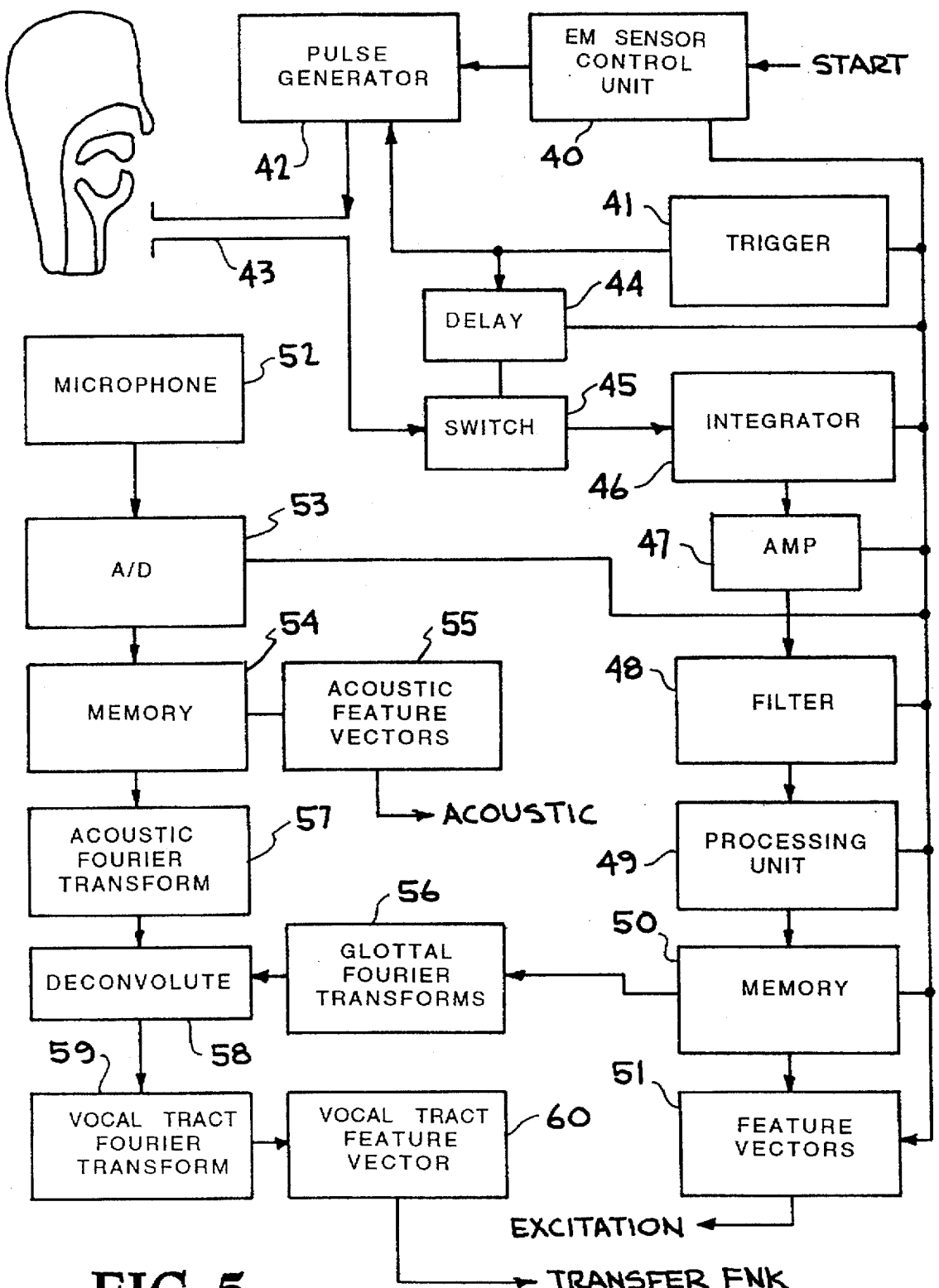
FIG. 5 is a flow chart showing the processing of simultaneously recorded acoustic data and EM sensor data, and subsequent deconvolution.

FIG. 5 shows a system in which knowledge of the vocalized excitation function is used to deconvolve the speech vocal tract transfer function information from measured acoustic speech output each time frame. All of the information gathered during each speech time frame, including acoustics, EM sensor information, and deconvolved transfer function information, can be processed, normalized, quantized, and stored (along with control information) in a feature vector representing the speaker's voice during one or more speech time frames. Similar deconvolving procedures are used with unvoiced excitation functions. As shown in FIG. 5, an EM sensor control unit 40 drives a repetition rate trigger 41, which drives pulse generator 42, which transmits one or more pulses from antenna 43. EM sensor control unit 40 sets the pulse format, time frame interval, integration times, memory locations, function forms, and controls and initializes pulse generator 42. Control unit 40 and trigger 41 also actuate switch 45 through delay 44 to range gate received pulses. Antenna 43 is positioned to direct transmitted pulses towards the vocal organs and receive pulses reflected therefrom. The received pulses pass through switch 45 and are integrated by integrator 46, then amplified by amplifier 47, and passed through a high pass filter 48 to a processing unit 49. Processing unit 49 contains an AD converter for digitizing the EM signals and also includes zero location detector, memory detector, and obtains glottal area versus time. The digitized and processed data from unit 49 is stored in memory bins 50, from which excitation function feature vectors are formed in block 51. Simultaneously, signals from an acoustic microphone 52 are digitized by AD converter 53, which is also controlled and synchronized by EM sensor control unit 40. The digitized data from AD converter 53 is stored in memory bins 54 from which acoustic feature vectors are formed in block 55. The digitized vocal fold data from memory bins 50 is used to produce a glottal Fourier transform 56, while the digitized acoustic data in memory bin 54 is used to produce an acoustic Fourier transform 57. The two Fourier transforms 56, 57 are deconvolved in block 58 to produce a vocal tract Fourier transform 59 which is then fit to a prechosen functional form to form a vocal tract feature vector in block 60.

Figure 6:
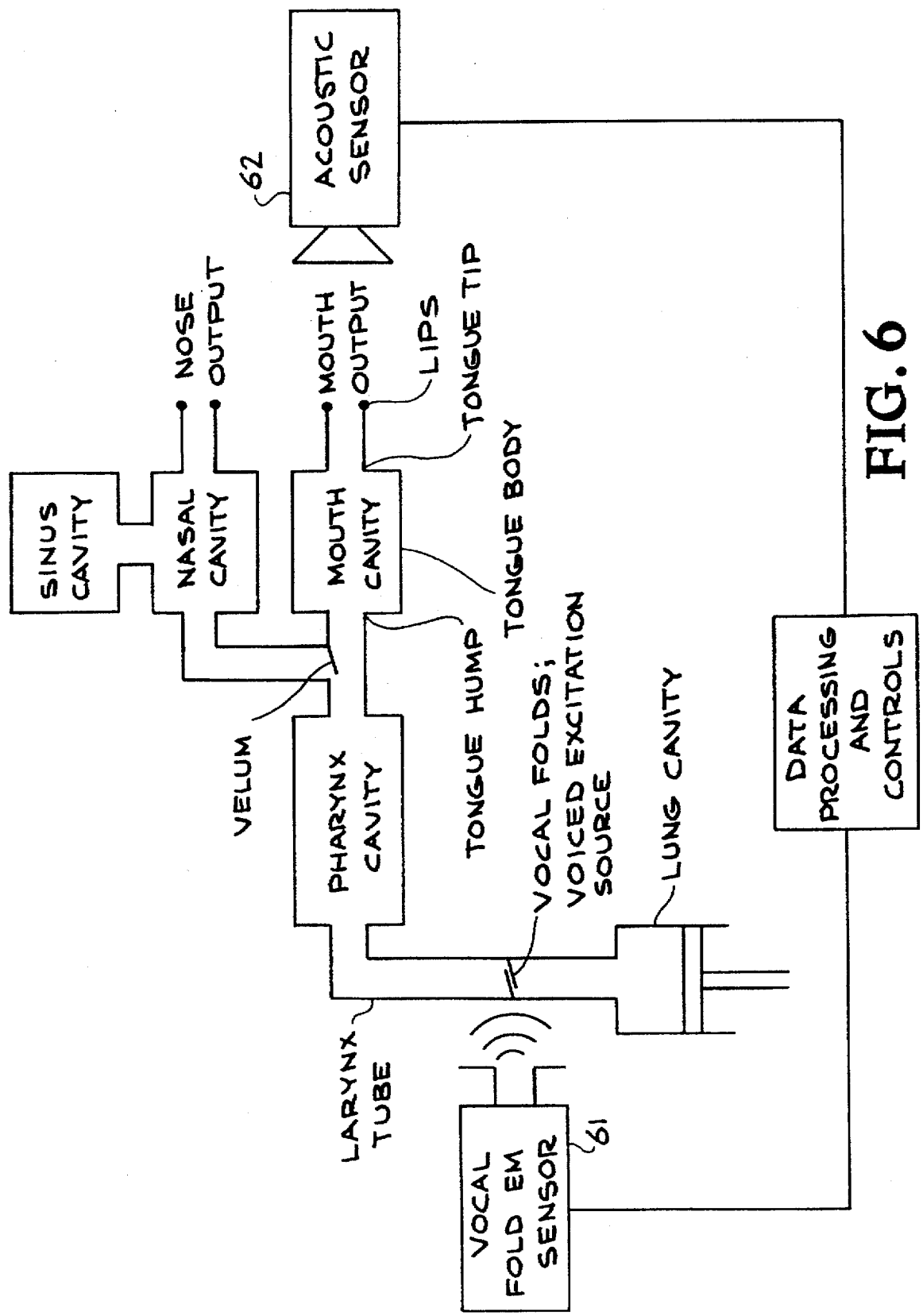
FIG. 6 is an acoustic and air flow model of vocal system showing an EM sensor for vocal folds and a microphone acoustic detector.

FIG. 6 shows a schematic of the human vocal system from an acoustic perspective. FIG. 6 also identifies the major components utilized in speech, with an EM sensor 61 positioned to detect glottal motions including those of the vocal folds) which form an excitation source for the vocal tract, and an acoustic sensor 62 positioned to receive acoustic output from the mouth. The physical behavior of acoustic excitation pulses, after they are generated by the vocal folds or after generation at air passage constrictions, and as they traverse and are filtered by the varying tubes and chambers, are measured as acoustic pressure waves by the acoustic sensor (e.g., a microphone). Procedures described herein show how to describe the consequences of all of the important vocal tract structures, how to determine when they change to form a new sound, and how to code such condition for subsequent applications. The condition of the human speech organ structure is known to provide sufficient information to identify the acoustic speech units being articulated by that structure. In addition, it is known that these structures vary from individual to individual, and the way they are shaped and moved to articulate a sequential series of acoustic speech units varies from language to language and from individual to individual. Knowledge of such individual structural patterns, and their time sequencing to form speech sounds, forms the basis for speaker identification and language identification.

Figure 7:
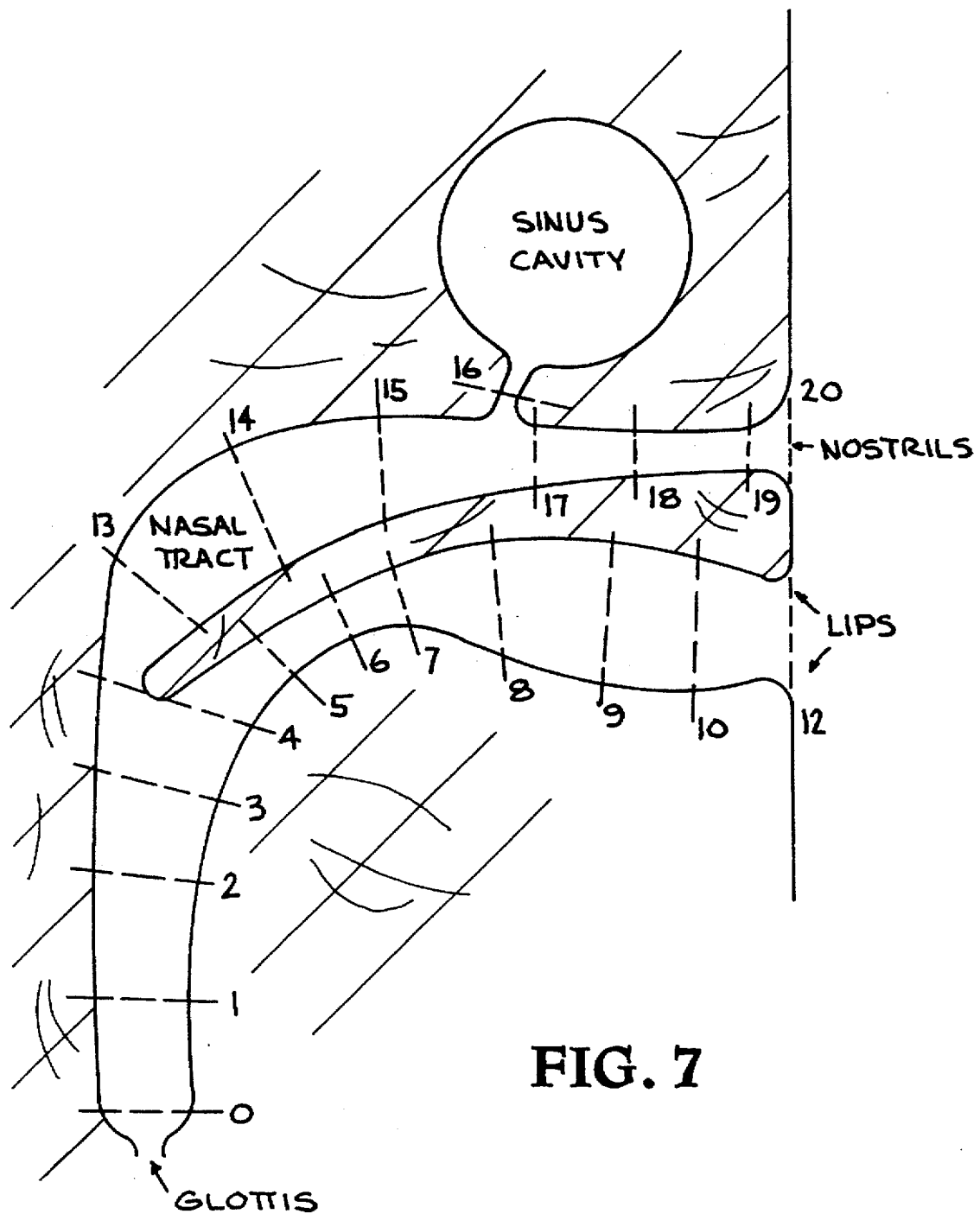
FIG. 7 is a continuous model of the vocal tract divided into 20 segments.

FIG. 7 is a sketch of a cut through a human vocal system showing transverse dimensions along the center plane. The dotted lines and numbers show where one might approximate the vocal tract by short approximately circular cylinder constant sections. At each dotted interface, the cylinder would change diameter and, thus, a propagating acoustic wave from the glottis to the lips and/or nose would be both transmitted and reflected. In human vocal systems a cross section is not circular and the transitions are smooth. By segmenting this structure into a sufficient number of substructures (e.g., 20), each having a small dimensional change from the neighbors, accurate descriptions of the air flow (and pressure) can be obtained. Well known numerical and/or time series (e.g., ARMA) techniques have been used to describe the acoustic wave as it propagates from the excitation source to the microphone (or human ear) detector. Time series analysis (e.g. Z transform) procedures are especially useful for characterizing such systems, because their functional forms easily accommodate a series of reflecting and transmitting structures. They are used herein to describe many of the transfer function examples.

Figure 8:
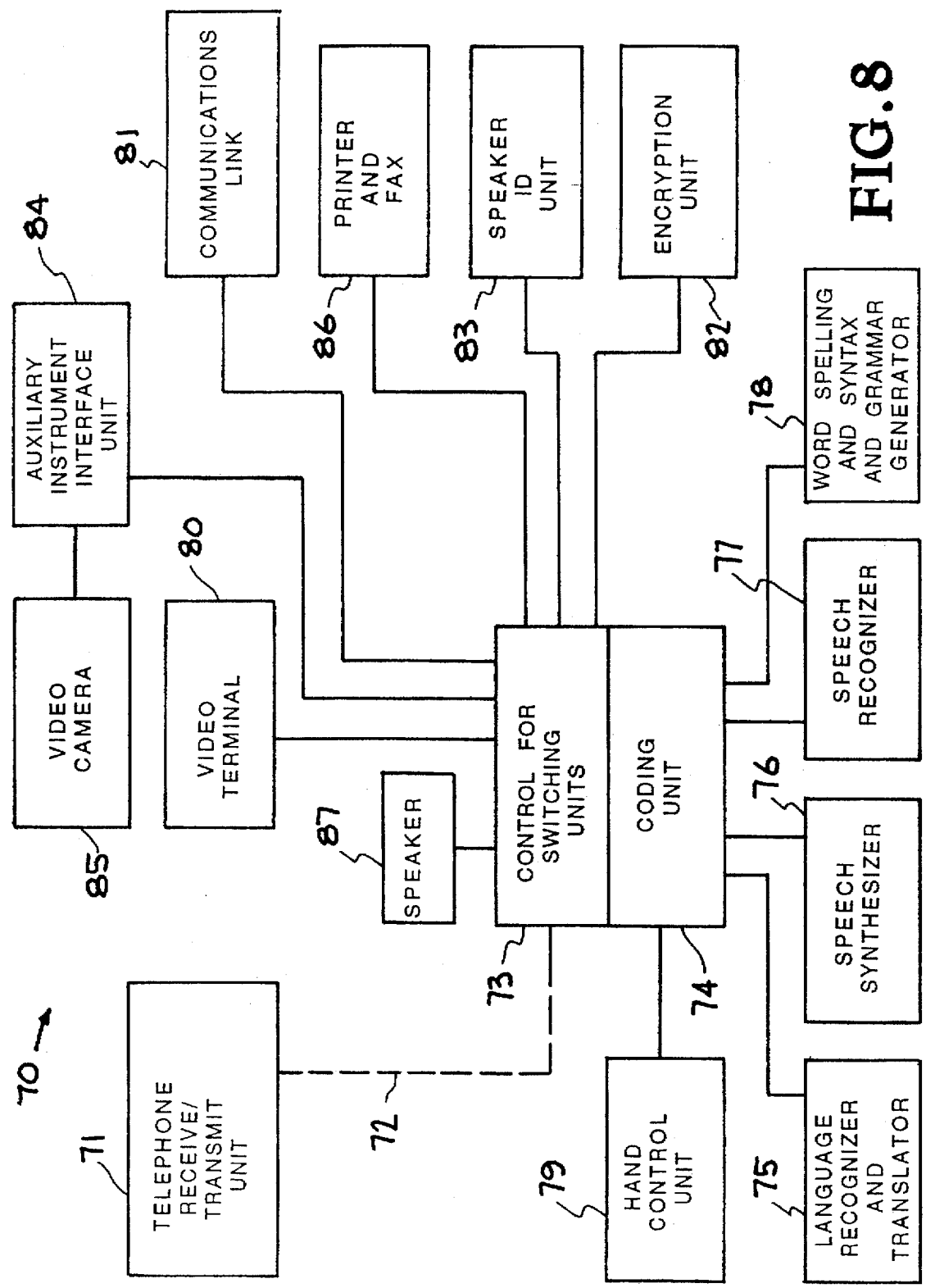
FIG. 8 is a schematic diagram of a speech coding system using EM sensors and acoustic data.

FIG. 8 schematically illustrates a speech technology system 70 using sensor 71, which includes both EM sensors and acoustic detectors. Sensor 71 could be, for example, similar to the device shown in FIG. 3B or built into a telephone receive/transmit unit as in FIG. 20. Sensor 71 is connected by a wireless (RF or optical) link or cable communication line 72 to a coding unit 74, which has associated therewith a control unit 73. Coding unit 74 is connected to language recognizer and translator 75, speech synthesizer 76, speech recognizer 77, and word spelling/syntax/grammar generator 78. A hand control unit 79 is connected to coding unit 74. Control unit 73 is connected to coding unit 74 for switching units and for directing information flow. Other peripheral equipment can be connected to coding unit 74 through control unit 73. For example, a video terminal 80, a communications link 81 to wires, cellular, wireless, fiber optics, etc., an encryption unit 82, a speaker identification unit 83, an auxiliary instrument interface unit 84 with a video camera 85 connected thereto, a printer or fax 86, or a loud speaker 87 can all be connected to control unit 73. Such a system makes it possible to record and process speech information, to code the information, and to use this coded information for applications such as forming language codebooks, speech recognition, speech synthesis, speaker identification, vocoding, language identification, simultaneous translation, synchronization of speech with video systems and other instruments, low bandwidth coding and encryption, speech correction and prosthesis, and language learning.

Figure 20:
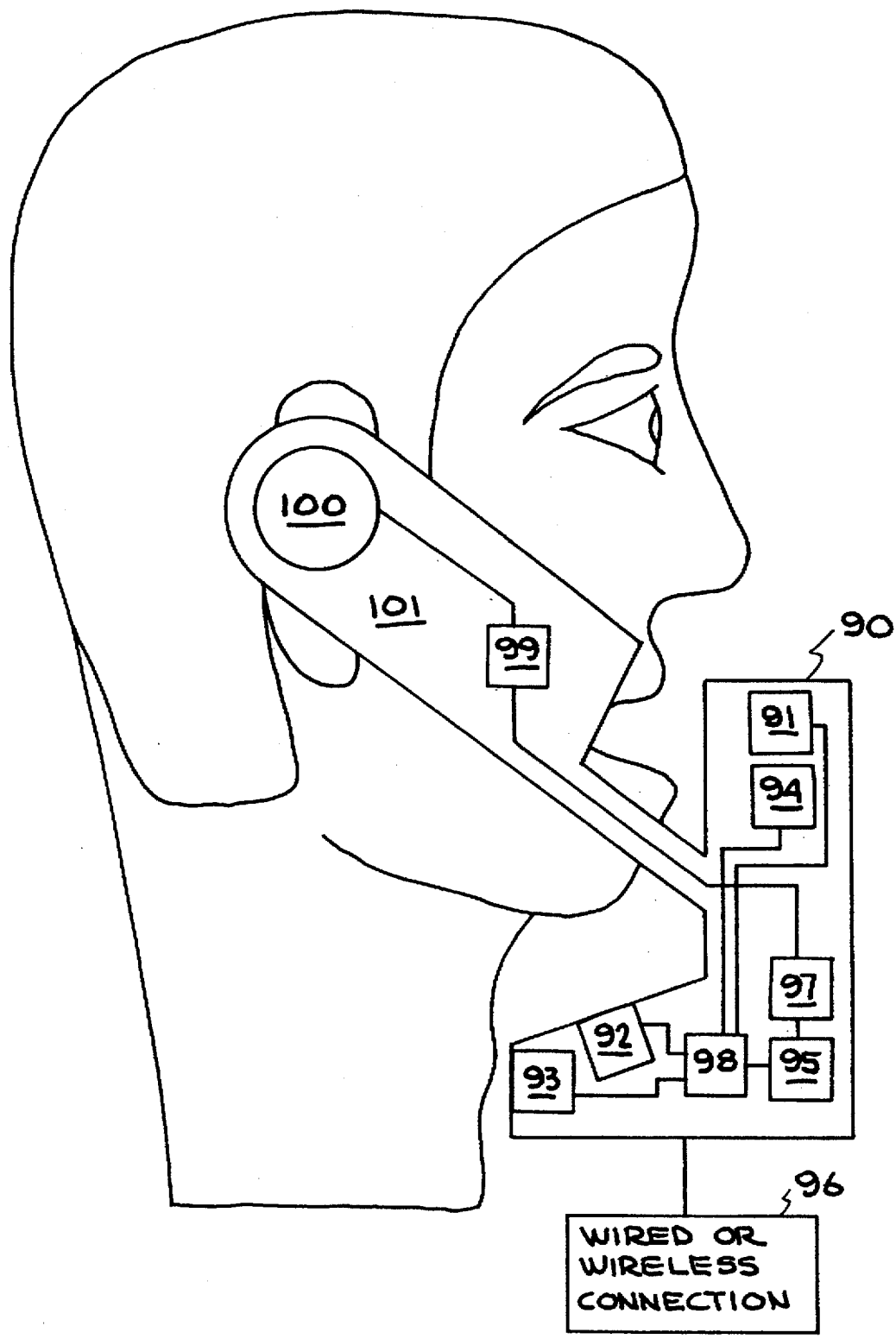
FIG. 20 shows a telephone hand-set vocoding apparatus with receiver-speaker and microphone, including EM sensors for coding, and a synthesizer for decoding.

The system represented in FIG. 8 can be simplified and miniaturized for special applications. For example, FIG. 20 shows a portable, specialized version for vocoding because it obtains EM sensor plus acoustic information, processes it, codes it, and sends it into a transmission system that carries the information to a similar handheld unit for decoding and synthesizing of speech for the listener.

Figure 9A:
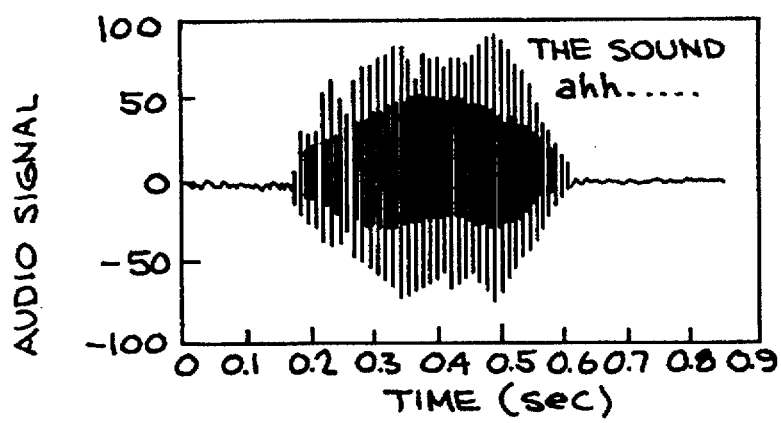
FIGS. 9A,B are time domain data for the speech sound /ah/ using an acoustic pressure sensor and an EM glottal tissue sensor.
Figure 10A:
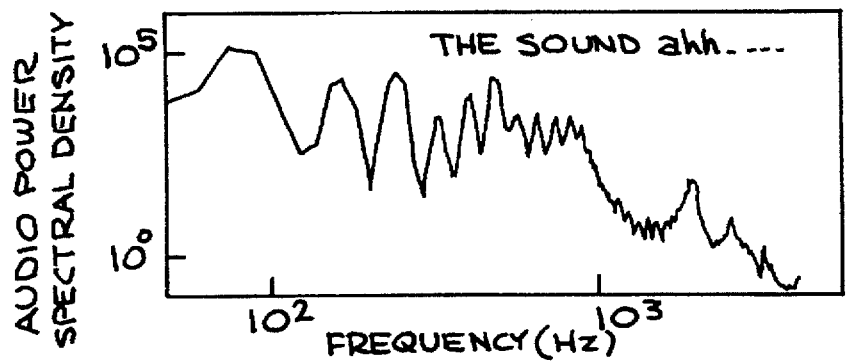
FIGS. 10A,B are Fourier power spectra for the acoustic microphone data and the EM sensor measurements of glottal cycles for the sound /ah/.
Figure 11:
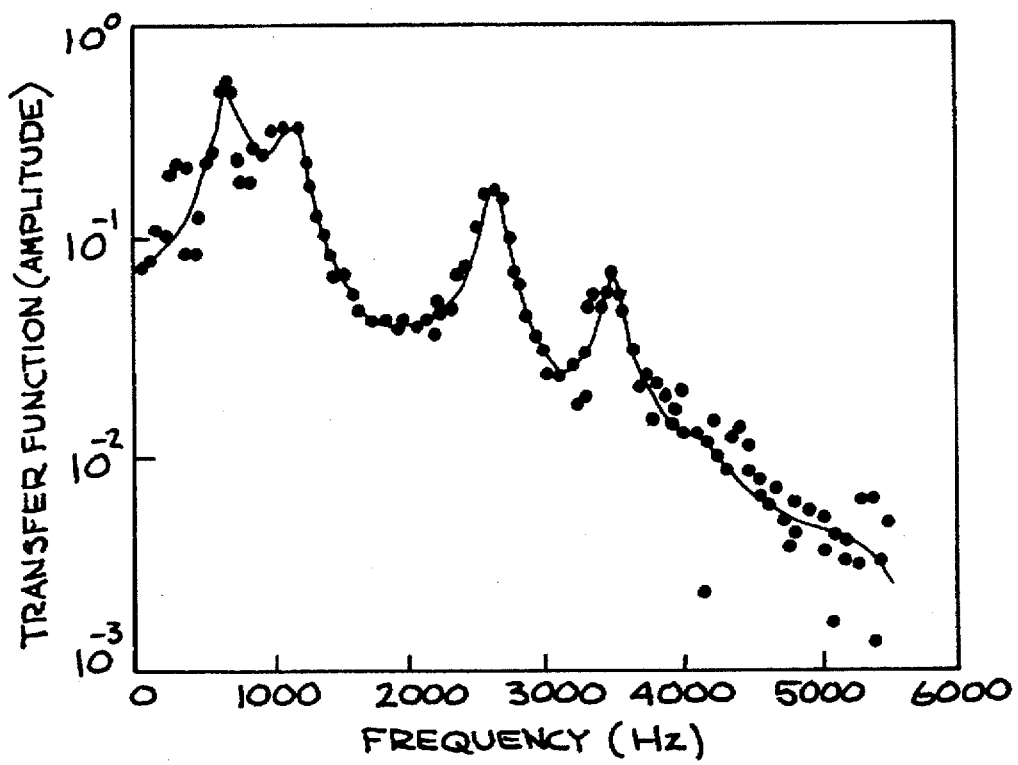
FIG. 11A shows Fourier transfer function amplitude coefficients obtained for the two-tube phoneme /ah/.
FIG. 11B shows Fourier transfer function amplitude coefficients obtained for the single tube phoneme /ae/.
Figure 11:
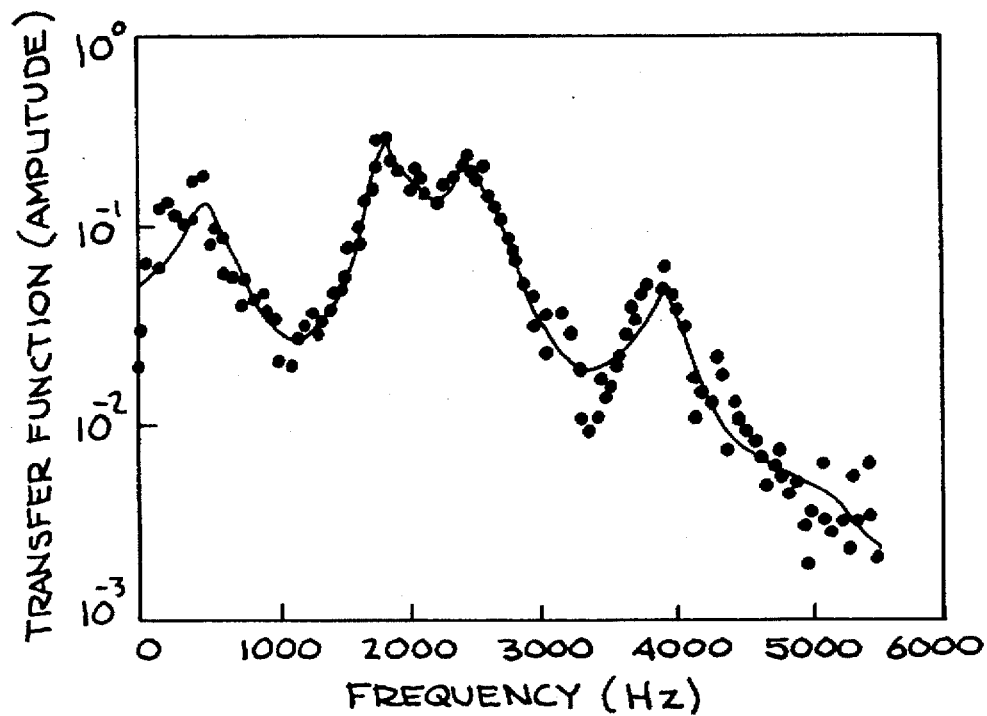
Figure 13C:
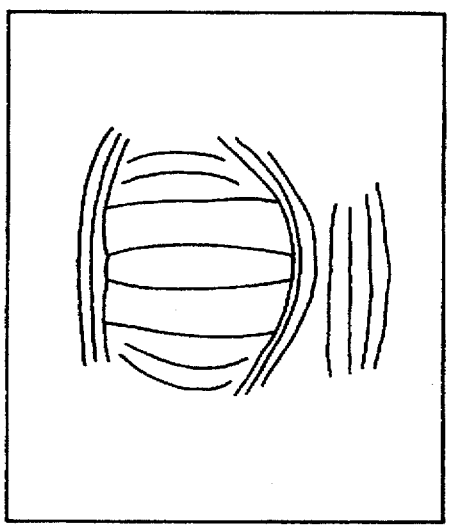
FIGS. 13A–F show images of vocal folds opening and closing during one speech frame period, and characteristic dimensions.
Figure 13F:
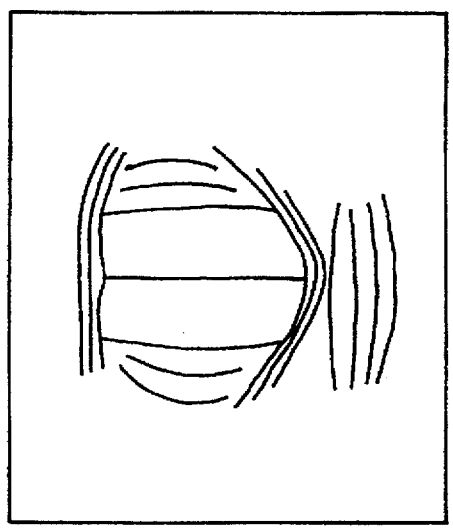
Figure 13B:
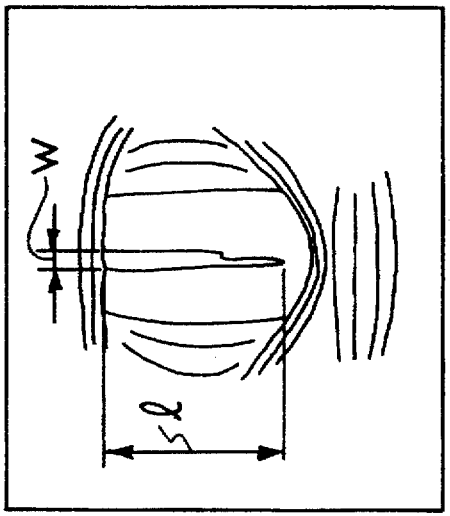
Figure 13E:
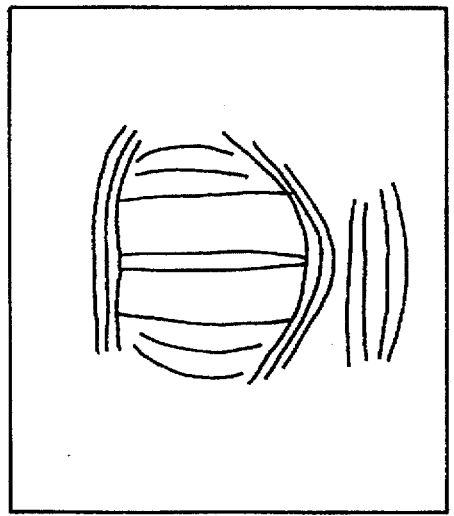
Figure 13A:
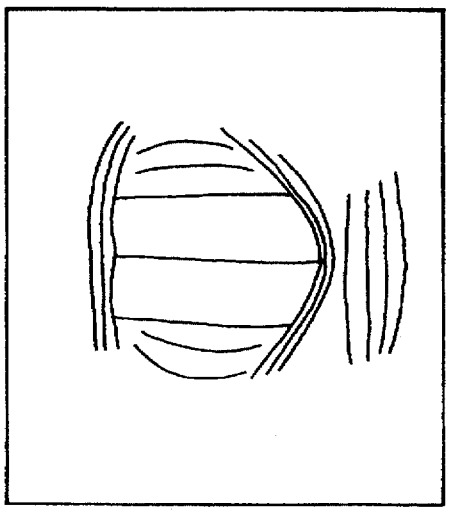
Figure 13D:
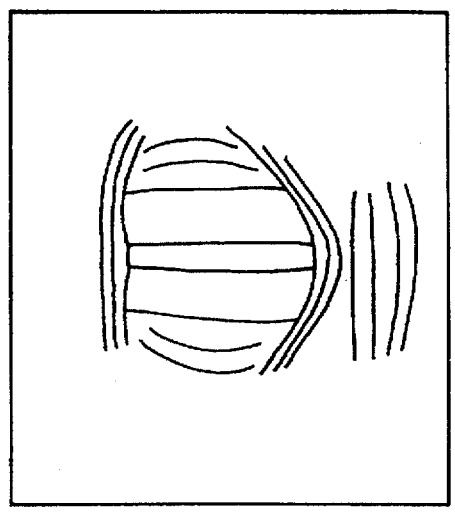

Deconvolving the Vocal System Excitation Function:

This method has been demonstrated using the EM glottal opening (i.e., vocal fold) area information and acoustic information measured for one or several sequential speech time frame periods to deconvolve the vocal system volume air flow source function from the measured acoustic speech output from a human speaker. FIGS. 9A,B show raw acoustic microphone and glottal motion data. The Fourier transforms of the data can be obtained and are shown in FIGS. 10A,B. The numerical representations of these two functions allow the user to obtain a numerical representation (i.e., a complex number coefficient representation) of the transfer function representing the acoustic filtering of the human vocal tract during the time frame or frames. The deconvolving of the excitation function from the acoustic output can be accomplished using real time techniques, time series techniques, fast Fourier transform techniques, model based transform techniques, and other techniques well known to experts in the field of data processing and deconvolving. Examples are shown whereby the Fourier transform of the acoustic output is divided by the excitation function input. FIG. 11A shows the two tube sound /ah/ derived by using inputs from FIGS. 9A,B and 10A, B. FIG. 11B shows the transfer function for the single tube sound /ae/ 20 which is deconvolved using acoustic and vocal fold data similar to that for the two tube sound /ah/.

By using other EM sensors (in addition to the glottal sensor) to determine other speech organ location information, with or without simultaneous acoustic data, one can determine the optimal transfer functional structure to use for best convergence or for most accurate fitting of the transfer function. (Herein, functional is used to mean a specific function form, but with unspecified constants). An example is to use a lip sensor to report that when the lips are closed, during the articulation of a nasal phoneme /m/, the transfer functional form must contain a spectral zero due to the closed mouth cavity.

An example is to choose an ARMA functional (i.e. time series) description, with an appropriate number of poles and zeros, for each speech time interval frame. The number of poles and zeros are chosen to represent the complexity of the model and the desired accuracy of the resultant coding.

I(t), and E(t) are the measured acoustic output and EM excitation respectively. The algebraic input/output relation using the transfer function H(z) in the z-transform variable is:

$$I(z) = H(z) * E(z)$$

where H(z) is given in factored, pole-zero form, by:

$$H(z) = \frac{(z-z_1)(z-z_2)(z-z_3)\ldots(z-z_m)}{(z-p_1)(z-p_2)(z-p_4)\ldots(z-p_n)}.$$

Equivalently, the transfer function, functional form, can be written in a/b notation, where a's and b's are the coefficients of the 7th order denominator and mth order numerator polynomials respectively.

$$H(z) = \frac{b_0 + b_1 z^{-1} + b_2 z^{-2} + b_3 z^{-3} + \ldots + b_m z^{-m}}{a_0 + a_1 z^{-1} + a_2 z^{-2} + a_3 z^{-3} + \ldots + a_n z^{-n}}.$$

By using well known deconvolving techniques for the ARMA functionals one can divide the transformed microphone acoustic pressure signal by the transformed excitation source signal (using complex numbers) and thereby obtain the amplitude and phase of the transfer function. The transfer function is defined by the poles and zeros, or by the a and b coefficients in the two different ARMA functionals shown above. Furthermore one can, if desired, deconvolve the well known lip to microphone radiation function from the microphone signal to obtain the volume air flow function or transfer function at the lip and nose orifices. The ARMA approach, together with appropriate functional definitions of the excitation function and the acoustic data, makes possible the straightforward and automatic definition of a speech feature vector each speech time segment. For example, the algorithm stores the excitation function parameters defining a triangular approximation of the glottal volume air-flow versus time, it stores the transfer function using 14 poles and 10 zeros, the time frame duration, the prosody, some useful acoustic features, and the control values for subsequent speech technology purposes. For each of the functional forms, the information can be stored as a real time function, as a transformed function (e.g. Fourier transform) or as a mixed function as needed.

The feature vector information for each speech time frame can be normalized to a referenced speaker's (or speakers') feature vector for the speech sound spoken in the time frame. The normalization method is to compare measured (and processed) vector coefficients to those from both the user and from the reference speaker. Those of the reference speaker have been recorded during earlier training sessions. Normalization also removes variations in the interaction between the EM-sensors and the individual qualities of each speaker, as well as variations from one unit of equipment to another. In addition, the continuous value-range of each individual's coefficients, which represent a vocal articulator's range, can be quanitized to a smaller number of values. The "quantized" values are chosen such that a change, from one quantized coefficient value to the next, represents a desired user-distinguishable effect on the application. An example is that each quantized coefficient value represents a just-discernible change in a synthetic speech sound. These methods, described below, make possible the formation of speaker independent featured vectors for each speech segment. The coefficients in each a vector can be time-length independent, pitch normalized, rate normalized, articulator amplitude normalized and quantized, and they contain important aspects of the acoustic information. The methods described herein, make possible great improvements in speech coding because of the completeness of the vocal system information, the accuracy of coding the speech, the speaker and instrument independence, and the computational simplicity of the associated algorithms.

Figure 9B:
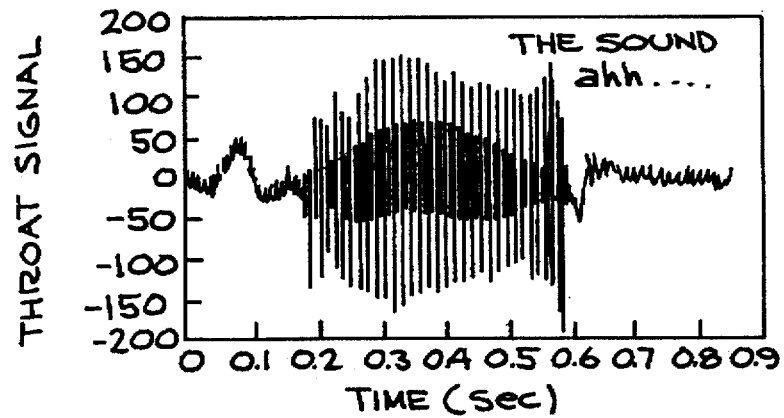

Example of Time Frame Definition and Feature Vector Formation:

For a male speaker saying the sound unit /ah/ extending over a time segment of 300 ms, the speech acoustic sensor and the vocal fold signal from the EM sensor were sampled at 11 kHz. FIGS. 9A and 9B show real time acoustic and glottal amplitude versus time signals, respectively. A transfer function was computed every 10 ms with a 32 ms Hamming window. Complex spectra, using both acoustic and glottal motion channels, were obtained using a 256 point FFT (Fast Fourier Transform). An ARMA model was used to best fit the input and output data in a least mean squares sense. Fourteen poles and ten zeros achieved the best fit. Such ARMA coefficients contain both magnitude and phase information. Knowledge of the ARMA coefficients allowed the construction of a feature vector describing the sound /ah/ for each 10 ms speech frame. Those essentially-identical speech frames were combined into a 300 ms multi-pitch-period speech time frame (i.e., thirty speech frames, each 10 ms were joined into one multi-time speech frame). The frequency response of the acoustic output and excitation input functions are shown in FIG. 10A, B respectively; and the computed transfer function amplitudes are shown in FIG. 11A. A similar process was used to generate the transfer function amplitudes for the sound /ae/, which are shown in FIG. 11B.

Figure 10B:
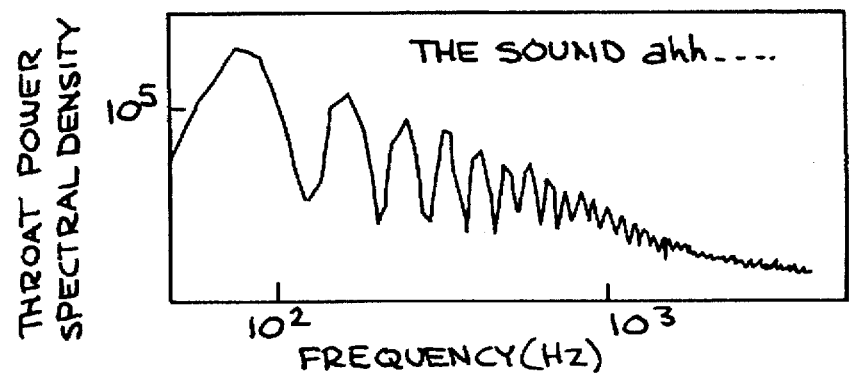

The feature vector shown in FIG. 12A for the sound /ah/, was constructed using a total of p feature vector coefficients, $c_1$ through $c_p$, to describe the processed data. In this example, $c_1$ is used to describe the type of transfer functions used, e.g. "1" means the use of an ARMA functional in the "pole" and "zero" formulation; $c_2$ describes the number of "poles" and $c_3$ describes the number of "zeros" used for the fitting; $c_4$ indicates the kind of speech unit being spoken, e.g. "0" means isolated phoneme; $c_5$ describes the type of connection to a preceding acoustic sound unit to be used, e.g. "0" means a connection to the silence phoneme is needed; $c_6$ describes the connection to the following unit, e.g. "0" means a connection to a following silence phoneme is needed; $c_7$ describes the 300 ms multi-frame speech segment envelope; $c_8$ is the pitch (e.g., 120 vocal fold cycles/sec.); and $c_9$ describes the bandwidth of the fundamental harmonic. Other feature vector coefficients that describe the relative ratios of the 2nd through the 10th harmonic power to the first harmonic, are taken from the power transform of the vocal excitation (FIG. 10B). In addition the fall of the harmonic excitation power per octave, above 1 kHz, can be described by a line with −12 db/octave negative slope. The "pole" artd "zero" coefficient data (FIG. 12B) are shown and stored as appropriate coefficients in the vector in FIG. 12A. The last coefficient $c_p$ is the symbol for the sound, and the next to last $c_{p-1}$ is acoustic information from a CASR or similar system which is the acoustic energy per frame. If the user desires to use the alternative formulation of the ARMA transfer functional, the "a" and "b" coefficients can be used (see FIG. 12C).

An alternative approach to describe the feature vector for the "long" speech segment /ah/ is to perform Fourier transformations each 8.3 ms (the period for 120 Hz excitation), and to join 36 individual pitch period frames into a 300 ms long multiple frame speech segment. A second alternative approach would be to take the Fourier transform of the entire 300 ms segment, since it was tested to be constant; however the FFT algorithm would need to handle the large amount of data. Because of the constancy of the acoustic phoneme unit /ah/, the user chose to define the 300 ms period of constancy first, and to then process (i.e., FFT) the repetitive excitation and output acoustic signal with a convenient 10 ms period 30 times, and then average the results.

As a test (see Section below on Speech Synthesis) a synthetic speech segment was reconstructed from information in a vector like the one shown in FIG. 12A. The vocal fold excitation function was first reconstructed using the harmonic amplitude and phase information to generate a source term over an interval of 100 ms. The excitation function was sampled at 11 kHz or higher. The time sampled sequence was used to drive the ARMA model specified by a difference equation with poles and zeros. The output of the ARMA model was used to reconstruct the speech sound /ah/ as shown in the section on Speech Synthesis (see FIG. 19), and a pleasing sound, /ah/, was generated and heard by the user.

Applications of Preferred Embodiment:

The procedures to define speech time segments and to form feature vectors allow many applications. First, the user-speaker or other speakers, who serve as references, are asked to speak into a sensing and recording system, such as are shown in FIGS. 3A or 3B. Feature vectors are formed for all single unit sounds in a language (e.g. syllables, phonemes, PLUs, and acoustic speech units) and for as many multisound unit sounds (e.g., diphonemes, triphonemes, words, and phrases) as are needed by the user for the application. The identified feature vectors, for the speech segment, can be normalized and quantized as needed, and are stored in a codebook (i.e., library). The identification of the stored feature vectors can be done in several ways. They can be labeled by the frame position in a time sequence of frames or be labeled by a master timing clock. They can be labeled using known labeling of each feature vector with user provided acoustic speech unit names (e.g. FIG. 12A, last coefficient, $c_p$=ah, describes the phoneme /ah/). They can also be automatically labeled using speech recognition to add the missing acoustic speech unit label to the feature vector for the speech segment. Because of the direct relationships between speech organ positions, their rates of motion, and the sound units produced, the methods described herein provide a more fundamental parametrization of vocal system conditions during speech than has been possible before. They make possible simplified but very accurate descriptions of single acoustic speech units, as well as descriptions of acoustic speech units that include multiple phonemes such as diphones, triphones, whole words, and other well known combinations, Once the speech segments are identified and stored, many applications are possible. They include speech recognition, speech synthesis, vocoding for telephony, speech prosthesis and speech correction, foreign language identification and learning, and speaker identification. For speech recognition, the user can perform direct phonetic-template matching with previously stored feature vectors in a library for the purposes of automatic speech unit identification. Similarly, the user can use Hidden Markov Models, or neural networks, or joint or exclusive statistical techniques for the identification of one or several consecutively formed feature vectors using previously stored information. For purposes of speech reconstruction (i.e., speech synthesis) the coding procedures make possible the characterization of any individual speaker's sounds. Then, using methods for accurate synthesis of each speech segment, many speech segments are joined together. Synthesized speech can be altered as desired. Speaker identification and language identification are made possible because the speech coding reflects the specific properties of each user and the properties of the language the user is speaking.

Voiced Excitation Function Description

The preferred method is based upon air volume flow through the vocal tract as the independent variable and air pressure as the dependent variable. An EM sensor is positioned in front of the throat at the location of the vocal box (i.e., larynx). It measures the change in EM wave reflection from the vocal folds and surrounding glottal tissue as they open and close. The user can determine the relative volume of air flow through the glottal opening during the voicing of each voiced acoustic speech unit. This allows one to measure and generate, in an automated fashion, an accurate voiced speech excitation function of any speaker and to define the speech time frame interval or intervals during which this function provides a constant, periodic repetitive excitation.

One demonstrated method is to measure the change in EM wave reflection level from the glottal region as the vocal folds open and close using a "field disturbance" EM sensor optimized for glottal tissue motion detection. By time filtering to allow a signal bandpass of approximately 50 Hz to >2 kHz, the voiced glottal signal is easily measured and separated from other signals in the neck and from those associated with slower body motions moving the sensor relative to the neck. The next step is to associate each reflection condition with the area opening of the glottis. The area measurement methods are based upon using known physics of EM wave scattering from dielectric materials, by using mechanical and physiological models of the glottal tissues, and by calibration of EM sensors signals against physical air flow and/or pressure sensors. Then a model of air flow vs area, based upon fluid dynamic principles, is used. For other applications, depending upon the coding fidelity of speech needed, the EM sensor can be optimized to generate more accurate data, wider bandwidth data, and data with increased linearity and dynamic range.

Generalized methods of obtaining the vocalized excitation function include procedures where the EM sensor amplitude versus time signal is calibrated against laryngoscope pictures of glottal area vs. time and/or air sensor amplitude vs. time signals (e.g., using air flow and/or air pressure sensors). One method uses a laryngoscope to optically photograph the area opening, versus time, simultaneously with the EM sensor measurement of the EM reflection signals. FIGS. 13A–F are examples of vocal fold opening and closing images of the glottal area. Another method is to place air sensors in various vocal tract locations to calibrate the EM sensor signals against absolute air flow versus time signals, or against pressure versus time signals. A direct functional relationship between an EM-sensor signal-amplitude at a given time and the associated air flow signal (or its dual pressure value) at the same time is obtained by measuring both substantially simultaneously under the needed conditions of use for the speech vocabulary in the application. These methods are especially valuable for obtaining the glottal open and closure times and the shape (i.e., derivatives) of the air flow versus time signal at the moments of glottal opening and closure for coding applications needed for speech synthesis applications. Normalization procedures are used to correct the signals, and the relationships are stored in a lookup table or codebook, or the relationships are approximated by model based or curve fitted functions. Thus for each EM-sensor signal value from glottal tissue, an airflow or air pressure value can be associated.

Experiments with excitation functions based upon air volume flow were conducted to validate the methods. The data are analytically described by using well known fluid flow equations, one of which was described by Flanagan 1965 ibid on p. 41, equation 3.46. The resistance to airflow through the glottal opening, at constant lung pressure, is given in equation (1) below. The resistance Rg is equal to the difference in pressure on either side of the glottal opening (i.e. the transglottal pressure $P_s$) divided by the total air flow U (i.e. volume air flow). For this example, $\rho$=air density, l=length of glottal slit, and w=transverse opening of glottal slit (see FIG. 13B). The viscous term in Eq. (1) is neglected, because it is only needed for small openings, and was not used for the validation experiments.

$$Rg = P_s/U = (\text{viscous term}) + 0.875 \, \rho U/2(\text{lw})^2 \quad (1)$$

$$P_s = U * Rg \quad (2)$$

$$P_s = 0.875 \, \rho U^2/2(\text{lw})^2 \quad (3)$$

$$U = (\text{lw}) * (P_s/0.438 \, \rho)^{1/2} \quad (4)$$

Figure 14A:
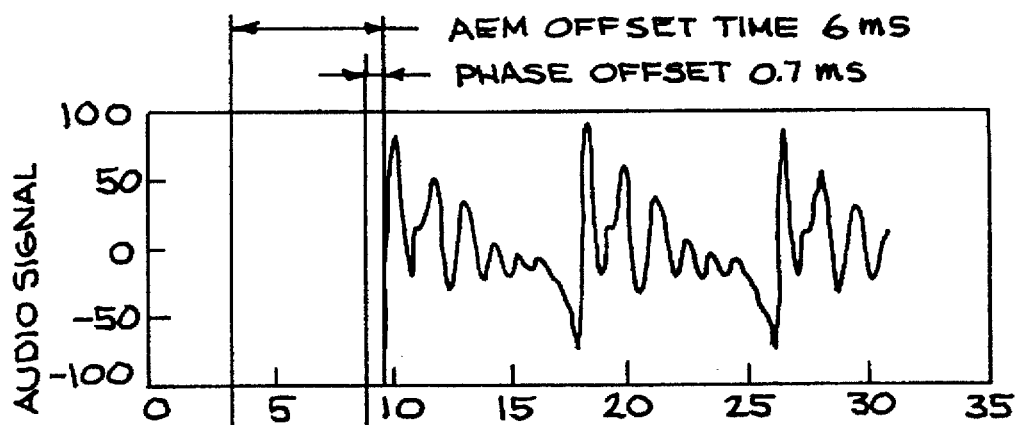
FIGS. 14A,B show the substantially simultaneously recorded acoustic signal and the corresponding EM sensor signal showing glottal motion versus time for the phoneme /ah/.
Figure 14B:
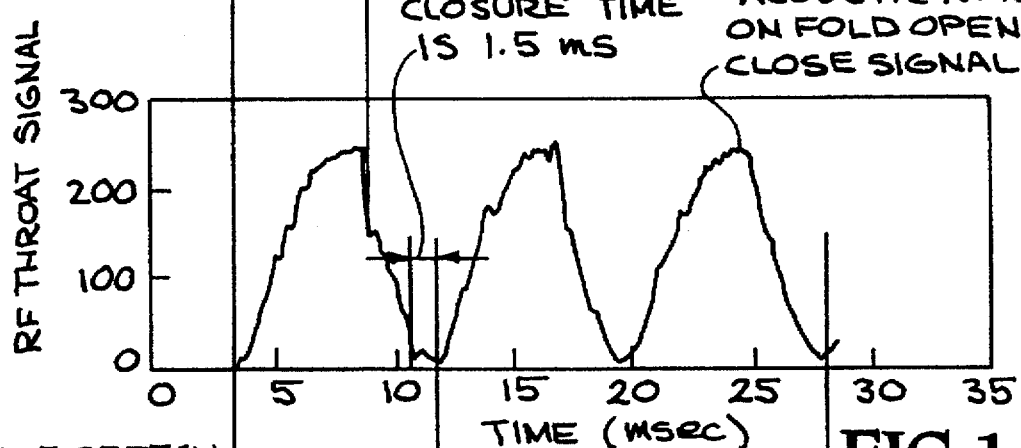

The change in the glottal opening area, lw, is proportional to the change in the EM wave reflection caused by the change in the local dielectric value as the glottal tissue material moves. This example uses the approximation that the reflected EM wave-signal changes in proportion to the reduction in glottal tissue mass as the glottis opens. This interpretation works well for the "field disturbance" type of EM sensor used in the experimental examples. Using knowledge about the shape of the glottal opening, a further relationship is developed whereby the tissue mass of the opening is reduced in proportion to w, the glottal width, in equation (4). Thus measuring "w" directly with the field disturbance EM sensor (or by using other sensor systems such as a range gated EM sensor) the needed area value versus time is obtained. Then using equation (4), the needed volume air flow signal, U, versus time is obtained from the area value, lw. FIGS. 14 A,B show an experimentally obtained acoustic signal and the associated EM sensor signal from glottal tissue motions. Using the relationships just derived between the EM sensor signal and the volume air flow, U, and assuming constant transglottal pressure, $P_s$, the signal in FIG. 14B describes the relative volume air flow, U, versus time.

The simplified analytical approach, used above for modeling the air flow resulting from EM sensor measurements of the glottal tissue motions, is employed to demonstrate the effectiveness of having excitation function data, i the clarity of the timing information, and the directness of the deconvolving process. The experiments assumed constant lung pressure and constant transglottal pressure during each speech frame in this description of a short speech segment. For most cases relative changes in air flow, U(t), are sufficient, and slowly changing lung pressure does not matter. However, if lung pressure is needed, an EM sensor can be employed to measure the lung volume change or diaphragm motion to determine relative lung volume change. In the cases of changing transglottal pressure over the needed measurement periods, methods are described below. In addition, the change in the amplitude envelope of acoustic speech generated over several glottal periods can be recorded in a feature vector, and provide a measure of relative change in air flow and thus in excitation amplitude. Such amplitude changes provide important prosodic information for speech recognition, speech synthesis, and are especially valuable for speaker identification procedures where individualized intonation of identical spoken phrases is very idiosyncratic.

The procedures used volume air flow as the independent variable. However EM sensors optimized to sense the condition of other glottal tissues, as they respond to changes in volume air flow or to local pressure, can be used and their responses can be fed into an equation (i.e., algorithm) which will provide a volume or a pressure versus time vocalized speech source function for use in coding procedures.

Air Flow Corrections Due to Post- and Trans-Glottal Pressure Variations:

It is known that for most conditions, the glottal opening is a high impedance air flow orifice, meaning that the glottal impedance is substantially higher than the following post glottal impedance values. In this approximation, post-glottal vocal tract changes do not affect the transglottal pressure and the air flow through the glottal orifice. However, in more realistic approximations, such air flow changes can be important. The user may wish to describe, more accurately, the voiced excitation function, and may wish to use one of the following methods employing EM sensor signals plus noted algorithmic procedures. While the above model of the air flow through the glottal orifice assumed constant pressure on both sides of the vocal folds (i.e., constant transglottal pressure), the effects of a postglottal pressure change during the speech time frame can be estimated using well known approximation techniques from electrical analogies and from physical principles, or can be measured using tissue motions sensitive to local pressure. These pressure corrections can be important because, from FIG. 16, when the post glottal pressure $P_1$ (represented as voltage $V_1$) becomes a significant fraction of the lung pressure $P_o$ (represented as voltage $V_o$), then the use of glottal area to define volume air-flow function, U, breaks down. An improved expression with the necessary corrections must be used for applications where the highest quality excitation function characterization is needed, e.g. during "obstruent" articulation.

By using the EM-sensor for glottal motion, in a high sensitivity mode, the user can measure low amplitude vocal-fold tissue motions (e.g., vibrations) that are known to be caused by air flow pressure changes. Such pressure fluctuations are caused, for example, by backward propagating acoustic signals. Vibrations that affect the glottal opening can be distinguished from other surrounding tissue vibrations being sensed by the same EM sensor. FIG. 14B shows examples of such vibrations which slightly modulate the peak envelope-amplitude signal of the glottal-opening versus time signal. These are known to be associated with acoustic pressure waves, because when the low frequency glottal envelope is electronically filtered away, leaving the higher frequency vibration signals, the latter can be amplified and sent to a loud speaker. The broadcasted signals are recognizable as being nearly identical to the acoustic speech recorded by the microphone. These signals are measured to be small, and calculations describing the magnitude of these effects also indicate them to be small in most cases. In applications where high coding fidelity is important and where the compliance of the glottal tissue is needed for mechanical models or for speaker identification, the following methods are used to provide the needed additional information. Seven methods are described for accommodating the variations in the glottal-air flow versus time, due to transglottal pressure changes. They are used to form improved vocalized excitation function descriptions over the defined time frames of interest:

1) Make no changes to the glottal opening signal, even though it is known that the air flow model is being perturbed by changes in the transglottal pressure. Form a numerical approximation of the volume air flow function vs. time assuming constant transglottal pressure. Deconvolve the volume air flow function from the acoustic signal. Using an appropriate transform functional, find the numerical coefficients describing the transform function for the time frame. Construct a feature vector for the time frame, using the uncorrected excitation function, the related transfer function, and measured acoustic signal parameters (as well as other coefficients described below under feature vector formation). The three speech functions used in this method, E(t), H(t), and I(t) are together self-consistent. They can be used for real time feature vector formation and time frame definition, as well as to generate the needed application specific codebooks realizing that many of the feature vector parameters (and thus the codebooks) are imperfect but they are all self-consistent. For many applications, feature vectors generated using this method are good enough.

2) Using physiological data of the individual speaker (or using an average human vocal tract) together with an air flow speech model of the transfer function, calculate the post glottal pressure from the impedance of the transfer function looking from the glottis forward. This procedure is well known to experts who model air flow and pressure in speech tracts. (An additional EM sensor to measure various vocal tract organ positions can be used to provide data to aid in choosing a transfer functional and its consequent impedance). Use this impedance to make a first order correction to the transglottal air pressure and thus a correction to the air flow obtained from Equations 1–4 above. Use the corrected volume air flow to form a corrected excitation function feature vector.

3) Remove post-glottal pressure induced vibrations of glottal tissue and nearby tissue from the EM sensor signal, and therewith from the associated model of volume air flow versus sensor signal. Use one of two related methods. Method 3A) Filter the raw EM sensor excitation signal using transform or circuit techniques to remove the acoustic pressure induced higher frequency noise, but preserve the needed low frequency excitation function shape information for model generated values of volume air flow and for subsequent feature vector formation. Method 3B) Use the tissue vibration signal from the EM sensor and the acoustic output (corrected for timing delays) to determine the backward acoustic transfer function. Divide the Fourier transforms of the vibration signal by that of the acoustic signal, and store the numerical (or curve fit) transfer function information in memory for recall as needed. Next, for each time frame, use the backward transfer function to calculate the glottal tissue vibration level associated with the measured output acoustic signal. Then subtract the backward transferred acoustic signal from the EM-sensor generated and processed signal, to obtain a "noise free" excitation function signal. This signal represents a backward traveling acoustic sound wave that induces mechanical vibrations of glottal tissue and nearby air tract tissues in directions transverse to the air flow. This acoustic wave has little effect on the positions of the vocal fold edges, and thus it does not affect the actual volume air flow, U. However, certain EM sensors do measure this noise, and it shows up on the EM signal describing the excitation function (see FIG. 4B for an example). This noise level is found to be speaker specific. For high fidelity, speaker independent excitation function coding, such vibration signals mixed with the gross air flow values are undesirable.

4) Detect glottal tissue or nearby tract tissue motions that are transverse to the air flow axis and that are proportional to local pressure. Use, for example, a range gated EM sensor, optimized to measure the motions of pressure sensitive tissue, in directions transverse to the air flow axis. Calibrate using simultaneous signals from an EM sensor and from an air pressure sensor located near the pressure sensitive tissues. Use the EM sensor measured pressure, in each time frame, to determine air flow corrections in Equation (4). Correct those air flow values, due to post-glottal pressure variations that exceed the error-limits (user-defined) of the constant transglottal pressure approximation used in Equation (4).

5) Remove EM sensor measured noise on the glottal opening signal, by removing all signals not consistent with the mechanical equations of motion of the vocal folds (using known models such as those in Schroeter, J., Lara, J. N., and Sondhi, M. M., "Speech Parameter Extraction Using a Vocal Tract/Cord Model," IEEE, 1987). Use EM sensors to measure and set the constants in the physiological model functions describing an individual's vocal fold motions, as described below in the section on physiological models. Use well known Kalman or other model based filtering techniques to filter signal contributions inconsistent with the model.

6) Insert an air flow sensor (and/or a pressure sensor) in the post glottal air tract and, using essentially simultaneous EM sensor signals, calibrate changes in transglottal air flow (and/or pressure) that are inconsistent with the model shown above in Equations 1-4, or for other models of air flow versus EM sensor signal. During training sessions, obtain this data for the vocal tract configurations and for the frequencies where the effect is measured to be important for the application at hand. Then form a table lookup or a curve fit to associate each EM sensor signal value with a measured air flow value (and/or pressure value). During the actual speech application of the methods herein, obtain the EM sensor signal of glottal tissue motion. Associate the sensor signal with model values of uncorrected air flow or pressure, and then correct the air flow and/or pressure values as follows: 6A) Use the table of EM sensor versus pressure data to correct each post glottal or transglottal pressure estimate in the preferred model approach (e.g., Equations 1-4), or 6B) Use the table of EM sensor versus measured volume flow to directly correct each raw value of the air flow excitation function with a corrected value on a point by point basis. Describe the corrected pressure or air flow signals as amplitude versus time, or as Fourier amplitude and phase vs. frequency in transform space.

Figure 16:
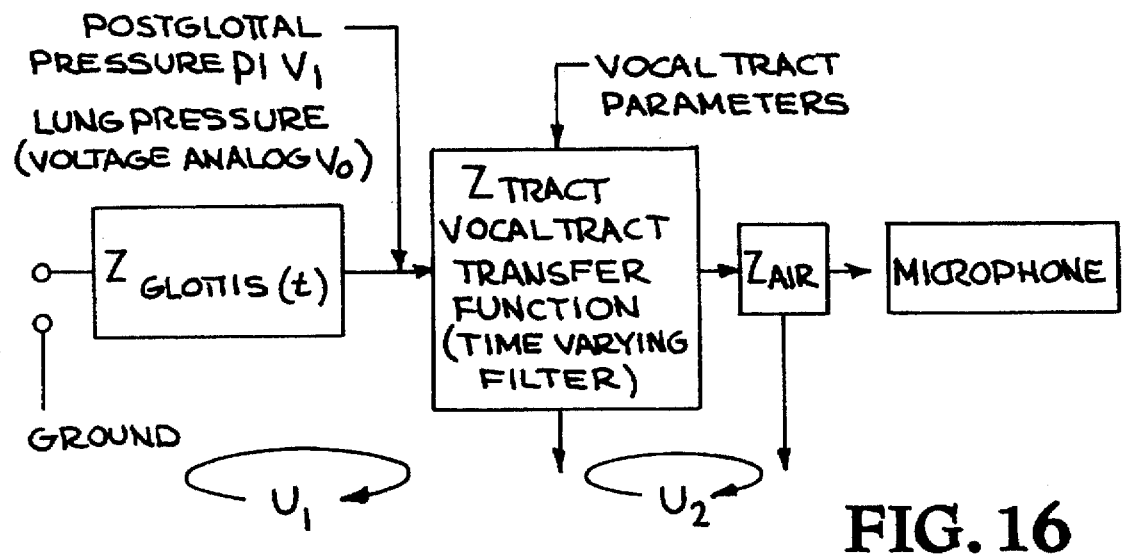
FIG. 16 is a source and impedance model that is an electrical analog to an acoustic model.
Figure 17A:
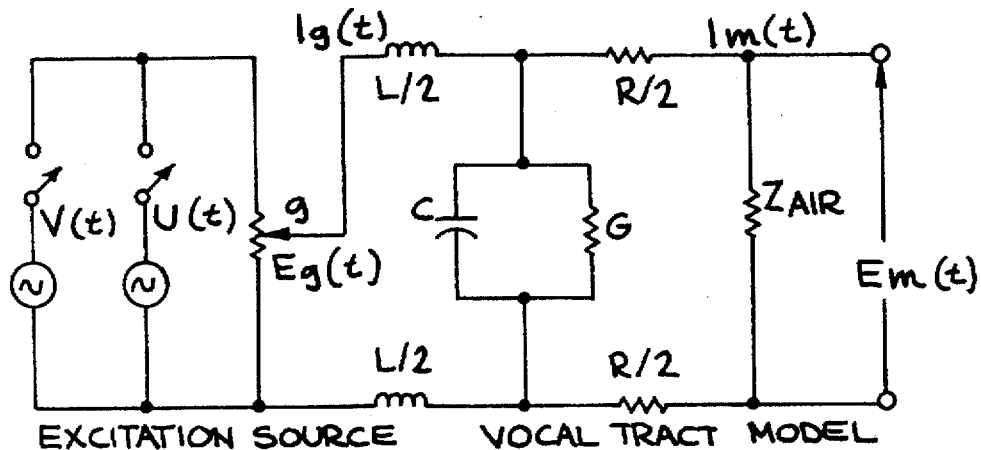
FIG. 17A shows a single mesh electrical analog circuit that models the first formant of the sound /ae/, using volume air flow as the independent variable.
Figure 17B:
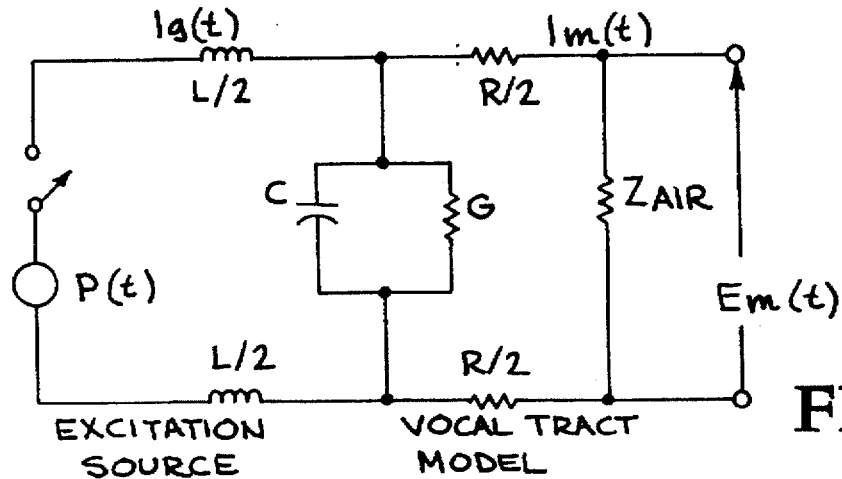
FIG. 17B shows a single mesh electrical analog circuit that uses air pressure as the independent variable.

7) Change the model to make pressure the independent variable in the mathematical equations that describe the speech tract (for a circuit model example, see FIG. 17B). Make volume air flow the dependent variable. The interchanging of voltage and current (i.e., pressure and volume air flow) between being the independent and the dependent variable in circuits and mathematical analogs is well known. See FIGS. 16, 17A, and 17B. Construct a table of EM sensor signal values versus measured pressure, for the range of vocal articulator conditions needed in the application as described in paragraph 6) and/or 4) above.

In summary, the algorithms obtains the excitation function, E(t), for each speech time frame, corrects it to the degree needed by the application by one of the above seven methods. The next, described below under the section on transfer functions, is to deconvolve it from the acoustic output to obtain the transfer function for the speech time frame and for the application. Experiments have validated methods, 1), 3A) and 6) above. Method 1) has been used to generate sufficiently accurate feature vectors for several speech recognition and speech synthesis applications. Method 3A) has been used to remove high frequency noise from the vocal fold area versus time signal and method 6) has been used to calibrate an EM sensor against vocal tract air flow.

Formation of Voiced Feature Vectors:

The volume air flow function data provides, for the first time, a valuable description of the human voiced excitation function during each glottal open/close period of voiced speech. Most importantly, it enables the user to obtain the exact shape of the air flow vs. time and the duration of the vocal fold closure time (i.e., sometimes called glottal "zeros"). FIGS. 14A,B show annotated experimental data of measured glottal openings versus time. Typical triangular-like pulse shapes are seen. The sequence of individual pitch periods (i.e. single period speech time frames) are essentially all the same; thus a multi-time frame feature vector is easily formed. Secondly, this data shows a time offset between the acoustic signal and the EM sensor signal. This is caused primarily by the time of flight difference in timing between an EM signal reflected from the glottal tissues and the much slower acoustic signal which travels a longer path from the glottis, out the mouth/nose to the acoustic microphone. If timing corrections are needed, calibration procedures can be employed using laryngoscopes, air flow or pressure sensors, EM sensor calibration procedures, and/or accurate time measurements.

The glottal air flow (or pressure) amplitude vs. time can be used and coded in a variety of ways. They include describing the real time amplitude versus time interval, taking the appropriate transform, and/or approximating the shape by appropriate functions such as polynomials, a one-half sine cycle, piece-wise polynomials such as a triangle, and other similar functions. One example of coding the excitation function for minimum bandwidth transmission is to measure and store the excitation function feature vector as the parameters of a triangular open/close glottal area function versus time. It is described by the pitch period, the fraction of the period the folds are open (using the convention that the glottis opens at the start of the pitch period), and the location in the period of the peak opening and its magnitude (the peak amplitude is normalized). This simple description is more accurate than many presently used excitation functions and, for this example, is described by only 3 numbers of 4 to 8 bits each. Furthermore, if several periods are measured to be "constant" in pitch period duration and acoustic output, the sequence of such periods can be represented one more number period plus one more number describing the number of periods of constant acoustic output, defining a multiple pitch period time frame.

A more complex excitation function feature-vector formation approach is to take the Fourier transform of the volume air flow vs. time over one or more glottal periods during which the acoustic speech units are constant and repetitive. An example is a long spoken /ah/ phoneme that is vocalized over a 0.3 sec duration. The feature vector and time frame are formed to describe the excitation function over a 0.3 sec time duration of substantially constant speech. For example, the user can record the frequency location of the highest amplitude signal (which is the first harmonic) that is the pitch or pitch period. In addition, the user can record the fractional amplitude levels of the higher harmonics compared to the fundamental harmonic, the phase deviation of the higher harmonics from the fundamental, and the bandwidth of the fundamental. Higher harmonic (e.g., where $n \omega_o > 10 \omega_o$) amplitude intensity relationships to the fundamental can be modeled knowing the mechanics of the vocal folds or by recording the experimentally measured rate per octave of fall, usually −12 db.

Multi-time-frame feature vectors are formed by testing for constant or slowly changing waveform signals over several voiced speech periods. Constant means the acoustic and excitation amplitudes vs. time are nearly identical from one frame to the next, with nearly identical being defined as the amplitude in each time interval being within a chosen fractional value of a defined standard. This degree of constancy to a standard can be easily defined by the user ahead of time and automatically employed. The capability of this method to define constancy over one or more speech time frames using automated procedures is valuable because it enables economy of computing and increased accuracy of the functional descriptions. The reason is that one needs to only do one computation, using several speech frames with more repetitive amplitude data in contrast to performing a separate computation over each and every speech frame.

In addition, the user can define a slowly changing function that describes the change in volume-air-flow (or pressure) excitation over several speech time frame intervals. Examples of decreasing pitch periods occur during syllable emphasis or during a question. A feature vector can be formed over a time frame of several pitch periods, which contains the basic excitation function constant from a single period time frame together with one or two numbers that describe the functional change over the defined time frames. FIG. 14B shows the slight change in constancy of a voiced excitation over several speech periods as the speaker says the phoneme /ah/. This procedure also provides a means of defining a feature vector based upon deviations from the voiced excitation function of an average speaker or from the stored feature vectors of a specific speaker. In this case, the feature vector contains the deviations from average values, not the absolute values. This can be done in real time or Fourier space, or using mixed techniques.

FIGS. 9A,B, 10A,B and 11A show data taken by a male speaker saying the phoneme /ah/ for 36 consecutive glottal open/close speech periods, and derived speech functions. These figures illustrate the amplitude vs. time signals from the acoustic microphone and a glottal EM sensor (FIGS. 9A,B), the Fourier power spectrum of each set of sensor signals (FIGS. 10A,B), and the speaker's vocal tract transfer function (FIG. 11A) obtained by deconvolving the data in FIG. 10B from 10A. Using the procedures described below, a feature vector was formed over a time frame of 300 ms, in which the descriptors of the excitation function were taken from the Fourier transformed glottal function in FIG. 10B. The feature vector formation process is illustrated in FIGS. 12A,B. Experiments using data, as illustrated in FIGS. 9A,B, show that the computation time to obtain pitch values, using the methods herein, is five times faster than by using conventional acoustic processing techniques, and the pitch values are more accurate than conventional acoustic-based techniques by over 20%.

Figure 15A:
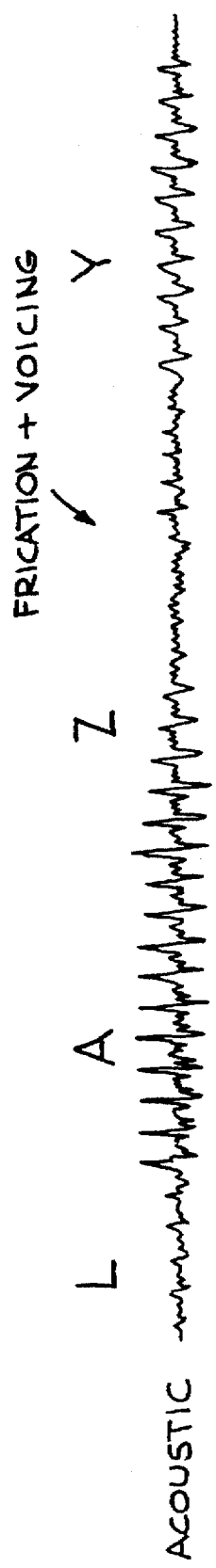
FIG. 15A shows several acoustic speech segments for the word "lazy".
Figure 15B:
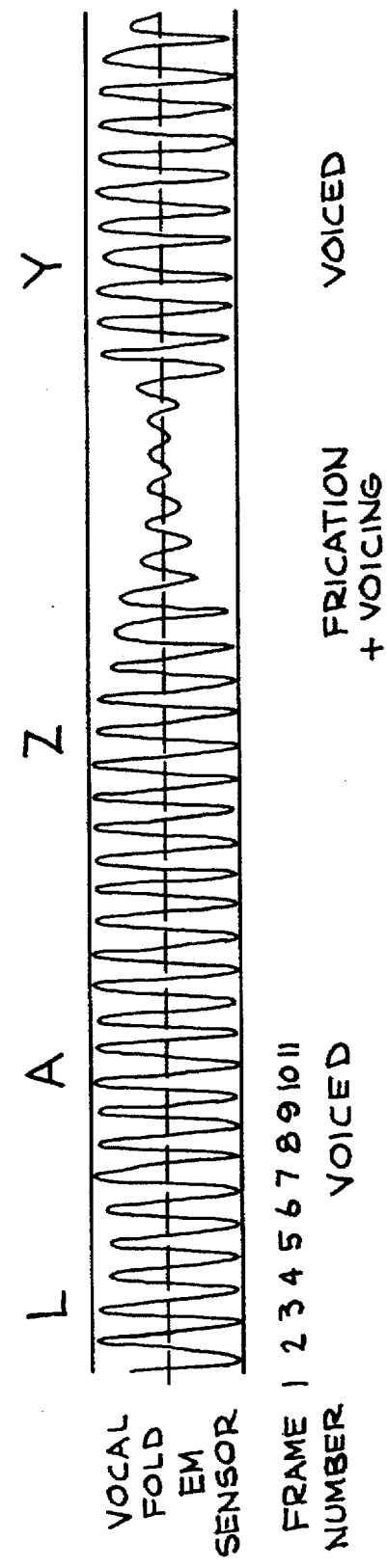
FIG. 15B shows speech time frames and EM sensor vocal fold signals for the voiced and combination voiced/unvoiced unit /z/ in the word "lazy".

Master Timing:

The method of measuring the glottal open-close cycle allows the user to define master timing intervals or "frames" for the automation of many speech technology applications. In particular, it allows the vocalized excitation function periods to be the master timing intervals for the definition of time frames in the processing steps described herein. This approach allows the user to define the beginning and end of a glottal open/close cycle, and it provides a well defined method to join the information from one such cycle to the next cycle. It enables the concatenation of the information obtained in one speech time frame to be joined to that obtained in the next speech time frame. FIGS. 14A,B are illustrations of master timing, where each time frame is defined as one glottal cycle (i.e., pitch period), and the associated information is measured and labeled. FIG. 15B shows a sequence of single pitch period speech time frames for the spoken word "LAZY", and FIG. 15A shows the simultaneously measured acoustic information. One can define absolute pitch, the time frame duration, and characterize the timing information and store it as part of the speech frame feature vector which describes the acoustic speech unit spoken during the time frame. The cases when unvoiced speech segments occur are discussed in the section on unvoiced excitation.

The use of the glottal time period as the master timing signal allows the user to define time frames consisting of several glottal periods. See FIGS. 14B and 15B for illustrations. The user sets algorithmic criteria to define "constancy" of the speech features being measured in order to determine how long the voiced speech time frame lasts. Then the algorithm measures how many pitch periods were used during which the "constancy" of feature values existed which are being used to describe the acoustic speech unit just sounded by the speaker. In the example above, the algorithm decided that 300 ms of constant sounding of the phoneme /ah/ took place. In this example, one of the "constancy" variables measured, and determined to be sufficiently constant, was the repetition frequency of the 36 glottal open/close cycles. The algorithm then defined a feature vector that described the time frame duration, the excitation function amplitude versus time for one period, and other information as shown in FIGS. 12 A,B. Such a feature vector describes the acoustic speech unit, to the degree needed by the user, for the entire duration of the time frame. Because of the multiple glottal periods, the algorithm can average information obtained over one or several of the included pitch periods, it can measure small period to period feature coefficient variations (e.g., pitch period variations) from the average which are useful for speaker identification, and it can use Fourier (or other) transforms to determine the voiced excitation function over as many or as few pitch period intervals as desired (or as many as the Fourier transform algorithm allows).

In the case that the speech changes from voiced to unvoiced, the last glottal open/close period of the voiced speech sequence has no "next" glottal cycle to use to define its end of period. In one approach, the algorithm continually tests the length of each glottal closed-time in each time frame for excessive length (e.g. 20% longer than the preceding glottal period closure-time). If the period is texted to be too long, the algorithm terminates the period and assigns, for example, a glottal-closure time-duration equal to the fractional closure time of the glottal function measured in the preceding time frames.

This method of defining constancy of speech over several glottal periods saves computation time and storage space in the computing processors and memories needed for many applications. It also allows the acoustic speech (and other instrument outputs) to be timed in a speech time frame along with other feature vector information obtained using the above timing procedures. For many examples herein, the feature vector is timed by the start time of the first glottal period provided by a master clock in the processor and its duration is defined by the number of constant glottal periods. This process automatically results in significant speech compression coding because feature vectors defining periods of constancy, as defined herein, can be shortened to one glottal period, plus a single number describing the number of glottal periods used.

The procedures above allow the definition of a time frame and the formation of feature vectors in which some of the coefficient values are slowly and predictably changing over a sequence of glottal pitch periods. An algorithm can define a time frame, over which slow changes in feature values (i.e., coefficients) take place, as follows. It measures the change in the coefficient value (e.g., pitch period) and fits the sequence of changes over several glottal cycles to a predefined model. If the values do not fit the model, then a time frame with one or more slowly changing feature vector coefficients is not formed. If the coefficient values change too much, beyond the allowed range, an end of the time frame is defined. For example, a linear decrease in pitch period by 0.5 ms per cycle might be measured over 5 sequential glottal cycles, as a speaker "inflects" the pitch during the sounding of a single phoneme, when a question is asked. The algorithm also examines the other feature vector coefficients being measured during the time frame, but not being examined for slow change, to be certain that they remain sufficiently constant as demanded by the algorithmic definition of a speech time frame.

An example of such timing is shown in FIG. 14B where the first speech frame time period is 8.5 ms, the second is 8.0 ms, the third is 8.0 ms. A master clock in the processor times the onset of the first frame to be at 3.5 ms, the second at 12.0 ms, the third at 20.5 ms. The pitch deviations, referenced to the first frame, are −0.5 ms/frame referenced to the first frame. The constant time offset between the fast closure of the glottal folds and the onset of the acoustic set is 0.7 ms, which is caused primarily by the differences in the distances and the speeds of signal travel between the EM sensor signal and the later arriving acoustic signal at the microphone. Such a time offset value does not influence the Fourier deconvolution process, as used in these examples. Another offset number is defined as the acoustic/EM frame-offset (or AEM number) by this method. It has value for recording the acoustic signal timing with respect to the EM signal timing. It allows the user to define the zero time of the acoustic signal with respect to the speech frame start. This characterization has value for speech to lip synchronization applications where sound to lip or other facial motion synchronization is required.

An example of a multiple pitch period time frame can be defined using measured data shown in FIG. 14A for the phoneme /ah/. By testing that the three measured pitch period changes referenced to the first pitch period, are 0.5 ms or less, and defining that a 0.5 ms change is constant enough for an application then a multi-period time frame can be formed. The other information in the sequence of feature vectors must also be tested, and assuming it is also constant enough (for example the acoustic information in FIG. 14A is constant enough), a multi time frame can be formed into one feature vector describing a time frame 3 glottal periods long. One particular method for defining the pitch of the 3-pitch period vector is to use the average pitch period over the three frames, which is 8.16 ms; the average pitch deviation can also be measured and stored. Also in this example, the speaker was slowly raising his pitch (i.e., the pitch period shortened by 0.5 ms) as commonly occurs when stressing the end of a sound. This change can also be identified by the algorithm and stored if desired.

Using these methods the user can associate with each feature vector the start, duration, and stop times of the time frame using a continuous timing clock in the processor. The user can also store the absolute and relative timing information of the EM sensor information relative to other information (e.g., the acoustic signal) as part of each feature vector. Such timing information can be used to subsequently reconstruct the acoustic and other information in the proper speech order from the information contained in each single or multiple frame vector. In cases where the acoustic signal from the combination of the excitation and transfer function is known to last longer than a single glottal period speech frame, the transfer function information obtained allows the user to identify the part of the acoustic waveform that extends into the next speech period. The user is able to use such acoustic signal amplitude information in the time frame under consideration as needed.

The methods herein allow the user to conduct additional simultaneous measurements of speech organ conditions with instruments other than EM sensors. The methods herein allow the user to define "simultaneity" using the master timing information procedures described above for such measurements as video, film, electrical skin potential, magnetic-coil organ-motion detectors, magnetic resonance images, ultrasonic wave propagation, or other techniques. The methods herein allow synchronization, and incorporation into the feature vector for each time frame as desired, of such instrumentation output.

Unvoiced Excitation:

Using the general methods described above for voiced speech, one can determine the unvoiced excitation functions of the speaker and define unvoiced transfer functions, as well as speech frame timing and feature vector coefficient values. The method uses the algorithmic techniques for voiced/unvoiced detection that are described in the copending patent application Ser. No. 08/597,596. This algorithm uses EM sensors, especially the vocal fold EM sensor signals, to determine that acoustic speech is occurring without glottal open/close motions. Speech without glottal cycling is unvocalized speech.

The user selects (automatically or manually) an appropriate modified "white noise" excitation function that has been validated by listeners, by analysis, or derived using deconvolved functions as described herein. Such noise functions are characterized by their power spectrum per unit frequency interval. For excitation function feature vector formation, either a pattern (or curve fit) of the spectrum can be stored, or a numerical value can be stored which represents one of the small number of unvoiced excitation spectra needed for the application. Other EM sensors can be used (if available) to determine the source of the vocal tract constriction (e.g., the tongue tip, lips, back of tongue, glottis) and a modified white-noise excitation source appropriate to the air turbulence source, with proper noise spectrum, can be chosen. Once the source is defined, the chosen excitation function transform is divided into the acoustic output transform to obtain the transform of the transfer function of the vocal tract. The process to obtain the transfer function is identical to methods described above for generation of voiced transfer functions.

Unvoiced Speech Time Frames and Feature Vectors:

Unvoiced excitation functions can be obtained by using the methods described above in the section on processing units and algorithms to deconvolve the transfer function from the output signal to obtain the excitation function. The user first asks a speaker to speak phoneme sequences in a training session, using unvoiced phonemes, during which an acoustic signal is recorded. The user then uses general knowledge of the speaker's acoustic tract, obtained from the literature or by using transfer functions, obtained by using voiced versions of the identically formed unvoiced phonemes. An example is to use the transform function from the vocalized phoneme /g/ to obtain the excitation function for the unvoiced phoneme /k/. The user performs a deconvolving operation to obtain the transfer function by removing the tract influence from the acoustic signal. The user then obtains the unvoiced excitation function used by a given individual in the measured speech frame. The user then stores the functional description for the specific individual, as a set of coefficients in an excitation function feature vector (i.e., to determine the noise generator spectrum), either using real time, transform, or mixed techniques. Typical uses of this and similar functions are for the deconvolving of acoustic output (during real time speech) to obtain a transfer function for complete feature vector formation, using processes as described in the section on feature vector formation. The full or partial feature vector for each unvoiced acoustic speech time frame is then available for the user chosen application.

The following three methods can be used for forming acoustic speech unit time frames when unvoiced speech is being sounded.

1) The user measures the time duration that an unvoiced excitation of acoustic speech units (e.g. phoneme or series of phonemes) is being sounded, during which no "significant" change in the spectral character occurs. This constancy definition for turbulence-induced sound is usually measured in frequency space where relative amplitude changes per predefined frequency intervals can be easily measured. For this method, "no significant change" is defined by first setting variation (i.e., constancy) limits within which the transform of signal levels must remain. Then during speech processing, each appropriate signal, such as the spectrum of acoustic output and other available EM-sensed organ-motion signals, are examined to determine if "change has occurred". A simple example of "change" is to use an EM-sensed start of glottal open/close motion to signal the algorithm that a transition to vocalized speech has occurred, and thus unvoiced speech has stopped being the sole excitation. The duration of each unvoiced time frame is defined to be the total time of constant unvoiced speech, until a sufficient change in the acoustic or EM sensor signal occurs to signal the algorithm that a new time frame is defined.

2) A default algorithm is defined to accumulate data as in 1) above for 50 ms (or other user chosen time), and to define a 50 ms long speech frame and associated feature vector if no change in the constancy of the feature vector coefficients has occurred. If acoustic speech or a sufficient organ condition change occurs before 50 ms has passed, then the frame is terminated and the elapsed time to the event is the time frame duration. Otherwise, when a time period of 50 ms has elapsed, the speech frame is terminated and defined to be 50 ms in duration.

3) An average vocalized pitch period of the user, taken during a training session (or normal speech) using a series of voiced words and phrases, is used as the default timing period for the unvoiced speech segments. The unvoiced period can be a non-integer multiple of such an average-defined time frame duration.

A method of defining slowly varying unvoiced speech is to analyze the unvoiced acoustic spectra every 10 ms (or user chosen minimal sampling period) to determine the degree of change per sample time. If the changes in spectra are slow or of low amplitude, then the longer time scale spectral variations can be characterized by a few parameters that characterize slowly varying noise spectral weights, the shorter term changes can be modeled by a few "dither-rate" spectral composition parameters, and the overall on-off amplitude envelope by an on-rate and off-rate parameter. These values, carried with the fundamental noise spectral values, can be formed into a single feature vector that characterized a time frame describing a relatively long segment of unvoiced speech.

Combined Voiced and Unvoiced Speech:

A small number of speech sounds are generated by using both a voiced and unvoiced excitation function. An example is the word "lazy" (see FIG. 15) which transitions from a voiced-vowel sound of the phoneme /e/ (i.e., the "a" in lazy), to the voiced /z/ which includes an additional fricative excitation in the oral cavity, and the word finishes with an /i/ sound. In those cases where two excitation sources are in play, the following procedure is used. The voiced excitation is first measured and deconvolved from the acoustic signal. However, since the Fourier transform of the transfer function still contains wide band spectral-power caused by the modified white-noise of the unvoiced sources, it may be removed as needed. Three procedures are available to detect, process, and code such signals:

1) The transfer function is tested for a noise spectrum which has an abnormally high frequency pattern showing it is not caused by normal pole or zero transfer function filtering of the vocal tract. If noise is detected, its spectral character is used to select an unvoiced excitation function for storing in the feature vector. Using the identified source, then a second deconvolution of the transfer function is taken to remove the influence of the unvoiced excitation function. The feature vector is formed for the time period and it includes descriptions for two excitation functions as well as the twice deconvolved transfer function, acoustic data, prosody parameters, timing, and control numbers for the application at hand.

2) The voiced excitation function is measured using EM sensors, and is deconvolved from the acoustic signal. No special test is used to determine the unvoiced noise spectrum. The resulting transfer function is fit with a predetermined functional and the nonvoiced excitation function is incorporated as part of the fitting. The result may have a higher-than-normal high frequency background in amplitude vs. frequency space. The coefficients are stored in the feature vector for the speech time frame. This procedure is adequate for most applications except those where very high fidelity synthetic speech is required. A variant on this method is to purposefully incorporate a noise functional into the transfer functional that is used to obtain a numerical fit to the deconvolved numerical transfer function.

3) Use one or more additional EM sensors to detect the conditions of the vocal tract that may lead to a nonvoiced excitation. For example if EM sensors, measuring the tongue-position, indicate that the tongue body is closing the vocal tract against the palate behind the teeth, the tongue is in a position to cause turbulent air flow. An example is the unvoiced sound /s/, which with voicing added, becomes a voiced-fricative sound /z/. By using knowledge of the voiced excitation from the glottal sensor and tongue location, the algorithm can select the correct transform and deconvolve it from the acoustic waveform transform and test for noise presence. The next step is to test the transform for the noise spectral shape. If present, remove it with a second transform as in 1) above. This provides an acoustic transfer function transform, together with excitation function coefficients for forming a feature vector. This method is valuable because the user may not need to test every speech frame for the voiced/unvoiced excitation conditions. Yet, when it occurs, the method accurately performs the characterization as it is needed.

Transfer Functions:

The excitation of the human vocal system is modified by the filtering properties of the vocal tract to produce output acoustic speech. The filtering properties are mostly linear and are understood (for the most part). They can be described by linear systems techniques, as long as the necessary data is available. Traditional all-acoustic procedures do not provide the needed data. The methods herein obtain the necessary data and process it into very accurate descriptions of the vocal system for the first time. In addition, the methods obtain the data rapidly, in real time, and describe the human transfer function by a small number of parameters (i.e., coefficients) for each speech tract configuration. Additionally, the methods herein describe aspects of the human vocal-tract transfer-function that are important for speech quality but that are not well understood by experts. They enable a description of rapidly changing vocal tract configurations associated with rapidly articulated speech. They can obtain both the resonances and the antiresonances of the speech tract filter function (i.e., the poles and zeros of the transfer function), and information in real time, in frequency-space, or using combined descriptions. They also make possible the description of non-linear response as well as linear response transfer functions, because the output as a result of input can be stored in tabular form.

ARMA technique:

The transfer function can be obtained using a pole-zero approximation technique called the ARMA (auto regressive-moving average) technique, which makes use of time series or Z transform procedures well known to the signal processing community. This method of speech coding, using ARMA, provides a very convenient, well defined mathematical technique to obtain the coefficients defining a transfer function. Such a transfer function describes the vocal tract for each defined speech time frame. The ARMA deconvolving method includes obtaining substantially simultaneously, EM sensor and acoustic information, including amplitude, phase, intensity, and timing. In particular, the method provides a feature vector describing the transfer function by using the poles and zeros of the pole-zero ARMA description for the speech time interval frame or frames being coded. Alternatively, one forms a feature vector describing the transfer function by using, as feature vector coefficients, the a and b values of the a/b value description. (For signal processing references see Oppenheim and Schafer "Discrete-Time Digital Signal Processing" Prentice-Hall 1984", or Peled and Liu, "Digital Signal Processing: Theory, Design, and Implementation" Wiley, 1976). The poles and zeros describe the locations of the vocal tract filter resonances and antiresonances. The methods herein provide fundamental information, for the first time, describing the transmission "zero" frequencies of the vocal tract. The pole and zero values, or alternatively the a and b values, give the relative contributions of the resonances and antiresonances of the human vocal tract to the output acoustic signal.

For example, an ARMA functional was used to select 10 zeros and 14 poles for the sound /ah/, by using a least squares fitting routine. FIGS. 9A,B show first the measured simultaneous acoustic and vocal fold EM sensor signal. The vocal tract Fourier transform is obtained by first taking the acoustic transform, see FIG. 10A, and dividing it by the EM sensor glottal function transform, shown in FIG. 10B. The deconvolved result is described by a series of complex numbers, or amplitude and phase values. The transform amplitude versus frequency, for the time frame, is shown in FIG. 11A. A 10 zero, 14 pole ARMA model was then fit to the resulting vocal-tract transfer-function. FIG. 11A shows the numerical fit of the data to the ARMA functional, and FIG. 12B shows the pole/zero values that fit the phoneme /ah/. FIG. 11B shows a similar fit to the phoneme /ae/.

A feature vector for the speech time frame, during which a male speaker said the sound /ah/, was formed by obtaining, processing, and storing the information needed to characterize the acoustic speech unit to the accuracy desired, and is shown in FIGS. 12A,B. The feature vector includes several types of information. It includes the type of transfer function used. It indicates whether the segment includes a single phoneme or multiple phonemes. It provides phoneme transition information, for example the degree of isolation from previous and following phonemes. It describes the total time of constant excitation and counts the number of frames in the total vector. It also includes a description of the excitation function using the Fourier amplitudes and phases of the fundamental and the harmonics. This feature vector uses a predefined ARMA functional based upon the pole and zero value coefficients shown in FIG. 12B. An alternative functional description for the ARMA approach could have used the "a" and "b" coefficients, shown in FIG. 12C. Normalization and quantization methods were not used to form the feature vector in FIG. 12A.

For the first time the user can capture the essence of an individual speaker's voice to a very high accuracy, because the user of the methods herein is able to approximate the actual data to a very high degree of accuracy. The approximation process is conducted consistent with the information content in the original signals and consistent with the numerical methods used in the functional definition processes. The ARMA method described here allows the user to capture filtering, resonance and antiresonance, and feedback effects that have not been previously available to the speech community, but which are known to be necessary to capture human voices (e.g. especially women's and children's voices). Examples of structures that characterize an individual's voice are known to be associated with complex nasal structures, non-circular vocal tubes, tissue compliance effects, mucous layers, feedback effects on membranes, and other acoustic physiological interactions.

Predefined and Constrained ARMA Functionals:

Once the ARMA functional representation is obtained to the satisfaction of the user (depending upon the speech application and market), the user can "freeze" the functional representation for use for all work in a particular application environment. For example, the 14 pole, 10 zero ARMA functional may be the best one to use for a general purpose speech recognition application; but a different functional or set of functionals (e.g., 20 poles and 10 zeros for voiced nonnasal sounds, or 8 poles and 10 zeros for closed mouth voiced nasals) might be better functional choices for another user's application. The user could choose to take data from many speakers of a similar type (e.g. adult male American English speakers) using a fixed functional, but with differing pole and zero locations and with differing a and b coefficients reflecting their physiological differences. For many applications, the user will choose to average the defining parameters for the functionals and use them in a reference feature vector for code book formation. The user could also decide to use a training or adaptive process by which the system measures key physiological parameters (e.g. total tract length) for each speaker, and uses these data to predefine and constrain the primary poles and zeros for each speaker. Using processes defined below, these pole-zero values can be normalized to those obtained from a reference set of speakers.

The user can use the procedures, and through experimentation define "More-Important" and "Less-important" poles and zeros in the ARMA expansion (where importance is a function of the application and value). "More-important" values are fixed by the well known major tract dimensions (e.g., glottal to lips dimension and mouth length and area)

which are easily identified in the transfer function data and fit by automatic means. These values may vary from individual to individual, but their pole and zero positions are easily measured using the procedures herein. "Less-important" refers to those pole or zero terms whose contributions to the numerical fitting of the data are small. (One can use the "a" and "b" coefficients similarly). These "less important" (higher order) poles and zeros are associated with the individual qualities of each speaker, and thus their values are very dependent upon the special qualities of an individual's tissues, tract shapes, sinus structures, and similar physiology that are very difficult to directly measure. This method of dividing the coefficients describing the transfer function into "More-Important" and "Less-important" categories makes it possible to generate feature vectors that are simplified and useful for communications. For example, only the "More-Important" values need to be sent each frame and the "Less-important" values can be sent only once, and used to complete the feature vector at the receiver end of a vocoder to improve the speaker's idiosyncratic qualities. Similarly, only the "More Important" values need be sent, thereby minimizing the bandwidth needed for transmission.

Finally one can associate (develop the mapping) from the ARMA parameters to the parameters that are associated with physiological, circuit analog, or other models which may be easier to use for real time computations than the ARMA approach. These other procedures are described below. This procedure is known to work because the ARMA "b" coefficients represent the signals reflected from the pre-defined vocal tract segments, and the "a" coefficients can be associated with zeros of known and unknown resonances. The signal reflections from vocal tract segments can be related to reflections from circuit mesh segments, or physiological tract segments. The engineering procedures for making such transformations from reflections to circuit parameters are well known.

The constrained functional method makes use of speaker training to limit the values of the poles and zeros (or a and b coefficients) to be near previously measured values. These constraint conditions are obtained by initial training using phoneme sounds that are well known to be associated with known vocal tract conditions. Adaptive training using a speech recognizer can also be employed to identify phonemes to be used for the definition phase. Physiological parameters are extracted from the transfer functions of phonemes chosen for their close association with certain tract configurations. An example is to use the voiced phoneme /eh/ which is a single tube tract from the glottis to the lips; its primary transfer function resonance location provides a physiological measure of the speaker's tube length. With the total length known from the sound /eh/, the sound /ah/ allows the user to automatically define the division of the total tube length into the two sections from the glottis to the tongue hump. A series of these procedures are used to determine the dimensions of the vocal tract. Once these values are known, they can be used to constrain the ARMA functional variables during each natural speech frame. This process leads to faster convergence of the method to obtain the feature vector coefficients, because only a small number of fitting parameters need be tested against the data from each speech frame. In addition, these physiological parameters contribute numerical dimensions describing each individual speaker's vocal tract which contributes to speaker identification.

ARMA feature vector difference coding:

The difference feature vector method of coding allows one to define a feature vector by storing differences in each feature vector coefficient, $c_n$. The differences are formed by subtracting the value measured and obtained in the frame under consideration from the same coefficient formed during a previous time frame. For minimum bandwidth coding (also speech compression) the comparison is usually to values obtained during an earlier frame in the same segment when the algorithm noted that one or several important coefficients stopped changing. For the application of comparing a user's speech to that of a reference speaker or speakers, the reference feature vectors are obtained from a codebook using an additional recognition step. This method of forming such difference feature vectors is valuable because it automatically identifies those coefficients, $c_n$, that have not changed from a present frame to a reference frame. Consequently the information needed to be transmitted or stored is reduced.

If the reference values are predefined for the application, a complete difference vector can be formed (except for those control and other non-changing coefficients). Examples of reference speaker's feature vectors are those that describe the acoustic speech units of an American English male speaker, an American English woman speaker, or child, or a foreign speaker with a typical dialect when speaking American English. The identification of the type of speaker makes possible the selection of appropriate functionals for more effectively coding the user's speech. Similarly, the speaker's own coefficients can be measured at an earlier time and stored as a reference set for identification applications at a later time. However if an application such as minimum information generation, is being used, a "mixed" algorithmic approach can be chosen by the user, wherein a complete, new coefficient value is stored in the vector location in the first time frame it appears, and then in the following sequence of time frames that show no change or slow change of the coefficient, only a zero or small change value is stored.

The procedure of forming difference vectors is conducted on each speech frame. The processor automatically compares the obtained feature vector to the defined reference vector, subtracts the differences for each coefficient and stores the differences as a new difference feature vector. This procedure requires that the reference procedure be previously defined for the acoustic speech unit vector under consideration.

The simplest method subtracts the appropriate feature vector coefficients obtained in the present time frame $t_i$ from those in a frame measured at an earlier time $t_{i-q}$. Each coefficient difference, $\Delta c_n$, is placed in the "n" location of the difference vector for time frame $t_i$.

$$\Delta c_n(i,i_{-q}) = c_n(t_i) - c_n(t_{i-q})$$

In the special case that q=1, and if the coefficient difference $\Delta c_n$ is less than a predefined value, a zero value can be assigned to this nth coefficient in the difference feature vector, e.g., $\Delta c_n(i,i-1)=0$. Similarly, differences of vector coefficients from values stored in vectors from any preceding or following time frame, e.g. $t_{i-q}$ for q<i as well as for q>i, are straightforward to generate, and, if needed, can be tested for difference value levels.

For reconstruction, the identically zero value tells a subsequent application algorithm to look to the first preceding time frame, e.g. $t_f$ with f<i-q, in which the examined feature vector coefficient, $c_n(t_f)$, is non-zero. Upon finding a non-zero value, the coefficient value $\Delta c_n(t_f)$ is substituted for $c_n(t_i)$ for use by the subsequent application. If the application algorithm needs absolute values of the $c_n$'s, then the full value feature vector must be reconstructed by using the predefined decisions for first finding the reference coefficient value. When using the difference vectors, the algorithm adds the difference coefficient value from the difference vector to the reference coefficient value to generate the coefficient $c_n(t_i)$, in the frame under consideration.

In the application where the measured coefficient vector values must be compared to those of a reference vector coefficient, two approaches are possible. Either known speech segments are spoken by the speaker for which references have been previously recorded, or a speech recognition step must be employed to first identify the feature vector under consideration and to then find the associated reference feature vector. In this way the subtraction of coefficients can occur and difference coefficients can be used to form a difference vector describing the acoustic speech unit or units in the time frame.

This method of differences is valuable to minimize the amount of information needed for storage or for transmission because many of the vector coefficients will be zero. Consequently they will take less storage space, computation time, and transmission bandwidth. The absolute feature vector for the speaker can be reconstructed at a later time as long as a definition standard for the coefficient zeros (or other no-change symbols) is known or is transmitted along with the feature vector, e.g. the identical zero code described above. An example of importance to telephony is to first store a standard speaker's feature vector values, for all phonemes and other acoustic units needed in the application. These data are placed in both the recognizer processor and in the synthesizer processor codebooks. Then, whenever an acoustic speech unit is to be transmitted over the medium, only the unit symbol and the deviations of the user speaker from the reference speaker need be transmitted. Upon synthesis, the average speaker coefficients stored in the receiver, plus the deviation coefficients, form more accurate vectors for reconstructing the text symbol into speech.

Another important application is that this automatic method of determining deviations from standard speakers saying known sounds, enables algorithms to self adapt the system. When certain reference sounds are pronounced and certain difference vector coefficients exceed a predetermined level, the algorithm can trigger an automatic "normalization" of the speaker's feature vector to that of a reference speaker for more accurate recognition or other applications. Conversely, if the differences become too large, over a short time period, the algorithm could signal appropriate persons that a personnel change in the user of the system has occurred.

Electrical Analog of the Acoustic System:

The excitation function and the transfer function may be approximated as defined above, using well known electrical analogs of the acoustic system. See Flanagan 1965 for an early, but thorough description. FIG. 16 shows a simplified electrical analog of the human acoustic system showing an excitation function, a vocal tract transfer function impedance, and a free air impedance. By fitting the circuit parameters of the equivalent electrical circuit, each time frame, to the measured excitation function and transfer function data, automated algorithms can determine the "circuit" parameter values. The advantage of this approach is that the relatively small number of types of human vocal tract resonator conditions (10 to 20) can each be modeled by a set of circuit elements—with only the specific parameter values to be determined from the speech information each time frame.

For example, FIGS. 17A,B show an electrical analog of a straight tube human acoustic system with electrical analog values, e.g., the L, C, R's, which represent the acoustic coefficients of a single tube system which is used for the acoustic speech sound /ae/. Using the deconvolving approach illustrated in FIG. 5 and using the transfer function values in FIG. 11B, the impedance values shown in FIG. 16 and the circuit values shown in FIGS. 17A, B can be determined for the sound /ae/ using algorithms to fit the circuit values to the transfer function data. Feature vector coefficients can be defined by using the electrical-analog transfer function as the functional representation and by using the electric circuit parameters to represent the transfer function. The parameters are easily fit to the well defined transfer functions because the methods herein show how to separate the excitation source from the vocal tract transfer function in real time for each speech time segment. In addition to the methodology of forming a feature vector, the electrical analog circuit parameter values are useful in describing the physiological vocal tract values because the L's represent air masses, the R's and G's represent acoustic resistance and conductance, and the C's represent air volumes. These physiological parameters can also be used as feature vector coefficients.

For the single mesh circuit in FIG. 17A, the air volume velocity transfer function between glottal and mouth is given by the following expression, which includes radiation load:

$$\frac{U_m}{U_g} = \frac{\cosh(\gamma_r L)}{\cosh(\gamma + \gamma_r)L}$$

where $\gamma$ and $\gamma_r$ are related to the mesh circuit parameters as given in FIG. 17A and are defined as:

$$\gamma = \sqrt{(G+j\omega C)(R+j\omega L)} \ ,$$

$$\gamma_r = \frac{1}{L} \tanh^{-1}\left(\frac{A_t}{A_m}\left[\frac{(ka)^2}{2} + j\frac{8ka}{3\pi}\right]\right)$$

At and Am are the area of the throat and mouth opening respectively, and k is the wave number of the sound, and a is the radius of the mouth opening. For the case of a simple tube such that $A_t = A_m$ (i.e., the case of equal glottal and mouth area) the poles of the transfer function are given by:

$$S_n = F(a,L)\left[-\left(\alpha c + \frac{a^2\omega^2}{2Lc}\right) \pm j\frac{(2n+1)\pi c}{2L}\right]; \quad (1)$$

$$n = 0, 1, 2, \ldots$$

where $$F(a,L) = \frac{3\pi L}{3\pi L + 8a}$$

The physical parameters in Eq. (1) are: L, the vocal track length; a, the mouth opening radius; and $\alpha$, the vocal tract wall resistance. Typical numbers are: $F(a,L) \sim 0.94$; $a \sim 5.2e^{-4}$ $cm^{-1}$; and the speed of sound $c = 3.5e^4$ cm/sec. The low order poles can be determined. They can be used to constrain the physiological variables using the equations below. The three physical parameters can be estimated from measurements of the first two pole locations on the S-plane. They are $r_0$, $r_1$, $\omega_0$, and $\omega_1$, the corresponding real and imaginary parts of the first two poles of the transfer function. Then the three physical parameters can be determined from the following relations:

$$a = \sqrt{\frac{2\pi c^2 |r_0 - r_1|}{(\omega_1 - \omega_2)(\omega_1^2 - \omega_0^2)}} \quad (2)$$

$$L = \frac{1}{3\pi}\left(\frac{3\pi^2 c^2}{(\omega_1 - \omega_0)} - 8a\right). \quad (3)$$

and $$\alpha = \frac{1}{c}\left(\frac{r_1(3\pi L + 8a)}{3\pi L} - \frac{a^2 \omega_1^2}{2Lc}\right) \quad (4)$$

Physiological Parameters:

The methods used for obtaining the information described above can be used to generate a feature vector using the physiological parameters of the human speaker vocal tract as the coefficients to describe the acoustic speech unit spoken during the speech time frame. The transfer function parameters used to define the ARMA models, the electrical analog model values, and those obtained from real time techniques described herein, define physiological parameters such as tract length, mouth cavity length, sinus volume, mouth volume, pharynx dimensions, and air passage wall compliance. In addition to the physiological parameters, the feature vectors would contain, for example, the excitation function information, the timing information, and other control information.

One can then use this physiological information as coefficients of a feature vector, or they can be include in the ARMA or other transfer functional forms to constrain the coefficient values. For example, once one knows the tract length from glottis to lips by saying the phoneme /ae/, one knows the basic resonance of the speaker's vocal tract and it serves as a constraint on data analysis by defining the lowest frequency formant for the speaker.

An example of the data that is available using the methods herein is to use the pole zero numerical fit to the transfer function data for the sound /ae/ shown in FIG. 11B. The lowest formant pole, $f_1$, is at 516 Hz, and using the simple expression, neglecting the radiation term, one finds the vocal tract length:

$$L = \frac{c}{4f_1} = \frac{3.5e^4 \text{ cm/sec}}{4 * 516} \cong 17 \text{ cm}$$

Similarly, the pole zero data for the sound /ah/ in FIG. 11A provides the data for the glottis to tongue hump plus tongue hump to lip data.

An important application of the physiological values is that they provide a method to normalize each unique speaker's transfer function to that of an appropriate average speaker. In this manner, each formant value, obtained through deconvolving methods herein, can be transferred to a new value by using measured physiological values and instant reference values.

Another important use of physiological parameters is to measure the glottal and vocal fold mechanical properties as phonemes are voiced. The EM sensor that measures the glottal structure motion, enables the user to constrain the mechanical values of the glottal mechanisms. These values include opening amplitudes, spring and mass constants from the pitch, and damping, and compliance from sympathetic tissue vibration due to backward propagating acoustic waves (i.e., low pressure acoustic waves). Special phonemes are chosen for calibration purposes, such as those with the low post glottal pressure (e.g., open tube phonemes) like /uh/ or /ah/.

The differences in physiological conditions and in excitation functions for well known phonemes allow an automatic identification of several attributes of the speaker. This can be used for identification purposes as discussed above, but also can be used to automatically select the best types of transfer functional forms to be used to fit each user's physiology. Examples are to identify gross features of the speaker vocal tract dimension, e.g. an adult male, an adult female, a child, and other variations well known to the speech practitioner.

Speech Coding:

The purpose of recording and coding EM sensor and acoustic information is to use it for specific user defined applications. The methods herein include processes to define the characterizing parameters for a variety of physical, engineering, and mathematical models that are valuable and useful for all EM sensor/acoustic based speech technologies. They include processing procedures, which include time frame definition, coefficient averaging, normalization, quantization, and functional fitting to convert the EM sensor/acoustic data to form feature vectors. These methods are mostly linear procedures, but are not limited to linear techniques. Examples of nonlinear procedures include, but are not limited to, taking the logarithm of the acoustic data or the transfer function to reflect the human hearing function, or to compress the frequency scale of the transformed data in a linear or nonlinear way (e.g., "Mel" or "Bark" scales) before the functional fitting techniques are used. Such processing depends upon the application. Feature vectors for appropriate time frames can be formed by fitting linear or nonlinear functional coefficients to the processed data, and such feature vectors can be stored into code books, memories, and/or similar recording media.

The vast amount of data generated by the methods herein, measured over a wide frequency range for every speech frame, enable the definition of the coefficients used to fix the functional forms into functions that fit the data. For example, the EM sensor data shown in FIGS. 9B and 10B for the phoneme /ah/ was generated at 2 MHz and the simultaneous acoustic data (FIGS. 9A and 10A) were digitized at 11 kHz (using 16 bits). This provides 250 EM data points per acoustic point, which are averaged to match the accuracy of the 16 bit acoustic data. In each nominal 10 ms speech frame, this leads to 80 averaged data points per EM sensor and 80 acoustic data points to define a set of functional coefficients. In principle between 80 and 160 unknown coefficients can be determined. However experts skilled in the art of fitting functional forms to data know how to use such large data sets to define a smaller number of coefficients associated with simpler model-based functional-forms. In particular, the flexibility of the techniques described herein make it possible to design the EM and acoustic data collection systems that work well over a very wide range of data accuracy and detail.

Single- and Multi-Time-Frame Feature Vectors

Using the methods herein the user can describe the excitation function, the transfer function, the speech time frame parameters, acoustic parameters, prosodic information such as pitch or amplitude envelope shapes (obtained during one or a series of time frames), and control information (e.g. types of transfer functionals and frame clock times). The user can easily assemble this information into a feature vector for each speech time frame. These individual time-frame feature-vectors can be joined together to describe concatenated vectors describing several acoustic speech units occurring over two or more time frames (e.g. diphoneme or triphoneme descriptors). Such a multi-time-frame feature-vector can be considered as being a "vector of vectors". These multi-time-frame feature vectors can be constructed for all phonemes, diphonemes, triphonemes, multiphonemes (e.g. whole words and phrases) in the language of choice. They can be stored in a data base (e.g., library or code book) for rapid search and retrieval, for comparison to measured multi-time-frame feature-vectors, and for synthetic speech and other applications. The capacity to form a feature vector describing the variations in speech units over many time frames is valuable because the time varying patterns of the sequences of the individual vector coefficients are captured by the corresponding sequence of speech frames. This approach is especially valuable for storing diphone and triphone information, and for using Hidden Markov Speech Recognition statistics on defined sequences of many (e.g., 10 or more) acoustic speech units.

A specific example of describing a long duration, multiphoneme speech segment is to "sample" and define the feature coefficients every time a change in coefficient condition is detected, as described above for single time frame vector formation. At each time of condition change, $t_i$, a feature vector of p coefficient values, $c_n(t_i)$, where n=1 to p, is obtained (see FIG. 12A). This procedure produces a sequence of sets of feature vector coefficients that are obtained at the specific times of change noted by the values $t_1, t_2, \ldots, t_i, \ldots, t_k \ldots$ For example, the time values, $t_1$, denote the start time of the speech frame. However the $t_i$'s can also denote a sequential frame number noting the frame position in a sequence of frames. Because the time frame duration is usually included in the feature vector as the pitch period or the number of pitch periods (or other notational forms), the total time taken by a frame or a sequence of frames (i.e., comprising a speech segment) can be reconstructed. For example, below is a set of sequences of p coefficients $c_1(t_i)$, $c_2(t_i)$, $c_3(t_i)$, $\ldots c_p(t)$ for each start time $t_i=t_1, t_2, \ldots, t_k$.

$$c_1(t_1), c_2(t_1), c_3(t_1), \ldots c_p(t_1), c_1(t_2), c_2(t_2), c_3(t_2), \ldots c_p(t_2), \ldots, c_1(t_k), c_2(t_k), c_3(t_k), \ldots c_p(t_k)$$

This method describes an adaptive procedure for capturing the essential speech articulator information throughout a speech segment, without requiring a frame definition every 10 ms as many acoustic (CASR) recognition systems do. These patterns of coefficient sets form a multi-time-frame feature vector that describes an entire speech segment that begins at time $t_1$ and ends at time $t_k+$ (last frame duration time). Such vectors, which can include pause times (i.e., silence phonemes) are very unique for each speaker. They time compress the coded speech information, and they store all of the information needed for the application by choice of "change" condition definitions, and by choice of sensors, accuracies, and other considerations described herein.

Normalization and Quantization:

Normalization:

The methods described herein can code any type of acoustic speech unit, including coarticulated or incompletely-articulated speech units. The coding methods provide very high quality characterization of each spoken phoneme for each spoken speech segment, but if the articulation of the user-speaker is different from those speakers whose acoustic speech units, or sequences of speech units, were used to generate the reference code book, then the recognition or other process loses some accuracy. The unique ability of the methods herein to characterize the physiological and neuro-muscular formation of each speakers articulators makes it possible to normalize each unique speaker's transfer function to that of an appropriate reference speaker. These normalization methods reduce the variability of the feature vectors formed during each time frame by normalizing the feature vector coefficients (or sequence of units) to those of a reference speaker or speakers.

During a training session, the user speaks a series of speech units or speech unit sequences into systems like those shown in FIGS. 3A,B. A group of feature vectors are selected by asking the user to speak a desired vocabulary, or by using speech recognition during natural speech to select the desired vocabulary. The coefficients of each speech vector, for every selected speech time frame, are compared to the feature vector coefficients from the same reference words generated by a reference speaker at an earlier time. In this way, all the feature vectors for the acoustic speech units needed in the reference vocabulary are measured and placed in a reference codebook at an earlier time.

The process begins as the algorithm compares each measured vector coefficient, $c_n$, to that of the reference speaker each time frame. If it differs by a predefined level (e.g., a user chosen 20% value), then either the coefficient in the reference codebook or the one in the speaker's feature vector is to be changed. This process of normalization is carried out for each speech time frame, using one of the three following methods:

1) Codebook Modification: All feature vectors listed in the codebook and which relate to the tested acoustic speech units in the limited vocabularies, have their coefficients changed to be those of the speaker specific feature vector. Also included is a process for altering those multi-phone sound-unit sequences in the code book, which contain individual word sounds in need of correction. Acoustic sound units that are correctable, e.g. phonemes, diphonemes, and triphonemes, contain coefficients that are often associated with "misarticulated" phonemes. The specific coefficients of the multiphone feature vectors are altered to reflect the idiosyncratic articulation of the associated single speech unit as determined during training. For example if the speaker misarticulates the sound /th/ as in "the", then all diphonemes, triphonemes, etc. that have /th/ in them such as /th/ /a/ /t/ in the word "that" are corrected to the speaker's feature vector. Similarly, multiphoneme units can be spoken, compared, and changed in the codebook as defined by this algorithmic prescription. This procedure leads to the construction of a speaker specific codebook.

2) Key Sound-Sequence Modification: During the training session, the speaker articulates special acoustic sound sequences that are known to be poorly pronounced by speakers of the language. The acoustic sound unit sequences are measured using methods herein and feature vectors are formed. The measured feature vector coefficients for these multi-unit articulator conditions are stored in place of similar feature vector coefficients in the predefined codebook locations. This provides a partially "individualized" multi-phoneme codebook.

3) Method of Extremes: The speaker says a series of training acoustic speech units that require the speaker to use his articulators in their extreme positions or rates (e.g., highest to lowest position, fastest to slowest rate, front-most to back-most position). By finding the feature vector representations for these extremes, using both direct EM sensor methods and the deconvolving methods, one obtains two extreme limits on the coefficients describing each feature vector coefficient. The extreme coefficient values, for each coefficient $c_n$ are represented by $_{min}c_n$ and $_{max}c_n$. These two extreme values can be used, for example, to represent the longest and shortest vocal fold periods and the largest and smallest of each transfer function coefficient for acoustic speech units. Other values, such as the average value of the extremes, $_{ave}c_n = (_{min}c_n + _{max}c_n)/2$ for each coefficient in the feature vector coefficient location, $c_n$, can also be obtained. These special values are stored in a separate, but "parallel"

codebook that contains the "user extremes", user averages, and other useful values that correspond to each user coefficient, $c_n$, that will be used in the formation of normalized feature vectors for the application.

The next step in the method of extremes is to generate the needed reference speaker extremes, averages, and other useful values as well. Each reference speaker (or speakers) is asked to articulate the set of identical sound units for the training cycle of the speaker being normalized. Next, the sets of reference coefficient extremes (as well as other information such as averages) are associated with each coefficient $c_n$ for each acoustic sound unit in the separate, but "parallel" codebook. An example of other useful values are those that represent special articulator conditions that define intermediate articulator coefficient values. These are valuable to aid in non-linear or guided interpolation procedures.

During normal usage of these methods, when the speaker speaks any sound unit, a time frame is defined and a feature vector is generated. Each measured coefficient, $_{meas}c_n$, of this feature vector is compared to the maximum ($_{max}c_n$) and minimum ($_{min}c_n$) range of the speaker's coefficient extension for this coefficient $c_n$.

The fraction of distance, $f_n$, of the measured coefficient between the two extremes of the speakers range is calculated, using as an example a linear approach as illustrated in FIG. 18:

$$f_n = {_{meas}c_n}/({_{max}c_n} - {_{min}c_n})$$

The coefficient $_{meas}c_n$ is then replaced with the coefficient $_{normal}c_n$ as follows, using the minimum and maximum ranges of the reference speaker.

$$_{normal}c_n = {^{ref}_{min}c_n} + f_n * ({^{ref}_{max}c_n} - {^{ref}_{min}c_n})$$

In this equation, $f_n$ contains the information from the user's own measured $c_n$ value, and from the "parallel" code book of extremes containing the user's and the reference speaker's extreme values (and other useful values) associated with each feature vector coefficient, $c_n$. In this way the fraction of the user's articulator coefficient range is mapped to that fraction of the reference speaker's range.

This procedure is very easy to implement because the acoustic speech unit in each time frame is characterized with a relatively small number of coefficient values that require normalization (e.g., a sub-set of the coefficients $c_1$ through $c_p$ in FIG. 12A). It is well known that other interpolation techniques for $f_n$ can be used as desired, besides the linear one described above. In addition, it is clear that control coefficients such as timing and phoneme symbols whose numerical values are contained in one or more of each feature vector's coefficient values are not normalized as described above.

The above normalization methods enable the user to correct for incomplete articulation because the feature vector coefficients associated with incomplete articulator positioning are normalized to the correct coefficient values articulated and recorded by reference speakers. In addition, coarticulation is corrected by normalization of multi-speech-frame vectors that describe diphonemes, triphonemes, and similar acoustic units where coarticulation most commonly occurs. It is important to note that the extreme values (i.e., target values) for each phoneme in a multiphone sequence as determined from a reference speaker or speaker group will be different than for individual phonemes or other primitive speech units from the same reference persons. That is, the speech organ articulators do not reach the same extreme values of $c_n$ associated with isolated phoneme they speak the same phonemes imbedded in di-, tri-, or higher order multiphones.

The voiced pitch value of an individual speaker is an important coefficient that can be normalized to those of the reference speaker or speakers as described above. The procedure is to normalize the appropriate excitation feature vector coefficient, $c_n$, which represents the pitch value (i.e., the reciprocal of the pitch period) of the speaker for the voiced speech frame under consideration. The pitch value extremes for both the speaker and the reference code book contain maximum pitch, minimum pitch, and intermediate pitch values as needed (e.g., a pitch value for each of the major vowel groups). The normalization of the excitation function pitch-value coefficient proceeds as described above for generalized coefficients.

Figure 18A:
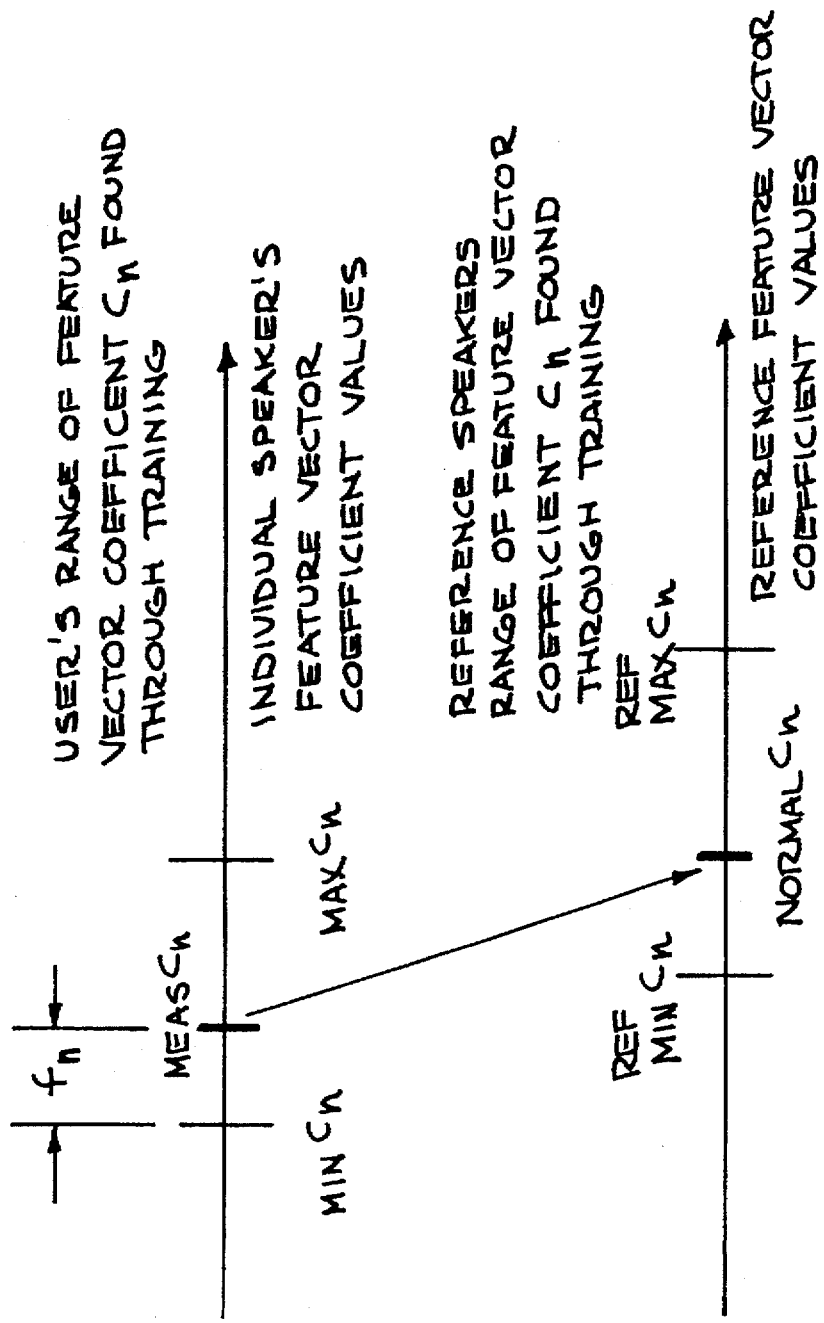
FIG. 18A shows a method of normalizing a speaker dependent feature vector coefficient, $_{meas}c_n$, to a normalized coefficient, $_{normal}c_n$.

Since a person's physiological tension level, as well as external stress or health factors, can change a user's pitch, rate of speech, and degree of articulation, it is important that they be corrected as often as the application allows. Daily pitch normalization is available using the first words a user speaks to turn on the machine or to "log in". Adaptive updating, using easily recognized vowels can be used to correct the maximum and minimum levels, as well as the intermediate normalization values as shown in FIG. 18A. As the day progresses, and the user tires or becomes stressed, adaptive correction based on automatically recognized acoustic speech units can be used.

Figure 18B:
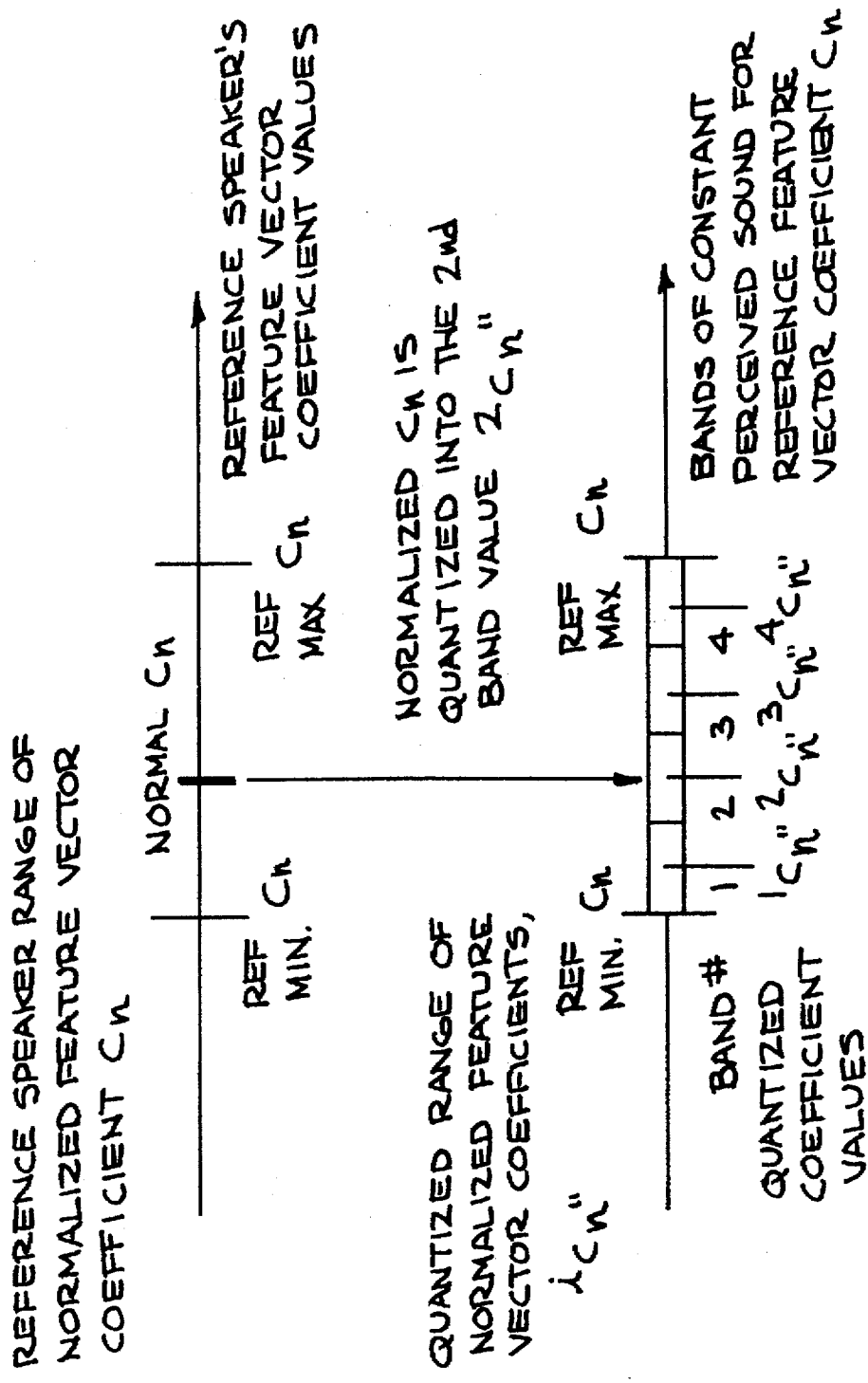
FIG. 18B shows a method of quantization of a normalized coefficient into one quantized value that represents a quantized band of coefficients, over which no important sound changes occur.

Quantization of Feature Vector Coefficients:

It is known from speech research that the vocal articulators must move or change some condition a minimal amount for a perceived change in the speech sound to occur. (See references by Stevens, "Quantal Nature of Speech: Evidence from Articulatory—Acoustic Data" in "Human Communication—A Unified View" eds. David & Denes, McGraw Hill, 1972.) Thus changes in the values of these feature coefficients and pitch values that do not cause a perceived difference in the application (e.g., recognition or synthesis) can be grouped together in a "band" of constant value. As a consequence, during training and synthesis experiments, the user can determine the bands of coefficient values, using a reference speaker or speaker groups, over which no perceptible speech changes are detectable for the application at hand. Once these bands of constant speech perception are determined, for each applicable feature vector coefficient, including excitation function coefficients, the measured coefficient values, $c_n$, can be quantized into the value of the band. As speech takes place, each measured feature vector coefficient is first normalized, and then "quantized" or "binned" into one of only a few "distinguishable" values. FIG. 18B shows such a procedure based upon the normalization procedures described above and illustrated in FIG. 18A.

The algorithm proceeds as follows. First, the feature vector coefficients are measured for each speech time frame. Second, each coefficient is normalized to a reference speaker's value for the coefficient as shown in FIG. 18A. Third, each normalized coefficient value is quantized into one value that represents a band of constant acceptability over which the coefficient can vary in value, but produce no discernible change as defined by the user. Thereby a continuum of coefficients can be mapped into only a few values, representing a few bands. The band coefficient value is usually chosen as the central value of the band. If the normalized coefficient, $_{normal}c_n$, is in the range spanned by the second band of the reference speaker's discernible bands, then the measured value $_{meas}c_n$ is mapped first to $_{normal}c_n$, then into the quantized value $^2c_n$". The double accent" means the coefficient is quantized and the superscript 2 refers to the second of the bands spanning the total range of the normalized feature vector coefficients $_{normal}c_n$.

If the user wishes, quantized band values obtained during reference generation and during use can be further normalized. For example each of the n bands can be associated with a fractional value ranging from 0 to 1 (or over another range of the user's choice) for numerical convenience. For example, it may be desirable to quantize pitch rate into 3 values, such as 1, 2, and 3, representing low, middle, and high frequency pitch of any speaker, and to not use absolute pitch frequencies such as, for example, 70 Hz and 150 Hz, or similar physically meaningful values. This method of normalizing quantized values is valuable because it removes all apparatus and speaker specific values, and it enhances table lookup speed and accuracy.

Real Time Measuring, Recording, and Deconvolving:

The methods described herein permit the user to select the appropriate techniques for sensing, processing, and storing the information with an almost arbitrary degree of linearity, dynamic range, and sampling bandwidth for the desired application. They can be used in a variety of configurations depending upon the costs, the value of the data, and the need for portability and convenience. Because of the flexibility of these methods to meet the needs of a wide variety of applications they are very valuable.

The method of using real time information to relate excitation-source signal-features to related acoustic-output signal-features, is valuable for obtaining physiological information for several applications. For example, these procedures can be incorporated into a training sequence when a user first begins to use systems based upon the methods herein. By requesting the user to speak a known series of phonemes, the algorithm can be automatically adapted to the user (or by using speech recognizers that recognize key phonemes from which the desired timing information can be extracted). For example, the methods allow the determination of the acoustic tube lengths of an individual as known phonemes are spoken. The phoneme /ae/ is known to be caused primarily by a voiced, single tube resonance from glottis to lips to the microphone. The time it takes for an excitation signal to travel the length and appear as an acoustic signal can be measured and used to determine parameters used in the vocal models of an individual's speech tract. (see FIGS. 14A,B for an example of time duration). The knowledge of the length permits faster numerical model fitting, because one of the major tract filtering properties is constrained. It is also valuable in speaker identification, by providing a physiological measurement that contributes to the definition of a unique speaker.

Similarly, in other speech tract configurations, such as a nasal /m/, the sound travels from the glottis through the nasal passage, as well as into the closed mouth resonator. The sum of the two signals exits the nose to the microphone. An acoustic echo (canceling certain frequencies in the speech output) will be caused by the closed mouth resonator. Other phonemes are caused by similar combinations of tubes and resonators. The glottal excitation travels differing paths, have differing time delays. The real time methods described herein enable the measurement of these other tract dimensions as well.

This method provides for deconvolving, in real time, the excitation source from the acoustic output to obtain useful vocal tract information. The dimensions and other characteristic values of the user's vocal tract segments, obtained for each speech segment, can be used to form a feature vector to describe the vocal tract for subsequent applications. Experiments have provided physiological values for the phonemes /ah/ and /ae/.

Applications:

Speech Compression:

The methods provide a natural and physically well described basis for speech time compression. The methods defined above for difference feature vector formation, for multi-time-frame feature-vector formation, for multiple glottal period time frames, for slowly varying feature vector time-frames, and for unvoiced time frame determination show algorithmic descriptions of accurately coding speech segments using much less time than real time spoken speech. Simple extensions of these methods show how to collapse both the silence PLU e.g., pause speech segments) to one vector and relatively long unvoiced speech segments to one vector. These methods enable one to collapse time segments of essentially constant speech into one time frame and one representative (i.e., compressed) feature vector. The compressed vector contains only a few additional coefficients that describe how to "uncollapse" the speech back to real time as needed. Additional compression can be attained using grammatical and syntax rules that remove redundancy of sound patterns, such as a "u" always following a "q" in American English. These simplified patterns can be undone during speech synthesis, during reconstruction of transmitted speech symbols, or from speech stored in memory.

Speaker Identification:

The methods of feature vector formation herein enable a user to compare a feature vector from one or several speech segments to the same speech segments as spoken by a reference speaker, and stored in a codebook for the purposes of speaker identification. The coding and timing methods for this purpose can be performed automatically, by defining the feature vector over each time frame or sequence of time frames. The identification operation can be conducted using the feature vectors from isolated time frames or using multi-phoneme time segments. The user is able to make identifying comparisons using previously agreed upon speech segments (e.g., names or PIN numbers) presented to a user by the system for his vocal repetition. Alternatively, speech recognition can be used to extract key speech segments from natural speech. The identified feature vector patterns (i.e., multi-time frame feature vectors) are compared to those in the reference codebook.

In addition to the frame by frame comparisons against reference frames described directly above, additional information on the average pitch and the pitch variations of the user, the physiological parameters of the user's vocal organs, and the EM wave reflection strength from the user (tests water and tissue composition) are available. These parameters are obtained from initial sound requests to the user by the system and are initially obtained as the user "logs in". They are then used for comparison against values known, by the system, to represent the true speaker.

The identification process uses a measurement algorithm that compares the distance of the measured feature vector coefficients from those stored in the codebook each time segment. At a normal speaker's rate of speaking 5 to 10 phonemes per second, a twenty to thirty phoneme sequence, with time spacing and prosody values, can be obtained within a few seconds. For very sophisticated recognition as much as a few minutes of speech may be required; and for very high value work, continuous recognition may be employed using speech recognition for continuous key pattern identification and verification of the speaker throughout the use period. During the sampling time, statistical algorithms process the data and obtain the probability of correct identification.

In addition to the acoustic and EM sensor patterns, physical parameters of the user can be obtained using the methods herein. The physiology of the vocal organs such as sizes, positions, normal positions (e.g. normal pitch), and tissue compliances can be obtained. Also the quality of articulation of each acoustic sound unit, as well as the rates of formation are obtained. Each speaker's unique articulation qualities are exaggerated when combinations of rapidly spoken sounds such as diphonemes or triphonemes, etc. are measured and compared to previously stored data. The methods herein describe how such multiphone feature vectors are formed, measures of distance formed, and measures are used for comparison. The organ dimension, articulation positions, and their time patterns of motion in conjunction with acoustic speech information, taken over a sequence of acoustic speech sounds, are very idiosyncratic to each speaker of any language.

This method makes possible the use of the feature vector coefficients to define a distance metric between the user's characteristics and those defined when the validated speaker spoke the same acoustic unit from which the vectors were formed and stored in a pre-defined library. One example measurement process is to obtain the distance between all the measured and stored vector coefficients (control and other special coefficients excepted):

$$\Delta c_n(t_i) = _{meas}c_n(t_i) - _{ref}c_n(t_i)$$

for all time frames denoted by the time of the frame, $t_i$. The algorithm then takes the square root of the sum of the squares of all the coefficient differences, $\Delta c_n(t_i)$, for all speech time frames in the sound sequence. If the measure is less than a pre-defined value, based upon previous experiments by the user, the user speaker is accepted as validated. This example method is a uniform distance metric applied equally to all appropriate coefficients. Other methods which use non-uniform coefficient weighting methods, non-linear measure processes, and which use differing statistical testing are well known.

Other applications use similar comparison procedures that are made between the speaker and reference libraries of vectors with coefficients obtained from averaged (or other types of reference speakers) to determine the physiological or linguistic type of speaker. For example a male American English speaker, female American English speaker, child, or foreign speaker with a specific dialect can be identified for various purposes.

Language Identification:

The patterns of feature vectors vs. time (i.e., multi-time frame feature vectors) are very indicative of the language being spoken by the speaker. A method to determine the language being spoken by a speaker is as follows. It uses the procedures described above for speaker identification, except that a separate normalized (and quantized if need be) language codebook is previously formed for every language in the set of languages for use in the application. As the user speaks known test sounds, or by using real time recognition techniques to extract test sounds from the natural speech, the algorithm forms feature vectors for each speech period using the individual glottal period feature vectors as the basis. The vectors can be normalized and/or quantized as needed. The algorithm then forms these basic patterns into more complex patterns and it searches each one of the several language code books for the measured patterns. The patterns are chosen to contain the unique identifying sound patterns of each language. The algorithm then uses the statistics of appearance times of multi-time frame feature vectors, of specific vocal articulator positioning represented by specific or small groups of feature vector coefficients (especially glottal pitch patterns), and it searches for the appearance of those unique sound patterns associated only with a given language. Several methods of measuring multi-component vector distances, are available to test for the best fit and are described above in the section on speaker identification. When a best fit of the speech segments to one of the language codebooks is found, the language of speech is identified and the probability values of the recognition are available as needed.

Speech Recognition:

The methods described herein make possible the identification of all spoken acoustic speech units in any given language in a new and powerful way. This new type of speech recognition is based upon using the feature vectors defined above using processed information from the excitation function, the deconvolved transfer function, simultaneously recorded and processed acoustic information, and the timing information. The feature vectors are more accurate than those based upon acoustic techniques alone. The reason is that they are directly tied to the phonemic formation of sound segments. They are more accurate than other approaches because both poles and zeros can be accurately modeled, the pitch can be accurately and rapidly measured, and the feature vector coefficients can be readily normalized and quantized, removing speaker variability. The vectors describe the condition of a speech unit with sufficient information, including redundancy and model constraints, that the phoneme (or other acoustic speech units) can be defined, with very high probability, in an automated fashion for each speech time frame. An identification results when the measured and processed phoneme feature vectors from a speech segment are associated with a stored reference vector containing the symbol or symbols of the acoustic speech unit. The acoustic speech unit identification results in a recognized symbol (e.g., a letter, pictogram, series of letters, or other symbol). Once the speech segment's identification symbols are available, they can be automatically coded to ASCII (or other computer coding) or to telephony codes for transmitting letters, pictograms, or text symbols over communications channels. Such procedures to convert recognized acoustic speech symbols into "technological codes" are known to practitioners of communication technologies.

Methods for normalizing tract feature vectors and excitation functions, for time independent acoustic description, for normalizing rates (i.e., time warping), for dealing with coarticulation, incomplete articulation, and phoneme transitions can be used to simplify the variability of measured patterns of speech information between individuals and by the same individual at different times. These make possible more rapid and accurate code-book "look-up" of the correct acoustic-speech -unit symbol.

Training, Table Lookup and Table Generation:

A training process is used by algorithms described herein to ask a speaker (or speakers) to articulate a known vocabulary of speech segments into a system similar to one shown, for example, in FIGS. 3A or 3B, 8, or 20. The segments can range in complexity from single phonemes to continuous natural speech. The training process enables one to build up known associations of measured feature vectors with symbols for known acoustic speech units by using the instruments shown in the representative systems and the methods described herein. The system designer can select the appropriate processing algorithms from those described herein, including normalization, quantization, labeling and other necessary operations to form and store the feature vectors for each trained sound segment into a code book location or library locations (i.e., a data base). These code-book data-sets serve as references for most of the applications described herein. Methods of associating a measured speech feature vector with a similarly formed set of vectors in a code book make use of well known procedures for data base searches. Such procedures allow the algorithm to rapidly find the locations in the data base where the measured vector matches stored vectors. Procedures are described and to rapidly calculate vector distances to determine the best match, and to determine probabilities of association. Accurately formed feature vectors, normalized and quantized, allow for very rapid data base searches.

An EM/Acoustic Template Matching Model for Speech Recognition:

The feature vectors can be used for phonetic template (i.e., pattern) matching and associated acoustic speech unit identification. Each acoustic speech unit symbol is uniquely associated with a specific articulator configuration (i.e., a phonetic articulator pattern). The formed vectors, which describe these patterns, are then compared against the library data and an identification is made using the "distance" from the code book feature vectors, and using logical operations, such as "on" or "off" for the glottal motions. In the case of speech segments with multi-phonemes, similar methods of measuring vector distances can be used. One procedure is to use the square root of the sum of the squares of all relevant vector coefficient differences. (Control coefficient distances are not used). When the distance is within a value defined by the user, an identification is defined and the related probability based upon the distance measure can be attached to the identification unit as desired. The use of a logical test operation is well known. Well defined normalization and quantization techniques for feature vectors make for well defined code book comparisons because the vectors can be instrument and speaker independent. An additional advantage is that individual-speaker rates of phoneme sequence articulation can be normalized and time aligned speech frames can be produced.

An EM/Acoustic Hidden Markov Model for Speech Recognition:

The methods of forming speech unit feature vectors by deconvolving the EM sensor measurement of the excitation function from the acoustic output can be used to form vectors of data from sequences of speech frames representing sequences of phonemes. They describe the coding of many sequential acoustical units, e.g., sequences of phonemes, diphones and other multi-phones. Such vectors are especially useful for the purposes of identifying symbols for natural spoken speech using an EM/Acoustic Hidden Markov Model (HMM) method. Many human speech segments consist of many phonemes run together, and are therefore many acoustic units long before word-breaks occur. Sequences of single speech frame feature vectors as well as one or more multiple speech frame feature vectors can be treated as patterns of numerical values that can be tested against combinations of the pre-stored patterns of the limited reference feature vector data set. HMM statistical techniques can associate these measured and formed sequences of feature vectors with test patterns constructed, as needed by the algorithm, from only a limited number of feature vectors in a code book. Typical code books contain pre-recorded and processed feature vectors for 50 PLUs and 1000 to 2000 diphones.

An EM Sensor/Acoustic HMM allows the user to statistically identify a phoneme or a pattern of phonemes by comparing the probability of observing such a series of feature vectors representing known words or phrases. This procedure requires a learning phase, as is well known in the art for the acoustic vector HMM approach, to build up the test patterns of combinations of feature vectors for the words in the vocabulary being used. The methods herein make the HMM method of speech recognition very valuable, because the data is so accurate and well defined. The methods herein provide very accurate procedures to rationally identify feature vectors by deconvolving, normalizing, quantizing, time aligning, and modeling the recorded information. The algorithm then forms a sequence (i.e., matrix) of as many feature vectors as needed for the specific EM/Acoustic HMM in use. As a consequence most of the ambiguity of individual speaker variations is removed and the patterns of speech units have little variability from speaker to speaker making HMM a very accurate identification technique.

An EM/Acoustic Neural Network Method of Speech Recognition:

Neural network algorithms are useful for associating a pattern described by a feature vector with a symbolic representation of one or more acoustic speech units. This method uses the training period method to cause the adjustable parameters within neural network algorithms to be associated with the EM/Acoustic input feature vectors. Because these are speaker independent and instrumentation independent), the vectors defined during speech by a user as well as by reference groups of speakers during codebook generation have little variance for the same acoustic speech unit. The associating of the real-time, input feature-vector known conducted using well known neural network algorithms (e.g., back propagation using two or more layers) to associate each input with a known acoustic speech unit, e.g., phonemes, words or other speech units. For the procedures herein, each feature vector may be 150 coefficients in length, which when taken three time frames at a time, require nearly 450 inputs to the neural network. (control and similar feature vector coefficients are not used as inputs). Once trained, off line using a computation process of needed power, the network algorithm can be loaded into the user's processor to provide a rapid association from an input feature vector to an unambiguous output speech unit. (see for example Papcun et al., J. Acoust. Soc. Am. 92, pt. 1, p. 688 (August 1992) for "micro beam" x-ray detection of speech organ motions for an approach well known to practitioners of neural network applications). Because of the unique association of a speech sound symbol with vocal articulator positions, as represented by the feature vector coefficients, an accurate identification of the symbol associated with each feature vector can be made.

A Method of EM/Acoustic Joint Probability Speech Recognition:

Recognition using the method of joint probability can produce increased speech recognition accuracy. It is based upon jointly using the deconvolving approaches together with conventional speech recognition (i.e., CASR) information, and using pure EM sensor based recognition information (i.e., NASR).

Step 1: The user chooses a conventional acoustic (CASR) system to examine an acoustic speech unit or speech unit series (e.g., phoneme series). The CASR system selects one or more identifications (e.g. phoneme symbols such as /ah/) which meet the criteria of identification. A first set of all such identified units, with probabilities of identification exceeding a user-chosen level (e.g., 80%), are formed.

Step 2: The deconvolving process, plus other information as described herein, is used to form a feature vector. One of the statistical techniques (e.g., HMM, phonetic template, or neural networks) is used to identify the symbols for one or more acoustic speech units associated with the feature vector formed during the speech frame being examined. If the identification is within the predefined probability band, it is associated with the identified sound unit symbol (and its actual probability of identification is also recorded) and it is added to a second set of identified acoustic sound units. Other potential unit identifications from this step, with differing but acceptable probabilities of recognition, are included in the second set as well.

Step 3: The user select data from an EM sensor system in use, and generates a NASR feature vector each speech time frame. The NASR system estimates symbols for one or more acoustic speech units that meet the probability criteria of NASR identification procedures. A third set of symbols of identified acoustic speech units is formed, with attached probabilities of recognition.

Step 4: Steps 1, 2, and 3 are each repeated to generate probabilities of identification for those symbols identified in the other steps that were not found the first time through. That is, an identified unit from step 1 with probability (for example) greater than 80%, could have been un-recognized in step 2, because its probability was below a cutoff value. For the joining of probabilities each symbol from each step must have a probability of identification from the other 2 steps. In the second cycle through, if a symbol is not easily assigned a probability in any one of the procedural steps, it can be assigned a probability of zero.

Step 5: An algorithm joins the separate probabilities from step 1 and/or step 2, and/or step 3, in a fashion weighted by their probabilities to obtain the most likely recognized sound unit. One algorithm is to find the joined probability by taking the square root of the sums of the squares of the probabilities for the symbol obtained from each step 1, 2, and 3.

The important and valuable addition provided by the deconvolved feature vector data, and other procedures herein, is that it is a mixing of acoustic with EM sensor data which provides an additional degree of data correlation that is sufficiently different in a statistical measurement sense that the joint probability of the data described above will be better than if only one or two separate sets of data were used. This approach works well with one EM sensor and microphone, but is especially valuable when the user chooses to employ two or more EM sensors with an acoustic microphone. This approach also works very well with multiple sets of very precise, but often incomplete data.

An example of a two EM sensor system uses an EM glottal motion sensor and an under-jaw, upward-looking EM sensor. With these the sensors, the user obtains three data sets from: 1) a single EM sensor feature vector describing the conditions for the raw, tongue, and velum signals each time frame, 2) glottal motion data from an EM sensor measuring the excitation function and 3) acoustic microphone data. Probabilities of symbol identification, using the data three sets can be joined together naturally by a single software processing system using standard statistical algorithms. Each individual sensor, plus the deconvolving of 2) from 3), offers very unique and precise features that lead to a high probability for certain sets of symbols and a very low probability value for all other symbols. Using all three sets together, the algorithm form a very high probability of identification of a unique symbol. The user has the option with such a combined system to use each sensor and algorithm in its most economical and accurate way for the recognition application. This approach leads to economical computing, and rapid convergence to the identified sound unit.

A Method of EM/Acoustic Exclusive Probability Speech Recognition:

The method of exclusive probability uses methods of formation of three sets of feature vectors described above in steps 1 to 3 in the section on joint probability speech recognition. It uses a sequential procedure to statistically reject identifications made by any one of the three types of recognition systems. It uses logical tests to exclude (i.e., reject) symbols not meeting certain criteria.

Step 1: Use the CASR approach to identify the acoustic sound units for the speech time frame or frames under consideration, as long as the probability of symbol identification exceeds a user defined value, e.g. 80%. At this stage, the probability criteria is set to retain symbol identifications that may have similar probabilities of identification by the CASR data at hand. Subsequent steps are be used to eliminate ambiguous identifications from this step.

Step 2: Use the deconvolved feature vector set to reject those identified sound units from 1) that meet the probability criteria of definition (by CASR) but fall below the user-set levels of acceptable probabilities for identifications of symbols based upon the probability of identification using the feature vectors formed by the EM/Acoustic methods herein.

Step 3: Use one or more of the NASR EM sensor identification methods to check the probability of each remaining identified acoustic unit symbol from step 2. Identify those acoustic speech units that do not meet the probability criteria of the NASR system, and reject them. Leave the remaining, highly probable acoustic units and their probabilities of identification in the data set.

Step 4: Use a standard statistical algorithm to join the probabilities of those identified acoustic units that remain in the set, after Step 3. This leads to a small number of acoustic speech units, usually one, that meets the "exclusion" criteria of the sequence of three steps.

This process rapidly eliminates those ambiguous identifications, caused by insufficient data at each step. Symbols that have low probabilities of identification are rejected early in the process and thereby reduce computational processing later in the process. This process causes the one or few remaining acoustic speech unit symbols, which pass the three sequential sensor/algorithm tests, to have a very high probability of correct identification. This method can be applied to the data by permuting the order of techniques for identifying the feature vector. For example, the deconvolving technique might be used in Step 1, while the CASR technique could be used in step 2. The method of exclusion can also work with two rather than three identification steps. This method is very valuable for using partial information from auxiliary sensors or as "by-products" of the major sensors. It provides a more accurate identification of the acoustic sound unit than either an all acoustic system, or an all EM/acoustic feature vector system could accomplish without the additional information. For example, the presence of one or more fast tongue tip motions measured with a tongue EM sensor indicates that the acoustic unit identified by the deconvolving process must be a phoneme consistent with such tongue motion, e.g. in English /th/ as in "the", or a rolled /r/ as in "rosa" in Spanish or Italian. If the feature vector coefficient from step 3, for example, does not describe rapid tongue tip motion, the symbol identification is rejected.

If two speech units symbols remain, that have sufficiently high probabilities, both placed in a set with their associated probabilities. The user can choose to use only the highest probability unit or the system can automatically ask the speaker to repeat the sound or phrase if both probabilities are similar or below desired certainties. If no recognized symbol meets the probability criteria, then a signal can be sent to the control unit that the acoustic speech unit is ambiguous, and the identified acoustic units are shown in order of certainty with probabilities attached. The algorithm can be programmed to automatically ask the speaker to repeat for clarification under such circumstances.

Speech Synthesis:

The methods provide for the synthesis of high quality, idiosyncratic speech from stored EM sensor/acoustic data obtained from an individual speaker or from an averaged set of speakers. Individual speaker means any individual, ranging from a normal office dictation worker to a famous actor. The speech encoding process to be used for subsequent synthesis depends upon how the original feature vectors were coded and stored in a code book. The methods herein can be used to form a set of feature vectors optimized for speech synthesis. They may be based upon an average speaker or a particularly desirable speaker whose acoustic speech is quantified and stored in a codebook.

Step 1: Form a reference codebook by recording the acoustic speech units of a desirable speaker or group of speakers for each acoustic speech unit needed for the synthesis application of the user. Form feature vectors of all of the acoustic units that will be used based upon the procedures herein, and use the master timing techniques herein to define the beginning and end of these vectors.

Step 2: Use a commercial text-to-speech translator that identifies all of the required speech units (phonemes, diphones, triphones, punctuation rules, indicated intonation, etc.) from written text for the purpose of their retrieval.

Step 3: Use an automatic search and retrieval routine to associate the sound units from Step 2 with a code book location described in step 1.

Step 4: Select the feature vector to be used from the code book location described in step 3. The feature vector information, in addition to excitation function and transfer function, includes the timing of the sound units, the joining relations from frame to frame, and the prosody information.

Step 5: If phoneme to phoneme transitions are not called out by step 2, generate the transition acoustic sound units using one or more of the following: Two sequential voiced sound units are joined at the glottal closed times (i.e., the glottal zeros) of voiced speech frames, while unvoiced frames (or unvoiced-voiced frames) are joined at acoustic amplitude zeros. If transition rules are present that describe the rate of interpolation between voiced phoneme units, they are used to set the transition time frame durations and to interpolate excitation and transfer function coefficients that are modified by their relationship to another articulator condition in the preceding or following time frame. Another method of interpolation is to use diphoneme or triphoneme acoustic speech patterns, pre-stored in a code book, which are normalized to the proper intensity and speech period and which are placed, automatically between any two phonemes called for from step 2.

Step 6: Provide the prosody for the acoustic sounds generated during each speech time frame or combination of speech time frames. For example, use prosody rules to set the rate of sound level amplitude increase, period of constancy, or rate of amplitude decrease over several speech frames. Use prosody rules to set the pitch change from the beginning of the speech sequence to the end, as defined by phrasing and punctuation rules. Such prosody information is obtained from the text-to-speech converter, in step 2, and is used to alter the frame vectors as they are taken from the code book to meet the demands of the text being synthesized into speech.

Step 7: Convolve the excitation function and the transfer function, together with the intensity levels, and generate a digital output speech representation for the time frames of interest. This procedure can produce acoustic signals that extend into the next speech time frame. The signal from one frame can be joined to the acoustic signal (i.e., amplitude versus time) generated in the next frame by procedures of adding wave amplitudes and then squaring (coherent addition) or by squaring amplitudes and adding to obtain intensities (incoherent procedure). Combinations of these approaches, with "dithering" or varying feature vector coefficients from frame to frame, may be employed to simulate the short term variations in human speech. This digital representation is converted to analog, via a D/A converter, and broadcast as desired.

Figure 19:
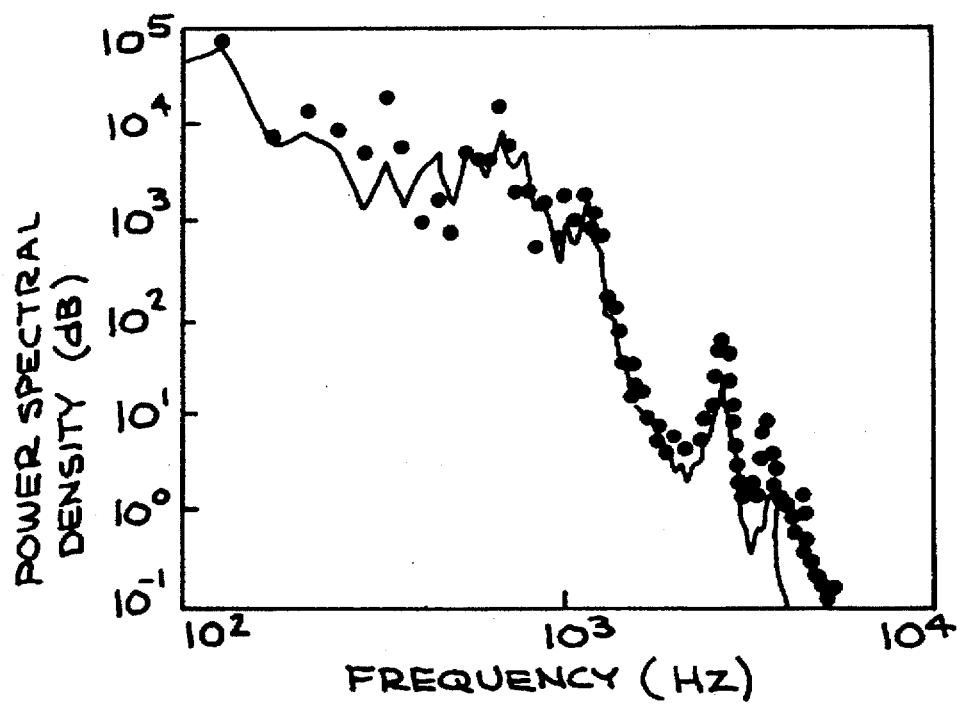
FIG. 19 shows the comparison between the measured and synthesized power spectra of the acoustic speech phoneme /ah/.

FIG. 19 shows data for the reconstructed acoustic speech unit /ah/, which experimentally produced a pleasing sound. The originally recorded acoustic data is shown by the points on the curve and the line is the reconstructed sound spectrum, formed according the steps 2 through 7 above. The sound/ah/was manually chosen.

Methods to Alter Synthesized Speech:

The methods of coding and storing speech feature vectors can be used to alter the original coding to meet the speech synthesis objectives of the user. The methods described herein provide the user with well defined and automated procedures to effect the desired speech changes. For example, the original speech pitch can be changed to a desired value and the rate of delivery of acoustic speech units can be changed to a desired rate. In each speech feature vector, several coefficients describe the excitation function. By changing the duration of the excitation function, either in real time (for example by compressing or expanding the individual glottal triangular functional shape to take less time) or in transform space (by moving the transformed excitation amplitude values to higher or lower frequency bins), one can change the pitch to be higher or lower. These procedures increase the number of glottal open and close cycles per unit time, and then by convolving this higher (or lower) pitch excitation function with the unchanged vocal tract transfer functions for each newly defined speech time frame interval, one obtains a new higher (or lower) pitch voiced output. To implement prosody rules, that describe pitch change, the algorithm can cause a rate-of-change of pitch to occur during a segment of speech, containing several pitch periods. The algorithm slowly changes the excitation function pitch for each frame, from an initial pitch value to a slightly higher (or lower) one in the following frame. Also, the algorithm can "dither" the glottal period duration for each constructed time frame to provide a more natural sounding synthesized speech.

These new methods provide a very important procedure for joining sequential excitation functions during their periods of glottal closure. In this manner, no abrupt changes (i.e., no signal derivative discontinuities) takes place in the real time acoustic output signal. In a similar fashion, the user can simply add (or subtract) extra time frames or extend a multiframe transfer function (i.e., with constant excitation function and transfer function, just more periods) to adjust the length of each speech unit. Using these methods, one can extend the time it takes to say something or speed up the speaking to finish words sooner, but maintain excellent quality speech using the basic, speech-frame "building blocks" provided by the methods herein.

An important application of these methods is to synchronize the rate of an actor's speech recorded in a sound studio, with his or her facial motions (e.g., lips) on video (and/or film) media. The obtaining of facial vocal motion requires the use of an EM sensor to record lip motions and a video image analyzer to track key facial motions (e.g., lips) on video or film media associated with known speech frame features obtained using the EM sensor information. Image analysis systems are commercially available that can follow patterns within a video or film image. The methods herein allow the user to synchronize the speech track by synthesizing new speech, at correct rates, to follow the facial motions in the sequence of images. The algorithms herein can alter the excitation function length by stretching or compressing the time frame, by adding or deleting additional frames, by shifting frames in time by adding or deleting silence phonemes, by introducing pauses, by keeping certain frame patterns constant and by stretching others, and in such a manner that the apparent speech is unchanged except that it matches the facial motions and/or other gestures of the speakers.

The user may also alter the transfer function of the speaker as desired. The user can modify the physiological parameters and construct a new transfer function using physiological or equivalent circuit models. Examples are lengthening the vocal tract, changing the glottis to mouth diameter ratio, or increasing the size of the nasal cavity. The methods also allow almost arbitrary changes in transfer functional construction for amusement, for simulating animal sounds, for research, or for special "attention-grabbing" communication applications by "playing" with the coefficients and synthesizing the resulting speech. Once a modified transfer function is formed, as a consequence of altering the physiological models or by using empirically determined coefficients, the user then makes the corresponding changes in the code book. All feature vector coefficients in the code book that correspond to the altered transfer function are changed to make a new code book. The methods herein enable such automatic modifications because the several functionals described above for defining vocal tract transfer functions, e.g., the ARMA, equivalent circuit parameters, or physiological based functionals, are well determined and easily modified. For synthesizing the modified speech, the user proceeds according the speech synthesis steps described above. Each selected acoustic speech-unit, is associated with a feature vector that includes the modified transfer function information, the excitation, prosody, timing changes, and control information (including synchronization data).

Another method of altering the data stored in a code book that was derived from one person or from an average person is to substitute the excitation function coefficient descriptors in a given feature vector by those from a more desirable speaker. Similarly, one can exchange the transfer function, or the prosody pattern from an original speaker with those from a more desirable speaker. The user then performs, upon demand, the convolving of the excitation function with the transfer function to produce a new unit of sound output for the purposes of the user. For consistency, such changes must be performed on all relevant feature vector coefficients that are stored in the code book being used. For example, all excitation function coefficient descriptors in all feature vector coefficients must be changed according to the prescription if one person's glottal characteristics are substituted for another's. This is easy to do because all feature vector formats are known and their locations in memory are known; thus, algorithmic procedures allow the user to alter a known set of codebook vectors and their specific coefficients.

These methods for altering and reconstituting speech make it possible to generate synthetic excitation functions and transfer functions that are very unusual. Methods of change include generating animal speech by using animal vocal system models, constructing physically impossible open-close glottal time functions or transfer functions, shifting pitch periods to create very high pitched voicing (e.g., dolphin speech at 100 kHz), or changing the excitation functions in response to external stimulus such as to follow musical sounds or notes. That is, a poor singer could sing into systems similar to those herein, and a musically corrected voice would be synthesized and broadcast. Or an animal trainer could speak into a processor and have his speech sounds transformed to those frequency bands and patterns optimized for the animal being trained. These techniques can easily create physically unrealizable feature vectors, based upon exaggerated physiological parameters. The technique can also create feature vector alterations to obtain amusing sounds (e.g. chipmunk voices) or desirable prosody patterns. These special effects can be used for purposes of entertainment or research, or other specially desired effects can be easily created using the techniques. Since the coding methods are both fundamental and convenient to use, these methods are very useful and valuable.

Speech Telephony

Analysis-Synthesis Telephony—Vocoding:

The methods of speech recognition and speech synthesis described herein provide a valuable and new method of speech coding and decoding for the purposes of real-time Analysis-Synthesis Telephony (i.e., Vocoding). It is particularly convenient to use the feature vector generating process because the speech segment feature vectors are in a form immediately usable for synthetic speech and for telephony transmission. One method of analysis-synthesis telephony (i.e., vocoding) starts with a speaker speaking into a microphone while an EM sensor measures glottal tissue motions. FIG. 20 shows a view of a head with a cutaway of a vocoding telephony handset 90. Handset 90 holds three EM sensors 91, 92, 93 and an acoustic microphone 94. EM sensors 91, 92, 93 are preferably micropower radars optimized for specific organ condition sensing, and direct EM waves toward and receive reflected EM waves from various speech organs. For example, sensor 93 is positioned for vocal fold and glottal motion measurements. Handset 90 also includes a transmitting and receiving unit 95, which is connected externally through wired or wireless connection 96. Transmitting and receiving unit 95 is connected to a control unit and master clock 97, which controls a speech coding processor, recognizer code book and memory unit 98 to which EM sensors 91, 92, 93 and microphone 94 are connected. Control unit 97 is also connected to a decoder processor, speech synthesizer, memory and code book unit 99, which is connected to a receiver loud speaker 100. Unit 99 and speaker 100 are mounted in an ear piece 101 of handset 90 so that the speaker 100 is positioned over the person's ear. Several system functions illustrated in FIG. 20 are similar to those shown in FIG. 8.

The speech is analyzed by deconvolving the excitation function from the acoustic output, and feature vectors are formed describing each time frame of the speech output. The numerical coefficients of these feature vectors can be transmitted directly using standard telephony coding and transmission techniques. Alternatively, the speech sound unit can be speech recognized, and the symbols for the recognized unit (e.g. in ASCII or other well known code) can be transmitted. Additional control or speaker characterization information can be transmitted as desired. The methods for the formation of "difference feature vectors" and for the identification of "More Important" and "Less Important"

transfer function coefficients are especially useful for telephony because their use reduces the bandwidth needed for sending coded voice information.

At the receiving end of the telephony link, the transmitted signal is reconstituted into speech. The synthesis procedure may use the transmitted feature vectors, it may synthesize new speech from transmitted speech symbols, and using its internal code books of stored feature vectors in a "text-to-speech" process. The user may choose a combined approach using partial speaker information to "personalize" the synthesized speech to the degree desired. Alternatively, the receiver's controller may recognize incoming coded speech, and direct the recognized symbolic information to a local computer system for processing or storage purposes, to a fax system or printer to print the received symbols, or to an analog recording system for later use by the intended receiver.

The method of vocoding herein includes the process of attaching additional information to the transmitted speech information-packet for each speech frame. This additional information can be used by the receiver to perform speaker identification, to do speech alteration, to translate to a foreign language, to encrypt the data, or to minimize the bandwidth. The transmission of the feature vectors thus formed can occur in real time over transmission systems such as wire, optical fiber, acoustic (e.g., underwater communication) or over wireless systems. The method then includes synthesizing the feature vectors into acoustic speech representing the speaker, for the purposes of broadcasting the rendered acoustic sounds through the telephony receiver to the listener. The speech synthesis part of the vocoding system can be designed to use average speaker qualities, or it can be designed to transmit very high fidelity speaker-idiosyncratic speech. High fidelity transmission will use relatively higher bandwidth for the transmission of the more accurate description of the feature vector information, than the minimum possible, but it will require much less bandwidth than present high fidelity voice transmission. Conversely, minimum bandwidth systems remove all information about the speaker except for that needed to communicate minimal voice information.

When the speaker in a vocoding communication system becomes the listener, and the listener the speaker, the vocoding system works in the same fashion as described above except for the interchange of speaker to listener, and listener to speaker. In addition the process can operate in real time, which mean that the recognizing, coding, recognition (if needed), and synthesizing can take place while users are speaking or listening. Real time means that the time delay associated with coding, transmitting, and resynthesizing is short enough for the user to be satisfied with the processing delay. The computationally efficient methods of coding, storing, altering, and timing, which have been described herein, make possible the needed rapid coding and synthesis. Elements of such a system have been demonstrated experimentally by coding several spoken basic speech sounds and acoustically synthesizing them using the coded information.

Minimal Bandwidth Transmission Coding:

Minimum transmission coding is made possible using the identification and coding procedures described herein. One method is to use the speech compression methods described above. Another is made possible when the speech recognition part of the system results in a word identification and/or the sending of minimal speaker idiosyncratic information. By using speech identification in a system, such as the one shown in FIG. 20, each acoustic speech unit is translated to a word character computer code (e.g. in ASCII) is then transmitted along with little or no speaker voice characterization information, for the purpose of minimizing the bandwidth of transmission. The symbol transmission technique is known to use 100 fold less transmission bandwidth than real time speech telephony. Thus the value of this transmission bandwidth compression technique is very high. The speech compression techniques described above using the coding procedures herein, is less effective at bandwidth minimization, but it is simpler to use, retains most of the speaker's speech qualities, and is calculated to use 10 fold less bandwidth than real time speech.

Reductions in bandwidth (i.e., bandwidth minimization) can be attained using many of the well known coding techniques in present communications, most of which are based upon the principle of only transmitting changes in information that are discernible to the user and they do not retransmit information every "frame". The "difference feature vector" method described above is very useful for this application. In addition, bandwidth minimization is further enhanced by using the minimum quality of speech characterization needed for the application. The methods for the characterization and reconstruction of speech are especially suitable for these procedures of bandwidth minimization, because these methods herein show how to measure and characterize the simplest units of speech possible. For example, partial information on the speaker's physiology can be sent to the receivers process and incorporated into the synthesis model for more personalized speech reconstruction. Once obtained, these speech "building" blocks of excitation and transfer function can be approximated and used in many ways. In particular, well defined decisions on the "change information" needed to update the next frame of speech, consistent with the user's needs, can be made before the information is sent off through the transmission medium. Because the coding and resynthesis techniques are so intimately and naturally linked, the initial coding for transmission and subsequent decoding and resynthesis is straightforward and economical. These methods are valuable because they provide important means to save valuable and expensive transmission bandwidth that reduce costs. Another valuable use of the method is to allow additional information, such as encryption "overhead" or speaker identification, to be transmitted along with the sound information on present fixed bandwidth systems.

Simultaneous Spoken Language Translation:

The methods herein for real time speech coding, recognition, and resynthesis in a vocoding system are valuable for real time speech translation from one language to another.

Step 1: The user speaks into a system such as shown in FIGS. 8 and 20. The system codes each acoustic speech unit.

Step 2: The system recognizes the coded speech units and forms symbolic text of the letters, words, or other language units such as pictograms.

Step 3: The system uses a commercial language A to language B translation system, which takes the symbolic text of the recognized acoustic language units from Step 2 and translates them into symbol text for the language B.

Step 4: The system uses a commercial (or other) text to speech converter to convert the symbols in language B into feature vectors, together with prosody rules.

Step 5: The system synthesizes the translated symbols into acoustic speech in language B.

A variant on this method is, in step 2 above, to associate with each recognized word in the codebook, the associated foreign word. Thus the translation step 3 and the text-to-speech in step 4 is avoided for simple translations applications. This language translation system can work in real time and be very compact. It can be packaged into a portable megaphone (e.g., FIG. 20 but with a translation unit and a megaphone attached) where the user speaks one language and another language comes out. For more complex and more accurate translation applications, it can be built into a stationary system as shown in FIG. 8.

Presentation and Teaching:

This method of feature vector formation makes it possible to display the information received for each speech unit for feedback to the user. The display information can be graphical on a screen (e.g., images of the speaker's vocal tract), or the information can be sounded, printed, or transmitted to a user via tactile or electrical stimulation. The use of feature vectors based upon physiological parameters aid in the visual display of the sizes and positions of the vocal tract articulators of the speaker. These can be used for purposes of speech correction, real time speech assistance, and speech education because the information can be used to illustrate the problems with the positioning of the speaker's vocal organs for the attempted sounds. Conversely, the methods herein enable the illustration of the corrected vocal organ positioning for the desired sound, using reference codebooks of correct feature vectors. These procedures are very valuable for speech correction and for foreign language teaching. The capacity to recognize the user's speech and to communicate the characteristics of the speech back to a disabled user, in real time, is of great value to speech impaired persons. For example, a deaf speaker can receive feedback stimulus, via tactile or electrical signals to his skin or to his inner organs, on the quality of their articulation.

Conclusion

The invention includes a method of measuring and generating in an automatic manner an accurate speech excitation function of any speaker for one or several sequential speech time frame intervals. Simultaneously, the acoustic signal is measured and the excitation function is deconvolved from it, leading to a speech tract transfer function for one or several sequential speech time frame intervals. The invention includes methods of accurately timing, coding these data into feature vectors, and storing the information into code books.

There are two types of excitation functions—voiced and unvoiced—and a few sounds use both together. To generate the voiced excitation function, the volume air flow through the glottis, or the post-glottal pressure, is measured by measuring glottal tissue locations using EM waves. Air flow through the area of the glottal opening can be measured during voiced speech by using EM sensors to measure the change in reflection level of the glottal region as the vocal folds open and close, and then using calibrations and models to obtain the air flow. Similarly, pressure can be measured. EM sensors measure reflection changes from the front or sides of the speaker's voice box (Adam's apple). An analytic calculation of the area opening is derived from a model functional dependence of EM reflectivity from the opening. A second technique to obtain the area is to correlate the reflected EM signal with measured optical images of the area of the opening of a representative set of speakers' glottises. A third technique is to use one or more range gated EM sensors to accurately follow the reflection from one or both edges of the glottal opening, in the sensors' line of sight, and to calibrate such signals with optical images. A fourth method is to construct a table of EM signals versus calibrated, in situ, air flow or pressure sensor signals on representative speakers during a training period.

Known equations or calibrations defining the volume air flow through the glottal opening (between the vocal folds), under conditions of constant transglottal pressure, can be used to define volume air flow vs. time in an absolute or relative fashion. This volume air flow function provides a new and valuable description of the human vocal tract voiced excitation function for each time frame of voiced speech. Similarly, post glottal air pressure can be calibrated and obtained, as needed, for correction of transglottal pressure estimates and other applications.

The change in the air flow as a function of time for the voiced excitation function can be estimated in cases when the transglottal pressure is not constant during the time frame of estimation. This process makes use of calculated back pressure from the estimated transfer function, which is then used to make a first order air flow correction. The estimation uses models of the allowed glottal motion to determine valid glottal motions due to changes in back pressure as a function of frequency. or it uses direct measurement of tissue motions due to the pressure variations.

Acoustically generated noise can be removed from the glottal signal by using microphone information to subtract the noise signal, or by using Fourier transform techniques to filter out acoustic signals from the glottal motion signals.

The functional shape of the volume air flow excitation function in real time, and in transform space (Fourier or Z transform), can be approximated, including the glottal zero (or closed) time. An excitation feature vector is constructed by defining an approximation functional (or table) to the measured excitation function and by obtaining a series of numerical coefficients that describe the functional fitting to the numerical data for the defined time frame(s).

The number of speech frame time intervals during which both the excitation function and the acoustic output remain constant is determined. Constant is defined as the signal remaining within a band of acceptable change in real time or transform space. A feature vector can be defined describing both the excitation function and the defined number of time frames during which the two functions remain constant.

A slowly changing functional form (such as pitch period) of the volume air flow excitation function, and corresponding acoustic output, over several speech time frame intervals can also be determined, and a feature vector defined describing the excitation function and the functional changes for the defined time frames. Other slow changes such as amplitude can be similarly described.

The measured excitation function, including noise and back pressure terms, can be compared to an average speaker and a feature vector defined based upon deviations (i.e., differences) from the voiced excitation function of an average speaker or of a specific speaker. This can be done in real time or Fourier space. Similarly, difference feature vectors can be formed by comparing a recently obtained featured vector to one obtained from an earlier time frame.

The invention also includes using the voiced excitation function periods as master timing units for the definition of time frames during speech processing. This includes defining the beginning and end of a glottal open-close cycle, obtaining the times of glottal closure (i.e., no air flow) within the cycle, and joining one such cycle to the next for concatenation of all information obtained in one speech time frame to that obtained in the previous or next time frame.

Single or multiple time frame timing unit measurements can be made of simultaneous speech organ conditions and other conditions such as video, electrical skin potential, air flow, magnetic resonance images, or ultrasonic wave propagation.

The invention includes characterizing and storing as part of a feature vector the automatically generated time frame information; associating each speech time frame with a continuous timing clock, and storing this absolute timing information as part of a feature vector; and using such defined time frames for the purposes of speech reconstruction, speech synchronization with visual images, visualization of vocal organ conditions for training or speech prosthesis, speaker identification, foreign language translation, and coded telephony.

The invention includes methods to estimate the unvoiced excitation functions of the speaker during defined speech time frames, by determining that speech is occurring without vocal fold motion. A "modified white noise" excitation function is then selected from a functional form that has been validated by listeners and by analysis to provide an accurate excitation function to excite the known transfer functions of average speakers (in the language of the speaker) to simulate the measured acoustic output for known sounds. A second method is to deconvolute the known transfer function for the unvoiced sound from the acoustic output and obtain a measured unvoiced excitation function source.

Speech unit time frames are defined when unvoiced speech is being sounded by the speaker during the speech time frames of interest. The algorithm is to simply measure the time duration over which the acoustic spectrum is constant and record that time to be the frame duration; or, using spectral constancy, and times defined by extrapolated or interpolated voiced-speech time frame duration from the preceding or following voiced speech periods; or by using pre-defined time frame periods, e.g. 50 ms.

A preferred unvoiced-excitation-function feature-vector is defined by the Fourier transform for one or more speech time frame intervals during which the excitation function is constant or slowly varying. The number of unvoiced speech frames during which a constant or slowly changing unvoiced excitation of the vocal tract is occurring is determined, and a feature vector is defined that describes the excitation function, the time frame duration, and the slow changes in the excitation function over the defined time frames.

The invention includes a method of measuring and recording the acoustic output of the human speaker, simultaneously with the EM sensor signals, during one or more speech time frames and storing the information with sufficient linearity, dynamic range, and sampling bandwidth for the user's application.

The microphone voltage amplitude vs. time signal recorded during the speech time interval frame or frames is characterized in real time or in Fourier frequency space for the purpose of deconvoluting the excitation function from the recorded acoustic output function. Information is selected from the recorded microphone voltage vs. time signal that is statistically valid and characterizes the sound pressure amplitude vs. time or the sound pressure Fourier amplitude and phase vs. frequency during the desired time frame (s) for the purposes of subsequent processing. The lip-to-microphone acoustic radiation transfer function can be deconvoluted, in Fourier space or in real time space, to remove instrument artifacts, to simplify the transfer function, and to enable more rapid convergence of deconvolution procedures in subsequent processing steps.

The invention includes a method of using EM speech organ position or velocity information (e.g., vocal folds) for one or several sequential speech time frames to deconvolve the vocal system source function from the measured acoustic speech output from a human speaker. This makes possible an accurate numerical representation of the transfer function of the human vocal tract in use during the time frame(s) over which deconvolution is performed. Deconvolving can be done by real time, by time series techniques, by fast Fourier transform techniques, by model based transform techniques, and other techniques well known to experts in the field of data processing and deconvolution.

A human speaker's vocal tract transfer function used during one or more speech time interval frames is obtained by using well known deconvolution techniques (such as that associated with the ARMA approach) by dividing the transformed microphone acoustic pressure signal by the transformed excitation source signal. The lip to microphone transfer function, or other known functionals, can be obtained as needed by deconvolving, fitting to known functionals, or other well known numerical techniques.

Additional information on the positions of individual organ locations, and thus the shape of the vocal tract, can be obtained through the use of other EM sensor data, with or without simultaneous acoustic data, to determine the optimal transfer function functional structure for best convergence or most accurate fitting. An example is to choose the appropriate number of poles and zeros in the ARMA functional description for each speech time interval frame.

A speech transfer-function feature-vector can be defined from the amplitude and phase vs. frequency intervals from the deconvolving of the excitation function from the acoustic output function, using Fourier transform or other techniques. The function can be defined by a table of numerical values or be fit by a known functional form and associated numerical parameter coefficients.

The invention includes a method of approximating the transfer function by using the well known pole-zero (or time series a, b coefficient) approximation techniques such as used by the auto regressive-moving average (ARMA) technique. Transfer function feature vectors are formed for the speech time interval frame or frames, including obtaining amplitude, phase, type of functional form, defining functional coefficients, time duration of feature vector, and other necessary information.

A feature vector describing the transfer function is formed by using the pole and zero representation or the a, b representation of the ARMA description for the speech time interval frame or frames of interest. A feature vector describing the transfer function is also formed by using defined ARMA functional forms which are based upon fixing the numbers of poles and zeros to be used (or alternatively the a, b values) of the ARMA description for the speech time interval frame or frames of interest.

The invention includes defining a difference "Pole-Zero" (or a, b) feature vector by storing differences in each vector element from a previously defined known type of speaker or by storing differences from past time frames during a constant period of use. It also includes the definition of "more important" pole-zero (or a,b) values which define major tract dimensions, and "less important" values which define the idiosyncratic sounds of an individual human speaker.

The invention includes approximating the transfer function by using well known electrical and/or mechanical analogies of the acoustic system which are predefined by foreknowledge of the human vocal tract acoustic system, including transfer function "feature-vector" formation for the speech time interval frame(s). Feature vectors describing the transfer function are formed by using the impedances, (i.e., the Z's), or circuit values (e.g. L's, C's, R's, G's) in the electrical analog models. A feature vector can be defined by storing differences in each vector element from a previously defined known type of speaker, or from coefficients obtained in a previous time frame.

The feature vector and excitation function information can be used to define the physiological parameters of the human speaker. The transfer function parameters are used to define the electrical analog models and are associated with physiological parameters such as tract length, mouth cavity length, sinus volume, mouth volume, pharynx dimensions, air passage wall compliance, and other parameters well known to acoustic speech experts. The excitation function information can be used to define the masses, spring constants, and damping of the glottal membranes.

A feature vector describing the transfer function can be formed by using the physiological dimensions of the speaker that are defined by the measured and derived transfer functions for the vocal tract configurations and used by the speaker during the speech time interval frame or frames of interest. A feature vector is also formed by storing differences in each feature vector element from a previously defined known type of speaker as a feature vector, or from coefficients taken in a previous time frame.

The invention includes a method of defining for each time frame and for multiple time frames, a sound feature vector that is a "vector of vectors". It is comprised of the user defined needed information from the excitation function feature vectors, vocal tract transfer function feature vectors, prosody feature vectors, acoustic feature vectors, timing information, and control information for all acoustic sound units, over as many time frames as needed, for the application in the language of use. It includes obtaining and storing such vectors in a data base (i.e. library or code book) during training sessions. The data bases are designed for rapid search and retrieval during real time usage. This method includes defining each unique speaker, defining reference speakers using individuals or averaged speaker groups, or translating coefficients to a hypothetical speaker using normalization, or artificial modifications of the functionals and their coefficients. It also includes forming such a vector over one or more defined speech frames, which includes the formation of the above for all syllables, phonemes, PLUs, diphones, triphones, multiphones, words, phrases, and other structures as needed in the language of use and for the application.

The stored feature vector information, contained in the type of functional and the defining feature vector coefficients on a given speaker can be used to normalize the output of the subject speaker to that of an average speaker. This normalization method recognizes the differences of an individual by comparing his individual excitation function and transfer function coefficients for known sounds, to those of a reference speaker's excitation function and transfer function coefficients, for the same sound during training sessions. The simplest method is the method of replacement of reference speaker feature vectors with those of the user and a second method is to replace feature vectors describing difficult sound combination. These personalize the code books and make comparison more accurate, and retrieval of vectors very individualized. A third method is a method of extremes, in which a mapping is made from the external values of each coefficient in the feature vector of the user to those a reference speaker. The values include the coefficient range-extremes for all necessary sound units for the application, and are obtained during training. Then feature vector coefficients obtained each time frame are normalized to those of the reference speaker by using a linear fractional mapping. This approach removes much of each individual's articulation variability, and allows the formation of a speaker independent feature vector for each time frame. In this manner, a speech sound can be associated with a sound symbol in a stored library with very low ambiguity and very high probability of identification. This approach also removes instrument variations.

The method includes quantizing the normalized feature vector coefficients into a limited set of values that reflect bands-of-distinguishability for the application. It is known that articulators must change their position or condition a certain amount for a noticeable speech difference to be considered important by the user. The bands of coefficient values that are perceived to be constant, are measured during system set-up and during training. As each normalized coefficient is obtained, it is mapped into one of a few values that reflect the "quantized" aspects of the speech articulator. This approach makes possible very rapid table look up, using the coefficients themselves to directly access codebook addresses for the corresponding stored reference feature vector.

The complete feature vector for several time frames, over which slow change or no change at all in the vector coefficients, can be collapsed to a feature vector describing one speech frame. In addition, the collapsed feature vector contains a few additional coefficients describing the total recorded duration of the sequence of constant time frames, plus some that define a model of the slow changes in one or a few coefficients over the entire sequence. This procedure is a method of speech compression that removes redundant information, and yet retains as many of the speaker's qualities as desired for the application.

The complete feature vectors, for one or more time frames, can be compared to stored information on a known human for the purpose of speaker identification, and providing statistics of identification. Such comparisons can be performed automatically over several time frame units, isolated time frame units, or on sequences of units where stored information on the desired speaker's identity is available from a preformed library. The speaker can speak prearranged words or can respond to information presented by the system, or the system can recognize sequences of units, using speech recognition, and compare them to stored information on the desired speaker's identity obtained from a pre-formed library.

The invention provides a method to code an individual's speech, not knowing the language being spoken, and to search through a series of code books for one or more languages to identify the language being spoken. The process makes use of the statistics of each language's sounds, sound patterns, and special unique sounds to obtain the language recognition.

The invention includes a method of speech recognition based upon using the feature vectors for the purposes of identifying all sound units in a given language. The simplest recognition technique, directly applicable with the methods herein because of their accuracy, is often called a phonetic template approach. A feature vector describes the condition of a speech unit with sufficient information, including redundancy and model constraints, that the phoneme (or other simple speech sound unit) of speech can be defined for the time period and be directly matched to a pre-formed vector stored in a codebook.

The sound unit under consideration, once identified with very high probability, is associated with a symbol. Symbols can be letters, ASCII computer code, pictogram symbols, telephony code, or other coding known to practitioners of speech recognition, synthesis, telephony and similar activities.

The invention includes a second method of speech recognition that uses Hidden Markov Model (HMM) techniques on a multi-time-frame feature-vector to statistically identify the sequence of phonemes being spoken in the examined time frames. The feature vectors are so accurate that this approach becomes fast, accurate, and accommodates large natural language, continuous speech vocabularies. This includes a learning phase as is well known for the HMM approach to conventional speech recognition. HMM techniques can be used to identify the diphones, triphones, multiphones, words, and word sequences in the examined time frame.

The invention includes a method of using joint probability on the feature vectors to statistically identify the phoneme being spoken in the examined time frame using multiple sensor input. Joint probability includes the use of a conventional speech recognition technique for the first step. It estimates the identify of one or more sound units and it records its probabilities of identification for the next step. The second step is to use the EM/acoustic defined feature vectors, obtained by deconvolving, to estimate separately the identity of the sound unit, and to assign a second set of probability estimates for the nonacoustic case. A third step uses EM sensor information alone and a third set of identified speech units and their probabilities are formed. The final step is to join the probabilities of each estimate to obtain a more accurate identification of the word unit than either an all acoustic system, an EM/acoustic, or an all EM feature vector system could accomplish by themselves. The joint probability technique can identify the diphones, triphones, multiphones, words, and word sequences in the examined time frame.

The invention also includes a method of using exclusive probability on the feature vectors to statistically differentiate between acoustically similar phonemes being spoken in the examined time frame using several different sensor information sets. Exclusive probability means starting, for example, with a conventional speech recognition technique to estimate the identity of one or more sound units. They may have similar probabilities of being defined using conventional acoustic techniques alone (i.e. there remains ambiguity in a statistical sense). The second step is to use, for example, the EM/acoustic defined feature vectors of each of the one or more acoustically identified phonemes to estimate separately the identity of the sound units, and to assign an estimate of the probability based on EM/acoustic generated vectors for each ambiguous sound unit. Any sound unit from the first step that does not meet a minimum probability from the second step, is removed from further consideration (i.e., it is excluded). This reduces computational time, because those units that are rejected early, are no longer considered. A third step can use EM sensor information alone, to test the remaining sound units from steps 1 and 2, and if they do not meet the criteria, they are rejected. A final step is to join the probabilities of each estimate to obtain the most accurate identification of the remaining word unit or units, than either an all acoustic system, or an all EM/acoustic feature vector system could accomplish. In this manner, one can exclude all of the units identified from the first step (e.g., acoustically identified sound units in this example) except for one that meets the criteria defined by comparison with the library of stored feature vectors for the following steps. The order of sensor approach can be interchanged. The exclusive probability technique can identify the diphones, triphones, multiphones, words, and word sequences in the examined time frame.

The invention includes a method of using neural network algorithms to associate a pattern described with the feature vectors in conjunction with the symbolic representation of the corresponding sound units. This method uses the usual training methods for neural networks (including normalization and quantization of input feature vectors), the averaging of speakers (one or more), and associating the inputs though the neural network algorithms (back propagation, two or more layers, etc.) with known words or other speech units. Once trained, the networks provide a rapid association of an input feature vector to an identified output speech unit symbol because the input data from the methods are so well defined, speaker independent, and accurate.

The invention includes a method of synthesizing high quality, idiosyncratic speech from stored EM sensor obtained data for an individual speaker. Individual speaker means coding the speech of an average office dictation worker or a famous actor. The quality of the speech depends upon the quality of the coding of the original feature vectors, their storage in a code book, and the retrieval methods and concatenation methods. First the needed speech units are recorded, coded, and stored with associated symbols in a code book. Second, a commercial text to speech translator is used that identifies all of the required speech units (phonemes, diphones, triphones, etc.) from written text for the purpose of retrieving the desired speech feature vectors from the code book. Next the sound units to be used, the timing of the units, and the prosody are selected. The units are joined together by convoluting the excitation functions with the transfer functions to produce the output sound function, and using, in the preferred embodiment, the period of glottal closure as the timing "mark" for joining speech interval segments. Finally prosody is provided for each speech unit or combination of speech units; in particular it sets the sound level, and the pitch change from the beginning of the unit to the end as defined by phrasing and punctuation. Other concatenation approaches can be used as well, because the procedures allow easy selection of function values and derivatives.

The invention includes a method of altering the synthesized speech by altering the stored speech feature vectors. The pitch is changed by modifying the excitation function feature vector by increasing the number of glottal open and close cycles per unit time, and then convoluting this higher pitch excitation with the vocal tract transfer functions for each defined length feature time interval. This is done by compressing the descriptors of the excitation function so that a similar, but shortened pattern, in time, is derived. The individual speech feature vector can be altered to a predefined normalized speech vector. In addition, speech duration can be shortened or lengthened by adding or subtracting speech frames, including silence periods, in units of glottal periods.

The transfer function of the speaker can be altered in a known way by altering the physiological parameters in a known way, such as lengthening the vocal tract or increasing the size of the nasal cavity based upon the automatically derived data. Once the physiological parameters are changed, then a new transfer function feature vector (along with excitation and prosody vector elements) is formed based upon the new physiology of the vocal tract for the time frame being investigated.

The excitation function of a more desirable speaker, or the transfer function, or the prosody pattern for a given speaker can be substituted, before performing the convolution, upon demand, for the purpose of improved speech synthesis.

Synthetic excitation functions (e.g. unphysical open-close shapes, or very high pitch) can be generated, or non-physical modified transfer functions (e.g. based upon exaggerated physiological parameters) or amusing or desirable prosody patterns for the purposes of entertainment, speech research, animal research or training, or specially desired effects.

The invention includes using these coding techniques for the purposes of coding the feature vectors of a speaker speaking into a telephony set transmitter microphone. This coding includes attaching additional information as desired such as speaker identification, speech alteration if needed, and translating the feature vectors into appropriate code for transmission. The real time speech recognition of the speech can occur and the corresponding symbol can be identified, and transmitted with dramatic drop in bandwidth. These methods allow simplified encryption, foreign language translation, and minimal bandwidth coding for the transmission of the coded units via wire, optical fiber, or wireless in real time. The methods include how to synthesize the coded speech (e.g., symbols or feature vectors) into acoustic speech representing the speaker for broadcasting the rendered acoustic sounds through the telephony receiver to the listener. The speech synthesis can also be designed to use for identifying, sending, and/or synthesizing prestored average speaker qualities, to send "difference feature vectors", to send partial information using "most important" and "less important" functional fitting terms. It can be designed to transmit very high fidelity speaker idiosyncratic speech, and thereby use relatively higher bandwidth for the transmission of the more accurate description of the feature vector information, or minimal quality to minimize bandwidth.

The inverse communication channel works in the same fashion, except the listener becomes the speaker and the speaker the listener. Real time means that the recognizing, coding, and synthesizing can take place while speakers are speaking or while speech is being synthesized and with a time delay that is short enough for the users to be satisfied.

The invention also includes telephone coding using identification procedures where the speech recognition results in a word identification. The word character computer code (e.g. ASCII) is transmitted along with none or minimal speaker voice characterization information for the purpose of minimizing the bandwidth of transmission. Word (i.e., language symbols such as letters, pictograms, and other symbols) transmission is known to be about 100 fold less demanding of transmission bandwidth than present speech telephony; thus the value of this transmission is very high.

The methods include communication feedback to a user for many applications because the physiological as well as acoustic information is accurately coded and available for display or feedback. For speech correction or for foreign language learning, displays of the vocal organs show organ mispositioning by the speaker. For deaf speaker's, misarticulated sounds are identified and fed back using visual, tactile, or electrical stimulus units.

Changes and modifications in the specifically described embodiments can be carried out without departing from the scope of the invention which is intended to be limited only by the scope of the appended claims.

The invention claimed is:

1. A method for characterizing speech, comprising:
directing EM radiation toward speech organs of a speaker;
detecting EM radiation scattered from the speech organs to obtain speech organ information;
detecting acoustic speech output from the speaker to obtain acoustic speech information;
combining the EM speech organ information with the acoustic speech information using a speech coding algorithm to obtain the speaker's excitation function and speech tract transfer function.

2. The method of claim 1 further comprising defining a speech time frame.

3. The method of claim 2 further comprising defining the time of start, stop, and duration of the speech time frame.

4. The method of claim 2 further comprising forming feature vectors for each speech time frame.

5. The method of claim 4 further comprising forming difference feature vectors.

6. The method of claim 4 further comprising comparing a feature vector to stored feature vector information to identify a speaker.

7. The method of claim 4 further comprising comparing a feature vector to stored feature vector information in many language codebooks to identify the language being used by the speaker for the formation of acoustic speech units.

8. The method of claim 4 further comprising normalizing the feature vector of a speaker to that of one or more reference speakers.

9. The method of claim 4 further comprising quantizing a continuous coefficient-value band of a feature vector to a small number of distinct coefficient values representing a small number of distinct user-discernible, application-related speech conditions defined by each coefficient.

10. The method of claim 4 further comprising defining acoustic speech unit feature vectors by combining one or more excitation function feature vectors, vocal tract transfer function feature vectors, prosody feature vectors, timing, algorithm control coefficients, neighboring frame connectivity coefficients, and acoustic feature vectors for all acoustic units in a language.

11. The method of claim 10 further comprising storing the acoustic speech unit feature vectors in a library, code book, or database.

12. The method of claim 10 where a speech segment is compressed by:
forming a sequence of feature vectors for each sequential time frame in the speech segment;
comparing sequential changes in the feature vector coefficients, for each feature vector in the sequence, against a predefined model describing change in one or more of the coefficients over the sequential time frames;
forming a single representative feature vector for several time frames over which the coefficients meet the criteria of the predefined model;
adding to the representative feature vector extra coefficients describing the predefined model and a parametric fit to the model;
adding the total duration time of the several time frames to the representative, multi-time frame feature vector as an extra coefficient;
storing or transmitting the compressed segment electronically.

13. The method of claim 10 further comprising generating said combined feature vectors with identifying symbols for all acoustic speech units used in a language and storing them in a library, codebook or data base.

14. The method of claim 13 further comprising associating a foreign language word or phrase symbol in a second language with each unit of a first language coded by a speaker or speakers and storing them in a codebook or data base.

15. The method of claim 10 further comprising averaging feature vector coefficients from the excitation, transfer, acoustic, prosody, and timing functions of one or more speakers to form a reference speaker acoustic sound unit feature vector and storing them in a codebook or data base.

16. The method of claim 10 further comprising modifying feature vector coefficients and functional representations of the excitation, transfer, acoustic, prosody, neighboring frame connectivity, and timing functions of one or more speakers to form a modified acoustic sound unit feature vector and storing them in a codebook or data base.

17. The method of claim 4 further comprising identifying all sound units in a language from the feature vectors.

18. The method of claim 17 further comprising identifying all acoustic speech units in a language by a method selected from the group consisting of template matching techniques, HMM techniques, neural network techniques, a method of joint probabilities of two or more identifying algorithms, and a method of exclusion to reject identified units in a sequence of tests by two or more identifying algorithms.

19. The method of claim 17 further comprising identifying each acoustic speech unit with a symbol of the language unit identified.

20. The method of claim 4 further comprising communicating back to the speaker or to others speech organ articulation qualities, which are coded in the feature vectors for the speech time frames, by using communication vehicles selected from the group consisting of visual images, printed information, acoustic messages, and tactile and/or electrical stimulus.

21. The method of claim 2 wherein the speech time frame is defined by measuring glottal opening and closing using reflected EM waves.

22. The method of claim 21 further comprising defining a composite time frame from two or more glottal opening and closing time frames.

23. The method of claim 21 further comprising precalibrating an EM sensor so that the EM signals can be converted to either pressure and/or volume air flow in real time.

24. The method of claim 21 wherein a voiced excitation function feature vector is described by numerical table values or by fitting a mathematical functional model to the numerical table values.

25. The method of claim 21 comprising defining an unvoiced speech time frame by the absence of EM detected glottal opening/closing and the presence of acoustic output.

26. The method of claim 21 comprising forming the feature vector for combined voiced and unvoiced speech time frames.

27. The method of claim 2 comprising obtaining the excitation function for unvoiced speech.

28. The method of claim 1 further comprising deconvolving the speech excitation function from the acoustic speech information to produce a deconvolved transfer function.

29. The method of claim 28 further comprising forming a feature vector by fitting the deconvolved transfer function to a mathematical model.

30. The method of claim 29 wherein the feature vector is formed by one of numerical table look-up, Fourier transform, an ARMA model technique, an electrical or mechanical analog model of the acoustic system, or an organ-dimension physiological/acoustic-model of the acoustic system.

31. The method of claim 29 further comprising choosing the transfer function mathematical model using EM sensor information describing the dimensions and locations of vocal organs.

32. The method of claim 31 further comprising obtaining the transfer function using real time measurements.

33. The method of claim 29 further comprising dividing the transfer function into "important" pole-zero terms describing major vocal tract configurations and "less-important" pole-zero terms describing idiosyncratic speaker's vocal organ physical and acoustical conditions.

34. The method of claim 1 wherein the EM radiation is directed to and reflected from the glottal region and is sensed in the near field mode, the intermediate field mode, or the far field mode.

35. The method of claim 1 further comprising synthesizing speech from the EM and acoustic speech organ information.

36. The method of claim 35 wherein speech is synthesized by:

generating a code book of reference speaker feature vectors and identifying symbols;

identifying speech units for synthesis using a text to speech translator;

selecting the sound units and timing;

providing selected sound feature vectors from a stored data base;

concatenating the sound units in speech sound sequences;

modifying feature vector coefficients or sequences of feature vector coefficients using prosody rules;

modifying the time duration of individual sounds; and generating sound feature vectors by convolving the modified excitation functions with the modified transfer functions to produce an output sound function.

37. The method of claim 36 further comprising measuring positions on an excitation function amplitude versus time function to join speech interval segments together.

38. The method of claim 37 further comprising using a time during glottal closure as a timing marker for joining speech frame segments.

39. The method of claim 1 further comprising coding acoustic speech units, transmitting the codes to a receiver system, and reconstructing the transmitted codes to acoustic speech.

40. The method of claim 39 wherein the codes are symbolic codes.

41. The method of claim 39 further comprising modifying the codes to transmit minimal information, and reconstructing the codes to acoustic speech using locally stored code books of reference speakers.

42. The method of claim 39 further comprising obtaining an associated foreign language symbol or speech code, transmitting the foreign language code to the receiver system, and reconstructing to acoustic speech in the foreign language.

43. The method of claim 39 further coding the acoustic speech units in a first language, transmitting the coded information from the first language, recognizing the transmitted coded units, obtaining associated language symbols or speech codes in a second language from a system codebook at the receiver system, and reconstructing acoustic speech in the second language at the receiver system.

* * * * *